US012646621B2

(12) United States Patent
Nicula et al.

(10) Patent No.: US 12,646,621 B2
(45) Date of Patent: Jun. 2, 2026

(54) SYSTEMS AND METHODS FOR CANCER CONDITION DETERMINATION USING AUTOENCODERS

(71) Applicant: GRAIL, LLC, Menlo Park, CA (US)

(72) Inventors: Virgil Nicula, Cupertino, CA (US); Joshua Newman, Mountain View, CA (US)

(73) Assignee: Grail, Inc., Menlo Park, CA (US)

( * ) Notice: Subject to any disclaimer, the term of this patent is extended or adjusted under 35 U.S.C. 154(b) by 358 days.

(21) Appl. No.: 17/191,914

(22) Filed: Mar. 4, 2021

(65) Prior Publication Data

US 2021/0358626 A1 Nov. 18, 2021

Related U.S. Application Data

(60) Provisional application No. 62/985,258, filed on Mar. 4, 2020.

(51) Int. Cl.
| | |
|---|---|
| *G16H 50/20* | (2018.01) |
| *G16B 20/00* | (2019.01) |
| *G16B 40/00* | (2019.01) |

(52) U.S. Cl.
CPC ............. *G16H 50/20* (2018.01); *G16B 20/00* (2019.02); *G16B 40/00* (2019.02)

(58) Field of Classification Search
None
See application file for complete search history.

(56) References Cited

U.S. PATENT DOCUMENTS

| | | |
|---|---|---|
| 2018/0237863 A1 | 8/2018 | Namsaraev et al. |
| 2019/0287652 A1 | 9/2019 | Gross et al. |

(Continued)

FOREIGN PATENT DOCUMENTS

| | | | | |
|---|---|---|---|---|
| WO | WO 2018/081130 | 5/2018 | | |
| WO | WO-2018163051 A1 * | 9/2018 | ......... | A61K 31/7105 |

(Continued)

OTHER PUBLICATIONS

Jelinek, Jaroslav, et al. "Conserved DNA methylation patterns in healthy blood cells and extensive changes in leukemia measured by a new quantitative technique." Epigenetics 7.12 (2012): 1368-1378. (Year: 2012).*

(Continued)

*Primary Examiner* — Olivia M. Wise
*Assistant Examiner* — Mary C Leverett
(74) *Attorney, Agent, or Firm* — Fenwick & West LLP

(57) ABSTRACT

A method for discriminating a cancer state is provided. A first dataset is obtained for a plurality of subjects having a first cancer state. Each subject has a plurality of nucleic acid methylation fragments with methylation patterns comprising CpG site methylation states. An autoencoder including an encoder and decoder is trained by evaluating the error in the autoencoder reconstruction of the methylation pattern and nucleic acid sequence of each nucleic acid methylation fragment in the first dataset. A second dataset is obtained for a plurality of subjects having a second cancer state. A plurality of features is identified by inputting the methylation pattern and nucleic acid sequence of each nucleic acid methylation fragment in the second dataset into the trained autoencoder and computing a score determined by the autoencoder reconstruction of the methylation pattern. The plurality of features is used to train a supervised model that discriminates a cancer state.

23 Claims, 15 Drawing Sheets

Specification includes a Sequence Listing.

(56) References Cited

U.S. PATENT DOCUMENTS

| | | | |
|---|---|---|---|
| 2020/0239964 A1 | 7/2020 | Gross et al. | |
| 2020/0239965 A1 | 7/2020 | Fields et al. | |
| 2020/0365229 A1 | 11/2020 | Fields et al. | |
| 2020/0372296 A1 | 11/2020 | Maher | |
| 2020/0385813 A1 | 12/2020 | Venn | |

FOREIGN PATENT DOCUMENTS

| | | | | |
|---|---|---|---|---|
| WO | 2019195268 A2 | 10/2019 | | |
| WO | WO-2019200410 A1 | * 10/2019 | ........... | G06K 9/6267 |
| WO | WO-2019204360 A1 | * 10/2019 | ............ | G06N 20/00 |
| WO | WO 2020/069350 | 4/2020 | | |
| WO | WO 2020/154682 | 7/2020 | | |

OTHER PUBLICATIONS

Crowgey, Erin L., et al. "Epigenetic machine learning: utilizing DNA methylation patterns to predict spastic cerebral palsy." BMC bioinformatics 19 (2018): 1-10. (Year: 2018).*

Angermueller, Christof, et al. "DeepCpG: accurate prediction of single-cell DNA methylation states using deep learning." Genome biology 18.1 (2017): 1-13. (Year: 2017).*

Zhang, Xiaoyu, et al. "Integrated Multi-omics Analysis Using Variational Autoencoders: Application to Pan-cancer Classification." arXiv preprint arXiv:1908.06278 (2019). (Year: 2019).*

Liu, Qian, and Pingzhao Hu. "Association analysis of deep genomic features extracted by denoising autoencoders in breast cancer." Cancers 11.4 (2019): 494. (Year: 2019).*

Titus, Alexander J., et al. "Unsupervised deep learning with variational autoencoders applied to breast tumor genome-wide DNA methylation data with biologic feature extraction." BioRxiv 433763 (2018). (Year: 2018).*

U.S. Appl. No. 17/119,606, entitled "Cancer classification using patch convolutional neural networks," filed Dec. 11, 2020.

Agresti, An Introduction to Categorical Data Analysis, 1996, Chapter 5, pp. 103-144, John Wiley & Son, New York.

Ameniya et al. 2019, "The Encode Blacklist: Identification of Problematic Regions of the Genome," Scientific Reports 9, article No. 9354.

Boser et al., 1992, "A training algorithm for optimal margin classifiers," in Proceedings of the 5th Annual ACM Workshop on Computational Learning Theory, ACM Press, Pittsburgh, Pa., pp. 142-152.

Breiman, 1999, "Random Forests—Random Features," Technical Report 567, Statistics Department, U.C. Berkeley, Sep. 1999.

Doersch, 2016, "Tutorial on variational autoencoders." arXiv preprint arXiv: 1606.05908.

Du et al., 2010, BMC Bioinformatics 11 :587, doi: 10.1186/1471-2105-11-587.

Duda, Pattern Classification, Second Edition, 2001, John Wiley & Sons, Inc., pp. 259, 262-265, 395-396, 396-408, and 411-412.

Feng et al., 2020, "Soft Gradient Boosting Machine," arXiv:2006.04059.

Fernandes et al., 2017, "Transfer Learning with Partial Observability Applied to Cervical Cancer Screening," Pattern Recognition and Image Analysis: 8th Iberian Conference Proceedings, 243-250.

Furey et al., 2000, Bioinformatics 16, 906-914.

Grunau et al., 2001, "MethDB—a public database for DNA methylation data," Nucleic Acids Research 29(1), 270-274.

Hachiya et al., 2017, "Genomewide identification of inter-individually variable DNA methylation sites improves the efficacy of epigenetic association studies," NPJ Genom Med. 2017. 2: 11.

Hassoun, 1995, Fundamentals of Artificial Neural Networks, Massachusetts Institute of Technology.

Hastie, 2001, The Elements of Statistical Learning, Springer, New York.

Huang et al., 2021, "MethHC 2.0: information repository of DNA methylation and gene expression in human cancer," Nucleic Acids Research 49(Dl), Dl268-Dl275.

Jones, 2002, Oncogene 21 :5358-5360.

Kingma and Max, 2019, Foundations and Trends in Machine Learning, 12(4), ISSN 1935-8237.

Klein et al., 2018, "Development of a comprehensive cell-free DNA (cIDNA) assay for early detection of multiple tumor types: The Circulating Cell-free Genome Atlas (CCGA) study," J. Clin. Oncology 36(15), 12021-12021; doi: 10.1200/JCO.2018.36.15suppl.12021.

Kristiadi, 2016, "Variational Autoencoder: Intuition and Implementation,".

Larochelle et al., 2009, "Exploring strategies for training deep neural networks," J Mach Learn Res 10, pp. 1-40.

Liu et al., "Bisulfite-free direct detection of 5-methylcytosine and 5-hydroxymethylcytosine at base resolution," Nat Biotechnol, doi: 10.1038/s41587-019-0041-2.

Liu et al., 2019, "Genome-wide cell-free DNA (cIDNA) methylation signatures and effect on tissue of origin (TOO) performance," J. Clin. Oncology 37(15), 3049-3049; doi: 10.1200/JCO.2019.37.15suppl.3049.

Ongenaert et al., "PubMeth: a cancer methylation database combining text-mining and expert annotation," Nucleic Acids Research: doi: 10.1093/nar/gkm788.

Paska and Hudler, 2015, Biochemia Medica 25(2): 161-176.

Schliep et al., 2003, Bioinformatics 19(1): i255-i263.

Taheri and Mammadov, "Learning the naive Bayes classifier with optimization models," International Journal of Applied Mathematics and Computer Science 23( 4), 787-795.

Vapnik, 1998, Statistical Learning Theory, Wiley, New York; Mount, 2001, Bioinformatics: sequence and genome analysis, Cold Spring Harbor Laboratory Press, Cold Spring Harbor, N.Y.

Vincent et al., 2010, "Stacked denoising autoencoders: Learning useful representations in a deep network with a local denoising criterion," J Mach Learn Res 11, pp. 3371-3408.

Warton and Samimi, 2015, Front Mol Biosci, 2(13) doi: 10.3389/fmolb.2015.00013.

Yoon, 2009, "Hidden Markov Models and their Applications in Biological Sequence Analysis," Curr. Genomics. Sep; 10(6): 402-415, doi: 10.2174/138920209789177575.

Ziller et al., 2015, "Coverage recommendations for methylation analysis by whole-genome bisulfite sequencing," Nature Methods. 12(3):230-232, doi: 10.1038/nmeth.3152.

International Search Report and Written Opinion for PCT/US2021/020787; dated Jun. 16, 2021; 20 pages.

Mohammed Khwaja et. al; "A Deep Autoencoder System for Differentiation of Cancer Types Based on DNA Methylation State"; Oct. 5, 2018; 8 pages.

Masser, D.R. et al., "Targeted DNA Methylation Analysis by Next-generation Sequencing," Journal of Visualized Experiments (96), Feb. 24, 2015, pp. 1-11.

* cited by examiner

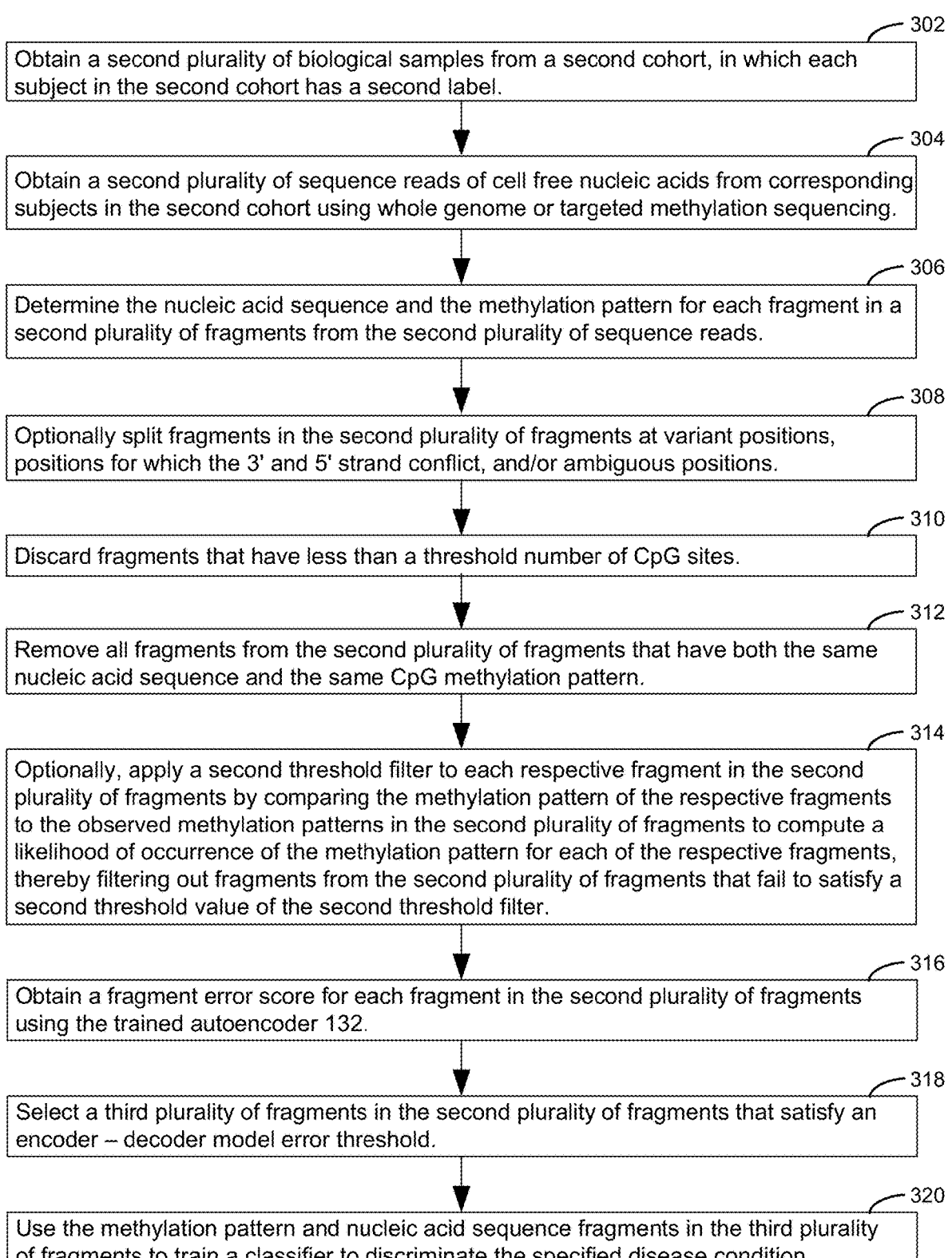

302
Obtain a second plurality of biological samples from a second cohort, in which each subject in the second cohort has a second label.

304
Obtain a second plurality of sequence reads of cell free nucleic acids from corresponding subjects in the second cohort using whole genome or targeted methylation sequencing.

306
Determine the nucleic acid sequence and the methylation pattern for each fragment in a second plurality of fragments from the second plurality of sequence reads.

308
Optionally split fragments in the second plurality of fragments at variant positions, positions for which the 3' and 5' strand conflict, and/or ambiguous positions.

310
Discard fragments that have less than a threshold number of CpG sites.

312
Remove all fragments from the second plurality of fragments that have both the same nucleic acid sequence and the same CpG methylation pattern.

314
Optionally, apply a second threshold filter to each respective fragment in the second plurality of fragments by comparing the methylation pattern of the respective fragments to the observed methylation patterns in the second plurality of fragments to compute a likelihood of occurrence of the methylation pattern for each of the respective fragments, thereby filtering out fragments from the second plurality of fragments that fail to satisfy a second threshold value of the second threshold filter.

316
Obtain a fragment error score for each fragment in the second plurality of fragments using the trained autoencoder 132.

318
Select a third plurality of fragments in the second plurality of fragments that satisfy an encoder – decoder model error threshold.

320
Use the methylation pattern and nucleic acid sequence fragments in the third plurality of fragments to train a classifier to discriminate the specified disease condition.

Optionally, apply a first threshold filter to the methylation pattern of each respective fragment in the first plurality of fragments using the methylation patterns observed across the first plurality of fragments thereby filtering out all fragments from the first plurality of fragments that fail to satisfy a first threshold value of the first threshold filter {Figure 4}.

ATCCGGGGGATTCGCATATAATGAGGCTAATCGAAATTCGCCCAACG    Fragment One  (SEQ ID No: 13)

| A | B | C | D | E | Methylation site |
|---|---|---|---|---|---|
| 1 | 0 | 0 | 0 | 0 | Methylation pattern: |

("1" = methylated, "0" not methylated)

• • •

ATTCGCATATAATGAGGCTAATCGAAATTCGCCCAACGGATCG    Fragment N  (SEQ ID No: 14)

| B | C | D | E | F | Methylation site Identifier |
|---|---|---|---|---|---|
| 1 | 0 | 0 | 0 | 1 | Methylation pattern |

Use the methylation patterns observed across the first plurality of fragments to build a state distribution for the CpG site states collectively represented by the first plurality of fragments:

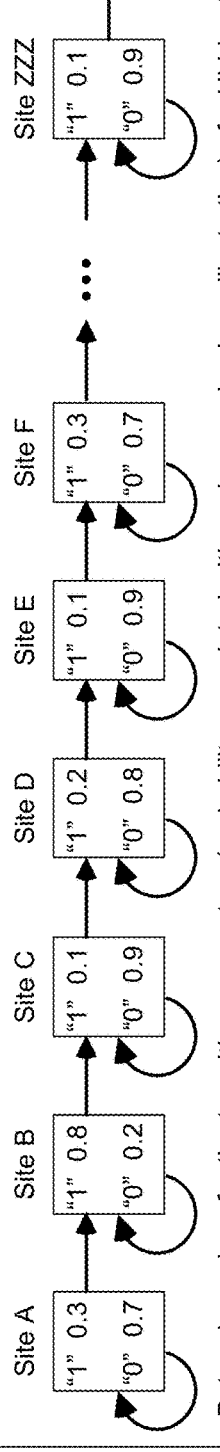

Determine values for the transition parameters (probability associated with each arrow in above illustration) of a Hidden Markov Model (HMM) using the state distribution for the CpG site states (e.g., using an expectation maximization algorithm such as the Baum-Welch algorithm), thereby training the HMM.

For each respective fragment in the first plurality of fragments, use the trained HMM model to determine the likelihood of occurrence of the methylation pattern of the respective fragment (e.g., using the forward algorithm). Discard fragments whose likelihoods of occurrence fail to satisfy a first threshold value of the first threshold filter (e.g., their methylation patterns are too common in the first plurality of fragments).

A method of discriminating between a first cancer state and a second cancer state.

504

Obtain a a first training dataset, in electronic form, where the first training dataset comprises, for each respective training subject in a first plurality of training subjects, a corresponding methylation pattern and a corresponding nucleic acid sequence of each respective nucleic acid methylation fragment in a corresponding plurality of nucleic acid methylation fragments determined by a methylation sequencing of nucleic acids in a biological sample obtained from the respective subject. The corresponding methylation pattern comprises a methylation state of each respective CpG site in a corresponding plurality of CpG sites in the respective nucleic acid methylation fragment. Each training subject in the first plurality of training subjects has the first cancer state.

506

The biological sample is a blood sample.

508

The biological sample comprises blood, whole blood, plasma, serum, urine, cerebrospinal fluid, fecal, saliva, sweat, tears, pleural fluid, pericardial fluid, or peritoneal fluid of the test subject.

510

The respective biological sample is homogenous for the first cancer state..

512

The respective biological sample is a tumor sample that is homogenous for the first cancer state.

514

The methylation sequencing of nucleic acids in a biological sample obtained from the respective subject is methylation sequencing of cell-free nucleic acids in the biological sample.

516

The methylation sequencing is i) whole genome methylation sequencing or ii) targeted DNA methylation sequencing using a plurality of nucleic acid probes.

518

The methylation sequencing detects one or more 5-methylcytosine (5mC) and/or 5-hydroxymethylcytosine (5hmC) in respective fragments.

520

The methylation sequencing of nucleic acids comprises conversion of one or more unmethylated cytosines or one or more methylated cytosines, in respective nucleic acid methylation fragments, to a corresponding one or more uracils.

Figure 5A

Train an untrained autoencoder, where the untrained autoencoder includes an encoder and a decoder, using the corresponding methylation pattern and the corresponding nucleic acid sequence of each respective nucleic acid methylation fragment in each corresponding plurality of nucleic acid methylation fragments in the first training dataset as input, by, for each corresponding nucleic acid sequence of each respective nucleic acid methylation fragment in each corresponding plurality of nucleic acid methylation fragments in the first training dataset, evaluating a first error function for an error in the reconstruction by the autoencoder of the corresponding methylation pattern and the corresponding nucleic acid sequence of the corresponding nucleic acid methylation fragment, thereby forming a trained autoencoder.

522

524

The encoder encodes the corresponding methylation pattern and the corresponding nucleic acid sequence of the corresponding nucleic acid methylation fragment in each corresponding plurality of nucleic acid methylation fragments in the first training dataset thereby forming a plurality of latent features. The decoder decodes the plurality of latent features into a reconstruction of the corresponding methylation pattern and the corresponding nucleic acid sequence of the corresponding nucleic acid methylation fragment.

526

The autoencoder is a variational autoencoder, a stacked denoising deep autoencoder, a deep recurrent autoencoder, a convolutional autoencoder, or a transformer network.

528

The autoencoder is a deep recurrent autoencoder and the training, for a respective sequence read in a corresponding plurality of sequence reads in the first training dataset feeds a first track of the deep recurrent autoencoder the corresponding nucleic acid sequence of the respective nucleic acid methylation fragment broken up into a plurality of k-mers, and feeds a second track of the deep recurrent autoencoder the corresponding methylation pattern of the respective nucleic acid methylation fragment.

530

The training comprises evaluating the first error function for an error in the reconstruction by the autoencoder in accordance with a gradient descent algorithm.

532

The error calculated for the trained autoencoder across the first training dataset satisfies an error threshold.

Figure 5B

534

Obtain a second training dataset, in electronic form, where the second training dataset comprises, for each respective subject in a second plurality of training subjects, a corresponding methylation pattern and a corresponding nucleic acid sequence of each respective nucleic acid methylation fragment in a corresponding plurality of nucleic acid methylation fragments determined by a methylation sequencing of nucleic acids in a biological sample obtained from the respective subject. The corresponding methylation pattern comprises a methylation state of each respective CpG site in a corresponding plurality of CpG sites in the respective nucleic acid methylation fragment. Each training subject in the second plurality of training subjects has the second cancer state.

536

The corresponding plurality of nucleic acid methylation fragments determined by a methylation sequencing of nucleic acids in a biological sample obtained from the respective subject in the first training dataset or the second training dataset comprises one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments.

538

The second plurality of training subjects comprises 30 or less, 50 or less, 100 or less, or 1000 or less training subjects.

Figure 5C

540

Use the second training dataset 120-2 and the trained autoencoder 132 to identify a plurality of features 146 from among a plurality of sequences or a plurality of methylation patterns represented by the second training dataset. Compute, for each respective nucleic acid methylation fragment in each corresponding plurality of nucleic acid methylation fragments in the second training dataset, a corresponding score determined at least in part by a reconstruction of the corresponding methylation pattern of the respective nucleic acid methylation fragment by the autoencoder upon inputting the corresponding methylation pattern and the corresponding nucleic acid sequence of the respective nucleic acid methylation fragment into the trained autoencoder.

542

The corresponding score for a respective nucleic acid methylation fragment is determined by the correctness of the reconstruction of the corresponding methylation pattern of the respective nucleic acid methylation fragment by the autoencoder 132, and is independent of the correctness of the reconstruction of the corresponding nucleic acid sequence of the respective nucleic acid methylation fragment by the autoencoder.

544

The corresponding score for a respective nucleic acid methylation fragment is determined by the correctness of the reconstruction of the corresponding methylation pattern of the respective nucleic acid methylation fragment by the autoencoder 132, and is further determined by the the correctness of the reconstruction of the corresponding nucleic acid sequence of the respective nucleic acid methylation fragment by the autoencoder.

546

The corresponding score is computed using the first error function.

548

The corresponding score for a respective nucleic acid methylation fragment is computed using a second error function that is different than the first error function.

550

Each nucleic acid sequence represented by the second dataset that corresponds to one or more nucleic acid methylation fragments in the second dataset receiving a corresponding score that satisfies an error threshold is identified as a feature in the plurality of features.

552

The using selects a methylation pattern associated with a corresponding score on the basis that it is in the top N corresponding score achieved by the using as a feature in the plurality of features.

Figure 5D

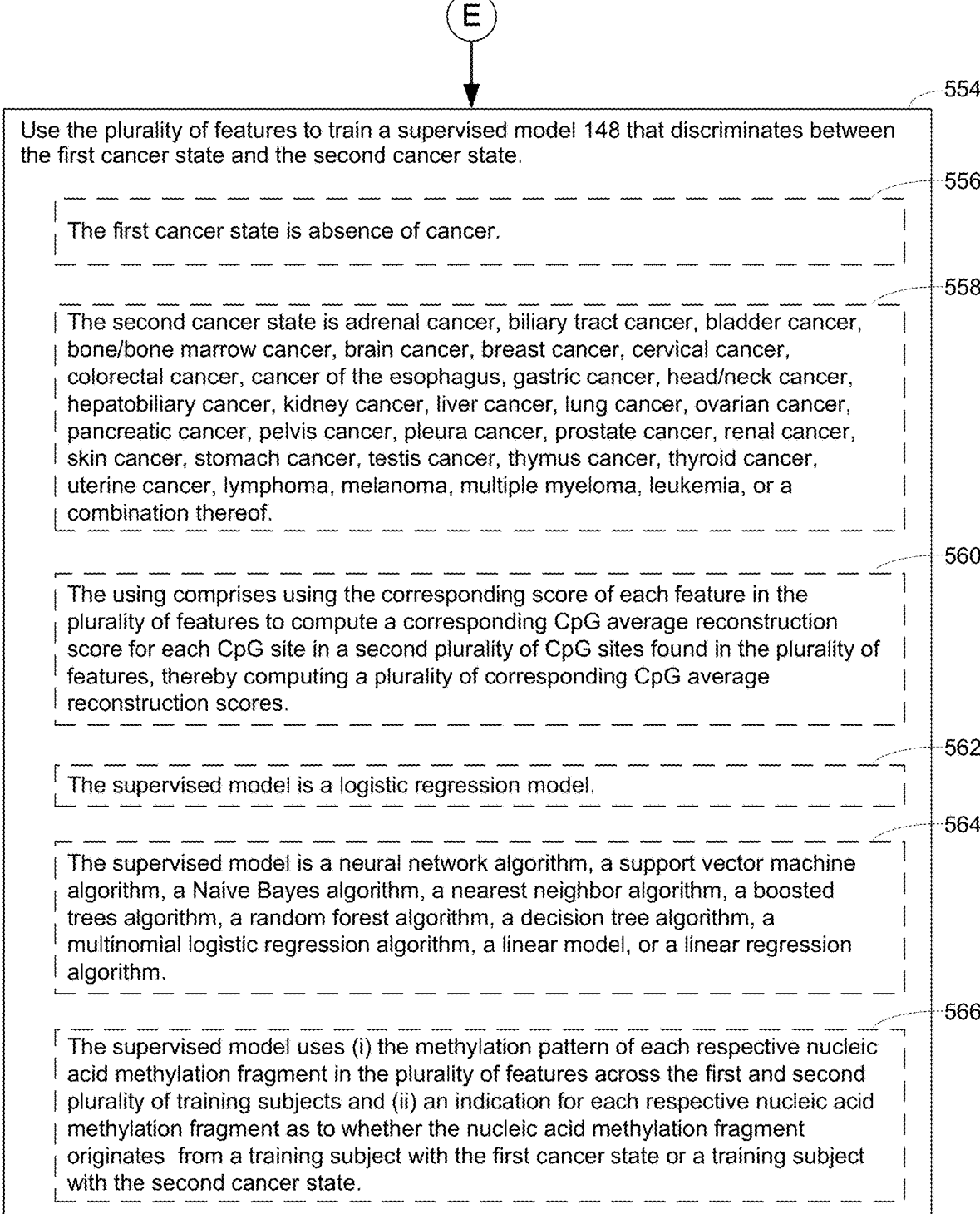

Ⓔ

554

Use the plurality of features to train a supervised model 148 that discriminates between the first cancer state and the second cancer state.

556

The first cancer state is absence of cancer.

558

The second cancer state is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

560

The using comprises using the corresponding score of each feature in the plurality of features to compute a corresponding CpG average reconstruction score for each CpG site in a second plurality of CpG sites found in the plurality of features, thereby computing a plurality of corresponding CpG average reconstruction scores.

562

The supervised model is a logistic regression model.

564

The supervised model is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

566

The supervised model uses (i) the methylation pattern of each respective nucleic acid methylation fragment in the plurality of features across the first and second plurality of training subjects and (ii) an indication for each respective nucleic acid methylation fragment as to whether the nucleic acid methylation fragment originates from a training subject with the first cancer state or a training subject with the second cancer state.

Method 900

SEQUENCE LISTING

```
<160> NUMBER OF SEQ ID NOS: 14

<210> SEQ ID NO 1
<211> LENGTH: 131
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 4
<223> OTHER INFORMATION: m5C
<220> FEATURE:
<221> NAME/KEY: modified_base
<222> LOCATION: 128
<223> OTHER INFORMATION: m5C

<400> SEQUENCE: 1
tccngctgga ggccctgcgg gagaaggcac tgaggatgct gggggaggcg gtgcgcgacg      60
gtgggcagca cgctcgcgac cccgtcgggg gctccgtgga gttccagttt gtgcctgtgc     120
tcaagctngt g                                                          131

<210> SEQ ID NO 2
<211> LENGTH: 131
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 4
<223> OTHER INFORMATION: m5C
<220> FEATURE:
```

```
<221> NAME/KEY: modified_base
<222> LOCATION: 56
<223> OTHER INFORMATION: m5C
<220> FEATURE:
<221> NAME/KEY: modified_base
<222> LOCATION: 77
<223> OTHER INFORMATION: m5C
<220> FEATURE:
<221> NAME/KEY: modified_base
<222> LOCATION: 86
<223> OTHER INFORMATION: m5C
<220> FEATURE:
<221> NAME/KEY: modified_base
<222> LOCATION: 128
<223> OTHER INFORMATION: m5C

<400> SEQUENCE: 2
tccngctgga ggccctgagg gaaaaggcac agaggatgca gggggaggag gagcgngacg      60
gagggcagca cgcacgngac cccgtngggg gcaccgagga gtaccagatt gagcctgagc     120
tatagcangt g                                                          131

<210> SEQ ID NO 3
<211> LENGTH: 102
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 2
<223> OTHER INFORMATION: m5C
<220> FEATURE:
<221> NAME/KEY: modified_base
<222> LOCATION: 10
<223> OTHER INFORMATION: m5C
<220> FEATURE:
<221> NAME/KEY: modified_base
<222> LOCATION: 26
<223> OTHER INFORMATION: m5C
<220> FEATURE:
<221> NAME/KEY: modified_base
<222> LOCATION: 93
<223> OTHER INFORMATION: m5C

<400> SEQUENCE: 3
gngtgggcan gaggaagagg cccccnggcc cagcccgtga gcttctccgt gagccgcagg      60
tgggcagaga ggccgagcac acaccttggg gtngccttag aa                        102

<210> SEQ ID NO 4
<211> LENGTH: 101
<212> TYPE: DNA
<213> ORGANISM: Artificial Sequence
<220> FEATURE:
<223> OTHER INFORMATION: Synthetic Nucleic Acid

<400> SEQUENCE: 4
gcgagggcac gcggaagagg cctccaggca cagcccgtga gcatccccga gagacgcagg      60
tgggcaggga ggccgagcac acaccaaggg gtagccatcg a                         101

<210> SEQ ID NO 5
<211> LENGTH: 112
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 4
<223> OTHER INFORMATION: m5C
```

```
<220> FEATURE:
<221> NAME/KEY: modified_base
<222> LOCATION: 19
<223> OTHER INFORMATION: m5C
<220> FEATURE:
<221> NAME/KEY: modified_base
<222> LOCATION: 89
<223> OTHER INFORMATION: m5C

<400> SEQUENCE: 5 gaangggggtc atgcccatng ccatgagcat caaggcaggc acggtggatg aggactcgtc      60
aggctccgag tgagtgtggc cgggtgggng ggacggggtg cagccccgcg ga             112

<210> SEQ ID NO 6
<211> LENGTH: 112
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 4
<223> OTHER INFORMATION: m5C
<220> FEATURE:
<221> NAME/KEY: modified_base
<222> LOCATION: 67
<223> OTHER INFORMATION: m5C

<400> SEQUENCE: 6 gaangggggac aagcccaaag ccaagagcaa caaggcaggc acggtggaag aggacacgcc      60
aggctcngag tgagtgaggc cgggtgggcg ggacggggtg cagacccacg ga             112

<210> SEQ ID NO 7
<211> LENGTH: 122
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 4
<223> OTHER INFORMATION: m5C
<220> FEATURE:
<221> NAME/KEY: modified_base
<222> LOCATION: 63
<223> OTHER INFORMATION: m5C
<220> FEATURE:
<221> NAME/KEY: modified_base
<222> LOCATION: 77
<223> OTHER INFORMATION: m5C
<220> FEATURE:
<221> NAME/KEY: modified_base
<222> LOCATION: 79
<223> OTHER INFORMATION: m5C
<220> FEATURE:
<221> NAME/KEY: modified_base
<222> LOCATION: 89
<223> OTHER INFORMATION: m5C
<220> FEATURE:
<221> NAME/KEY: modified_base
<222> LOCATION: 95
<223> OTHER INFORMATION: m5C
<220> FEATURE:
<221> NAME/KEY: modified_base
<222> LOCATION: 103
<223> OTHER INFORMATION: m5C
<220> FEATURE:
<221> NAME/KEY: modified_base
<222> LOCATION: 107
<223> OTHER INFORMATION: m5C
<220> FEATURE:
<221> NAME/KEY: modified_base
<222> LOCATION: 110
```

```
<223> OTHER INFORMATION: m5C
<220> FEATURE:
<221> NAME/KEY: modified_base
<222> LOCATION: 113
<223> OTHER INFORMATION: m5C

<400> SEQUENCE: 7
gagnggagcc tagggagagg gaggagcaca tcttgatgca gagatgctgc agtggctccg      60
ggngcgctca cacacangng ccctcaccng ccacngccgc cgnggcngcn gcngcacccg     120
ga                                                                    122

<210> SEQ ID NO 8
<211> LENGTH: 122
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 4
<223> OTHER INFORMATION: m5C
<220> FEATURE:
<221> NAME/KEY: modified_base
<222> LOCATION: 77
<223> OTHER INFORMATION: m5C
<220> FEATURE:
<221> NAME/KEY: modified_base
<222> LOCATION: 103
<223> OTHER INFORMATION: m5C
<220> FEATURE:
<221> NAME/KEY: modified_base
<222> LOCATION: 110
<223> OTHER INFORMATION: m5C
<220> FEATURE:
<221> NAME/KEY: modified_base
<222> LOCATION: 113
<223> OTHER INFORMATION: m5C

<400> SEQUENCE: 8
gagnggagcc tagggagagg gagaagcaca acacaatgca gagatgctgc agaggcaccg      60
ggcgcgcaca cacacangag cccacaccag ccaccgccgc cgnggccgtn gcngcacccg     120
ga                                                                    122

<210> SEQ ID NO 9
<211> LENGTH: 102
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 3
<223> OTHER INFORMATION: m5C
<220> FEATURE:
<221> NAME/KEY: modified_base
<222> LOCATION: 9
<223> OTHER INFORMATION: m5C
<220> FEATURE:
<221> NAME/KEY: modified_base
<222> LOCATION: 15
<223> OTHER INFORMATION: m5C
<220> FEATURE:
<221> NAME/KEY: modified_base
<222> LOCATION: 84
<223> OTHER INFORMATION: m5C
<220> FEATURE:
<221> NAME/KEY: modified_base
<222> LOCATION: 97
<223> OTHER INFORMATION: m5C
<220> FEATURE:
<221> NAME/KEY: modified_base
```

```
<222> LOCATION: 99
<223> OTHER INFORMATION: m5C

<400> SEQUENCE: 9
acnggtttng gtggngccgg cagccgagcc cagggctgta gtagtggcag acttggtagc      60
acaggggcct tgggaaggtg ggcnggcagc ccaccangng cc                        102

<210> SEQ ID NO 10
<211> LENGTH: 100
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 83
<223> OTHER INFORMATION: m5C
<220> FEATURE:
<221> NAME/KEY: modified_base
<222> LOCATION: 96
<223> OTHER INFORMATION: m5C

<400> SEQUENCE: 10
aatagtttcg gaggcgcagg cagccgaccc agggatgtcg aagtggcaga caaggacgca      60
caggggccat gggaaggggg gcnggcagcc ccccangagc                           100

<210> SEQ ID NO 11
<211> LENGTH: 38
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 3
<223> OTHER INFORMATION: m5C
<220> FEATURE:
<221> NAME/KEY: modified_base
<222> LOCATION: 20
<223> OTHER INFORMATION: m5C
<220> FEATURE:
<221> NAME/KEY: conflict
<222> LOCATION: 24
<223> OTHER INFORMATION: u
<220> FEATURE:
<221> NAME/KEY: modified_base
<222> LOCATION: 29
<223> OTHER INFORMATION: m5C
<220> FEATURE:
<221> NAME/KEY: modified_base
<222> LOCATION: 32
<223> OTHER INFORMATION: m5C
<220> FEATURE:
<221> NAME/KEY: modified_base
<222> LOCATION: 36
<223> OTHER INFORMATION: m5C

<400> SEQUENCE: 11
acngtggcug gttaaattcn gatnatacng cnggcngt                             38

<210> SEQ ID NO 12
<211> LENGTH: 38
<212> TYPE: DNA
<213> ORGANISM: Artificial Sequence
<220> FEATURE:
<223> OTHER INFORMATION: synthesized
<220> FEATURE:
<221> NAME/KEY: modified_base
<222> LOCATION: 3
<223> OTHER INFORMATION: m5C
<220> FEATURE:
```

```
<221> NAME/KEY: modified_base
<222> LOCATION: 20
<223> OTHER INFORMATION: m5C
<220> FEATURE:
<221> NAME/KEY: modified_base
<222> LOCATION: 29
<223> OTHER INFORMATION: m5C
<220> FEATURE:
<221> NAME/KEY: modified_base
<222> LOCATION: 32
<223> OTHER INFORMATION: m5C
<220> FEATURE:
<221> NAME/KEY: modified_base
<222> LOCATION: 36
<223> OTHER INFORMATION: m5C

<400> SEQUENCE: 12
acngtggcug gataaattcn gattatacng cnggcugt                              38

<210> SEQ ID NO 13
<211> LENGTH: 47
<212> TYPE: DNA
<213> ORGANISM: Artificial Sequence
<220> FEATURE:
<223> OTHER INFORMATION: Synthetic Nucleic Acid

<400> SEQUENCE: 13
atcgggggat tcgcatataa tgaggctaat cgaaatttcg cccaacg                    47

<210> SEQ ID NO 14
<211> LENGTH: 43
<212> TYPE: DNA
<213> ORGANISM: Artificial Sequence
<220> FEATURE:
<223> OTHER INFORMATION: Synthetic Nucleic Acid

<400> SEQUENCE: 14
attcgcatat aatgaggcta atcgaaattt cgcccaacga tcg                        43
```

1

SYSTEMS AND METHODS FOR CANCER CONDITION DETERMINATION USING AUTOENCODERS

CROSS REFERENCE TO RELATED PATENT APPLICATION

This application claims priority to U.S. Provisional Patent Application No. 62/985,258 entitled "Systems and Methods for Cancer Condition Determination Using Autoencoders," filed Mar. 4, 2020, which is hereby incorporated by reference.

SEQUENCE LISTING

The instant application contains a Sequence Listing that has been submitted electronically and in ASCII format and is hereby incorporated by reference in its entirety. Said ASCII copy, created Mar. 4, 2020, is named 121059-5018-PR_ST25.txt and is 4 kilobytes in size.

TECHNICAL FIELD

This specification relates generally to using methylation patterns in biological samples to discriminate and/or detect a cancer state.

BACKGROUND

Earlier detection of cancer is one of the most humane ways to improve cancer outcomes. Status quo treatments, such as the combination of surgery, chemotherapy and radiation for solid tumors, or chemotherapy and bone marrow transplants for liquid tumors, have drawbacks including unsatisfactory survival rates. Treatments often leave patients in pain, while providing only a limited amount of survival time. New immunotherapies have additional disadvantages, such as requiring patients to be treated in intensive care units and often imparting deadly side effects. All such treatments are more effective when cancer is detected early.

Although screening tests can be utilized for earlier detection of cancer, conventional methods for screening are frequently unsatisfactory. Monitoring methods such as mammography, colonoscopy, Pap smears and testing for prostate-specific antigen (PSA) have been in use for decades, but not all are uniformly successful. Some lesions progress so slowly that a patient is more likely to die of a secondary ailment, while some dangerous tumors go undetected until it is too late for treatment. Moreover, to date, no satisfactory screening test is available for lung cancer, among others.

To develop such screening tests, then, there is a need to define "biomarkers" of cancerous cells. These can be almost anything released by cancer cells, such as a strand of genetic material. The National Cancer Institute is supporting large initiatives with the hope that such biomarkers will not only provide the earliest footprints of cancer but also help to separate aggressive tumors from non-life-threatening ones. Advances in biomolecule sequencing, in particular with respect to nucleic acid samples, have revolutionized the fields of cellular and molecular biology and provide a promising technology for discovering such biomarkers. Facilitated by the development of automated sequencing systems, it is now possible to sequence whole genomes.

One particular approach to finding biomarkers is to use such sequencing to identify aberrant DNA methylation patterns. While DNA methylation plays an important role in regulating gene expression, aberrant DNA methylation has been implicated in many disease processes, including cancer. Furthermore, specific patterns of methylation have been determined to be associated with particular cancer conditions. See, e.g., Jones, 2002, Oncogene 21:5358-5360; Paska and Hudler, 2015, Biochemia Medica 25(2):161-176, and Du et al., 2010, BMC Bioinformatics 11:587, doi:10.1186/1471-2105-11-587. DNA methylation profiling using methylation sequencing, such as whole-genome bisulfite sequencing, is increasingly recognized as a valuable diagnostic tool for detection, diagnosis, or monitoring of cancer. For example, differential region- or allele-specific methylation patterns may be useful as molecular markers for non-invasive diagnostics using circulating cell-free DNA. See, e.g., Warton and Samimi, 2015, Front Mol Biosci, 2(13) doi: 10.3389/fmolb.2015.00013.

While new sequencing technologies have made large-scale sequencing, including methylation sequencing, possible, there has also been a commensurate increase in the number and complexity of the genomes that are being sequenced with these new sequencing technologies. Although large quantities of high-fidelity nucleic acid sequences can now be obtained, there remain many issues with assembling and organizing these sequences into complete genomes and/or identifying usable or informative biomarkers from these large and highly complex datasets.

Given the above background, there is a need in the art for improved approaches for identifying biomarkers using increasingly complex and large-scale nucleic acid sequencing data. Further, there is a need in the art for improved methods to use such biomarkers to model and infer complex biological patterns and non-linearities across the genome and thus develop tests for the detection, diagnosis, and/or monitoring of diseases, such as cancer.

SUMMARY

The implementations described herein address the shortcomings identified in the background by providing various technical solutions for discriminating between cancer states. A first dataset is obtained for a plurality of subjects having a first cancer state. Each subject in the plurality of subjects associated with the first dataset has a plurality of nucleic acid methylation fragments determined by a methylation sequencing of nucleic acids in a biological sample obtained from the subject. Each such nucleic acid methylation fragment comprises a nucleic acid sequence and a methylation pattern comprising methylation states of CpG sites. An autoencoder including an encoder and a decoder is trained by evaluating an error function for an error in the reconstruction by the autoencoder of the methylation pattern and nucleic acid sequence of each nucleic acid methylation fragment in the first dataset. A second dataset is obtained for a plurality of subjects having a second cancer state. Each subject in the plurality of subjects associated with the second dataset has a plurality of nucleic acid methylation fragments determined by a methylation sequencing of nucleic acids in a biological sample obtained from the subject. Each such nucleic acid methylation fragment comprises a nucleic acid sequence and a methylation pattern comprising methylation states of CpG sites. A plurality of features is identified by inputting the methylation pattern and nucleic acid sequence of each nucleic acid methylation fragment in the second dataset into the trained autoencoder and computing a score determined by the reconstruction by the autoencoder of the methylation pattern. The plurality of features is used to train a supervised model that discriminates a cancer state.

One aspect of the present disclosure provides a method of discriminating between cancer states, such as a first and second cancer state where the first cancer state is different than the second cancer state, at a computer system comprising at least one processor and a memory storing at least one program for execution by the at least one processor. The at least one program comprises instructions for obtaining a first training dataset, in electronic form. The first training dataset comprises, for each respective training subject in a first plurality of training subjects, a corresponding methylation pattern and a corresponding nucleic acid sequence of each respective nucleic acid methylation fragment in a corresponding plurality of nucleic acid methylation fragments determined by methylation sequencing of nucleic acids in a biological sample obtained from the respective subject. The corresponding methylation pattern comprises a methylation state of each respective CpG site in a corresponding plurality of CpG sites in the respective nucleic acid methylation fragment. Each training subject in the first plurality of training subjects has the first cancer state.

The method further comprises training an untrained autoencoder, where the untrained autoencoder includes an encoder and a decoder, using the corresponding methylation pattern and the corresponding nucleic acid sequence of each respective nucleic acid methylation fragment in each corresponding plurality of nucleic acid methylation fragments in the first training dataset as input. The training is performed by, for each corresponding nucleic acid sequence of each respective nucleic acid methylation fragment in each corresponding plurality of nucleic acid methylation fragments in the first training dataset, evaluating a first error function for an error in the reconstruction by the autoencoder of the corresponding methylation pattern and the corresponding nucleic acid sequence of the corresponding nucleic acid methylation fragment, thereby forming a trained autoencoder.

The method further comprises obtaining a second training dataset, in electronic form. The second training dataset comprises, for each respective subject in a second plurality of training subjects, a corresponding methylation pattern and a corresponding nucleic acid sequence of each respective nucleic acid methylation fragment in a corresponding plurality of nucleic acid methylation fragments determined by a methylation sequencing of nucleic acids in a biological sample obtained from the respective subject. The corresponding methylation pattern comprises a methylation state of each respective CpG site in a corresponding plurality of CpG sites in the respective nucleic acid methylation fragment. Each training subject in the second plurality of training subjects has the second cancer state.

The method further comprises using the second training dataset and the trained autoencoder to identify a plurality of features from among a plurality of sequences or a plurality of methylation patterns represented by the second training dataset. This is done by computing, for each respective nucleic acid methylation fragment in each corresponding plurality of nucleic acid methylation fragments in the second training dataset, a corresponding score determined at least in part by a reconstruction of the corresponding methylation pattern of the respective nucleic acid methylation fragment by the autoencoder upon inputting the corresponding methylation pattern and the corresponding nucleic acid sequence of the respective nucleic acid methylation fragment into the trained autoencoder.

The method further comprises using the plurality of features to train a supervised model that discriminates between the first cancer state and the second cancer state.

In some embodiments, each nucleic acid sequence represented by the second dataset that corresponds to one or more nucleic acid methylation fragments in the second dataset receiving a corresponding score that satisfies an error threshold is identified as a feature in the plurality of features.

In some embodiments, the corresponding score for a respective nucleic acid methylation fragment is determined by a correctness of the reconstruction of the corresponding methylation pattern of the respective nucleic acid methylation fragment by the autoencoder, and is independent of a correctness of the reconstruction of the corresponding nucleic acid sequence of the respective nucleic acid methylation fragment by the autoencoder.

In some embodiments, the corresponding score for a respective nucleic acid methylation fragment is determined by a correctness of the reconstruction of the corresponding methylation pattern of the respective nucleic acid methylation fragment by the autoencoder, and is further determined by a the correctness of the reconstruction of the corresponding nucleic acid sequence of the respective nucleic acid methylation fragment by the autoencoder.

In some embodiments, the correctness of the reconstruction of the corresponding methylation pattern of the respective nucleic acid methylation fragment is determined, at least in part, by a Hamming distance between the reconstruction of the corresponding methylation pattern of the respective nucleic acid methylation fragment and the actual methylation pattern of the respective nucleic acid methylation fragment.

In some embodiments, the corresponding plurality of nucleic acid methylation fragments determined by a methylation sequencing of nucleic acids in a biological sample obtained from the respective subject in the first training dataset or the second training dataset comprises one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments. In some embodiments, the first plurality of training subjects comprises 10 or more, 20 or more, 30 or more, 50 or more, 100 or more, 1000 or more, 2000 or more, 3000 or more, or 5000 or more training subjects. In some embodiments, the second plurality of training subjects comprises 30 or less, 50 or less, 100 or less, or 1000 or less training subjects.

In some embodiments, the at least one program further comprises instructions for, after the obtaining the dataset and prior to the training the autoencoder, filtering each corresponding plurality of nucleic acid methylation fragments by removing, from the corresponding plurality of nucleic acid methylation fragments, each respective nucleic acid methylation fragment that fails to satisfy one or more selection criteria.

In some such embodiments, the respective nucleic acid methylation fragment fails to satisfy a selection criterion in the one or more selection criteria when the methylation pattern of the respective nucleic acid methylation fragment has an output p-value that fails to satisfy a p-value threshold, and the output p-value of the respective nucleic acid methylation fragment is determined, at least in part, based upon a comparison of the methylation pattern of the respective nucleic acid methylation fragment over a plurality of CpG sites of the respective nucleic acid methylation fragment (e.g., two or more sites, three or more sites, four or more sites, five or more sites, six or more sites, seven or more sites, eight or more sites, nine or more sites, 10 or more sites, 11 or more sites, 12 or more sites, 13 or more sites, 14 or more sites, or 15 or more sites) to a corresponding distribution of methylation patterns of those nucleic acid methylation fragments in the first training dataset that have the corresponding plurality of CpG sites.

In some embodiments, the respective nucleic acid methylation fragment from the first training dataset fails to satisfy a selection criterion in the one or more selection criteria when an output p-value provided by a trained Markov model, responsive to input of the methylation pattern of the respective nucleic acid methylation fragment, fails the selection criterion. The trained Markov model is trained, at least in part, based upon evaluation of a methylation state of each CpG site in a plurality of CpG sites (e.g., two or more sites, three or more sites, four or more sites, five or more sites, six or more sites, seven or more sites, eight or more sites, nine or more sites, 10 or more sites, 11 or more sites, 12 or more sites, 13 or more sites, 14 or more sites, or 15 or more sites) of the respective nucleic acid methylation fragment across those nucleic acid methylation fragments in the first training dataset that have the corresponding plurality of CpG sites.

In some embodiments, the respective nucleic acid methylation fragment from the second training dataset fails to satisfy a selection criterion in the one or more selection criteria when an output p-value of a trained Markov model, responsive to input of the methylation pattern of the respective nucleic acid methylation fragment, fails the selection criterion. The trained Markov model is trained, at least in part, based upon evaluation of a methylation state of each CpG site in a plurality of CpG sites (e.g., two or more sites, three or more sites, four or more sites, five or more sites, six or more sites, seven or more sites, eight or more sites, nine or more sites, 10 or more sites, 11 or more sites, 12 or more sites, 13 or more sites, 14 or more sites, or 15 or more sites) of the respective nucleic acid methylation fragment across those nucleic acid methylation fragments in the second training dataset that have the corresponding plurality of CpG sites.

In some such embodiments, the output p-value is between 0.00001 and 0.20. In some embodiments, the output p-value is 0.05. In some such embodiments, the output p-value is between 0.0001 and 0.10. In some such embodiments, the output p-value is between 0.005 and 0.08.

In some embodiments, the respective nucleic acid methylation fragment fails to satisfy a selection criterion in the one or more selection criteria when the respective nucleic acid methylation fragment has less than a threshold number of CpG sites. In some such embodiments, the threshold number of CpG sites is 3, 4, 5, 6, 7, 8, 9, 10, 11, 12, 13, 14, or 15.

In some embodiments, the respective nucleic acid methylation fragment fails to satisfy a selection criterion in the one or more selection criteria when the respective nucleic acid methylation fragment has less than a threshold number of residues. In some embodiments, the threshold number of residues is 32 or 64. In some embodiments, the threshold number of residues is a fixed value between 20 and 90.

In some embodiments, the filtering removes a nucleic acid methylation fragment in the plurality of nucleic acid methylation fragments that has the same corresponding methylation pattern and the same corresponding nucleic acid sequence as another nucleic acid methylation fragment in the plurality of nucleic acid methylation fragments. In some embodiments, the filtering retains a nucleic acid methylation fragment in the plurality of nucleic acid methylation fragments that has the same corresponding methylation pattern and a different corresponding nucleic acid sequence as another nucleic acid methylation fragment in the plurality of nucleic acid methylation fragments. In some embodiments, the filtering retains a nucleic acid methylation fragment in the plurality of nucleic acid methylation fragments that has a different corresponding methylation pattern and a same corresponding nucleic acid sequence as another nucleic acid methylation fragment in the plurality of nucleic acid methylation fragments.

In some embodiments, the nucleic acid methylation fragment fails to satisfy a selection criterion in the one or more selection criteria when the respective nucleic acid methylation fragment has less than a threshold number of CpG sites, the obtaining the dataset pads each nucleic acid methylation fragment in the corresponding plurality of nucleic acid methylation fragments that is less than a predetermined length to be the predetermined length prior to training the autoencoder, and the obtaining the dataset truncates each respective nucleic acid methylation fragment in the corresponding plurality of nucleic acid methylation fragment that is greater than the predetermined length by windowing across the respective nucleic acid methylation fragment with a predetermined stride, thereby breaking the respective nucleic acid methylation fragment into two or more sequence segments, where the two or more nucleic acid methylation fragments each have at least the predetermined length, each have at least the threshold number of CpG sites, and collectively replace the respective nucleic acid methylation fragment in the corresponding plurality of nucleic acid methylation fragments as input to the training the autoencoder.

In some embodiments, the stride is between 90 and 300 nucleotides. In some embodiments, the stride is 100, 128, or 256 nucleotides.

In some embodiments, the obtaining truncates a first nucleic acid methylation fragment in the corresponding plurality of nucleic acid methylation fragment, which is longer than a predetermined length, at a site of variance, conflicting methylation call, or ambiguous call within the first nucleic acid methylation fragment, thereby shortening the first nucleic acid methylation fragment to terminate at the site.

In some embodiments, the autoencoder is a variational autoencoder, a stacked denoising deep autoencoder, a deep recurrent autoencoder, a convolutional autoencoder, or a transformer network.

In some embodiments, the autoencoder is a deep recurrent autoencoder and the training the autoencoder, for a respective sequence read in a corresponding plurality of sequence reads in the first training dataset feeds a first track of the deep recurrent autoencoder the corresponding nucleic acid sequence of the respective nucleic acid methylation fragment broken up into a plurality of k-mers, and feeds a second track of the deep recurrent autoencoder the corresponding methylation pattern of the respective nucleic acid methylation fragment.

In some embodiments, the autoencoder is a deep recurrent autoencoder and the training, for a respective nucleic acid methylation fragment in a corresponding plurality of nucleic acid methylation fragments in the first training dataset, feeds a first track of the deep recurrent autoencoder the corresponding nucleic acid sequence of the respective nucleic acid methylation fragment on a residue basis, and feeds a second track of the deep recurrent autoencoder the corresponding methylation pattern of the respective nucleic acid methylation fragment.

In some embodiments, the training comprises evaluating the first error function for an error in the reconstruction by the autoencoder in accordance with a gradient descent algorithm.

In some embodiments, the encoder encodes the corresponding methylation pattern and the corresponding nucleic acid sequence of the corresponding nucleic acid methylation fragment in each corresponding plurality of nucleic acid methylation fragments in the first training dataset thereby forming a plurality of latent features; and the decoder decodes the plurality of latent features into a reconstruction of the corresponding methylation pattern and the corresponding nucleic acid sequence of the corresponding nucleic acid methylation fragment.

In some embodiments, the supervised model is a logistic regression model.

In some embodiments, the supervised model is a neural network algorithm, a support vector machine algorithm, a Naive Bayes algorithm, a nearest neighbor algorithm, a boosted trees algorithm, a random forest algorithm, a decision tree algorithm, a multinomial logistic regression algorithm, a linear model, or a linear regression algorithm.

In some embodiments, the supervised model uses (i) the methylation pattern of each respective nucleic acid methylation fragment in the plurality of features across the first and second plurality of training subjects and (ii) an indication for each respective nucleic acid methylation fragment as to whether the nucleic acid methylation fragment originates from a training subject with the first cancer state or a training subject with the second cancer state.

In some embodiments, the using the plurality of features comprises using the corresponding score of each feature in the plurality of features to compute a corresponding CpG average reconstruction score for each CpG site in a second plurality of CpG sites found in the plurality of features, thereby computing a plurality of corresponding CpG average reconstruction scores. In some such embodiments, the using the plurality of features further comprises using the plurality of corresponding CpG average reconstruction scores to select low noise regions in a reference genome, regions of a reference genome for targeted sequencing, or regions of the reference genome that are informative for discriminating between cancer states (e.g., the first cancer state and the second cancer state.

In some embodiments, the using the second training dataset and the trained autoencoder selects a methylation pattern associated with a corresponding score on the basis that it is in the top N corresponding score achieved by the using as a feature in the plurality of features. In some such embodiments, N is an integer between 100 and 2000. In some embodiments, N is 1000.

In some embodiments, the corresponding score for the respective nucleic acid methylation fragment is constrained to be a real value between a first number and a second number. In some embodiments, the first number is zero and the second number is one.

In some embodiments, the supervised model is a Kullback-Leibler distance between a first distribution and a second distribution, in which the first distribution comprises a first plurality of corresponding scores for the plurality of features across the nucleic acid methylation fragments of the first training dataset or the second training dataset and the second distribution comprises a second plurality of corresponding scores for a plurality of nucleic acid methylation fragments obtained from a biological sample of a test subject.

In some embodiments, the methylation state of a respective CpG site in the corresponding plurality of CpG sites in the respective nucleic acid methylation fragment is methylated when the respective CpG site is determined by the methylation sequencing to be methylated, unmethylated when the respective CpG site is determined by the methylation sequencing to not be methylated, and flagged as "other" when the methylation sequencing is unable to call the methylation state of the respective CpG site as methylation or unmethylated.

In some embodiments, the methylation sequencing is i) whole-genome methylation sequencing or ii) targeted DNA methylation sequencing using a plurality of nucleic acid probes. In some embodiments, the methylation sequencing detects one or more 5-methylcytosine (5mC) and/or 5-hydroxymethylcytosine (5hmC) in respective nucleic acid methylation fragments. In some embodiments, the methylation sequencing of nucleic acids comprises conversion of one or more unmethylated cytosines or one or more methylated cytosines, in respective nucleic acid methylation fragments, to a corresponding one or more uracils. In some embodiments, the one or more uracils are detected during the methylation sequencing as one or more corresponding thymines. In some embodiments, the conversion of one or more unmethylated cytosines or one or more methylated cytosines comprises a chemical conversion, an enzymatic conversion, or combinations thereof.

In some embodiments, the first cancer state is absence of cancer. In some embodiments, the second cancer state is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof. In some embodiments, the first cancer state is a first stage of a specified cancer, and the second cancer state is a second stage of the specified cancer. In some embodiments, the specified cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof. In some embodiments, the second cancer state is a stage of adrenal cancer, a stage of biliary tract cancer, a stage of bladder cancer, a stage of bone/bone marrow cancer, a stage of brain cancer, a stage of breast cancer, a stage of cervical cancer, a stage of colorectal cancer, a stage of cancer of the esophagus, a stage of gastric cancer, a stage of head/neck cancer, a stage of hepatobiliary cancer, a stage of kidney cancer, a stage of liver cancer, a stage of lung cancer, a stage of ovarian cancer, a stage of pancreatic cancer, a stage of pelvis cancer, a stage of pleura cancer, a stage of prostate cancer, a stage of renal cancer, a stage of skin cancer, a stage of stomach cancer, a stage of testis cancer, a stage of thymus cancer, a stage of thyroid cancer, a stage of uterine cancer, a stage of lymphoma, a stage of melanoma, a stage of multiple myeloma, or a stage of leukemia.

In some embodiments, the methylation sequencing of nucleic acids in a biological sample obtained from the respective subject is methylation sequencing of cell-free nucleic acids in the biological sample. In some embodiments, the biological sample is a blood sample. In some embodiments, the biological sample comprises blood, whole blood, plasma, serum, urine, cerebrospinal fluid, fecal, saliva, sweat, tears, pleural fluid, pericardial fluid, or peritoneal fluid of the test subject. In some embodiments, the respective biological sample is homogenous for the first cancer state. In some embodiments, the respective biological sample is a tumor sample that is homogenous for the first cancer state.

In some embodiments, the method further comprises obtaining a test dataset, in electronic form, where the test dataset comprises, for a test subject, a corresponding methylation pattern and a corresponding nucleic acid sequence of each respective nucleic acid methylation fragment in a plurality of test nucleic acid methylation fragments determined by a methylation sequencing of nucleic acids in a biological sample obtained from the test subject. The corresponding methylation pattern comprises a methylation state of each respective CpG site in a corresponding plurality of CpG sites (e.g., two or more sites, three or more sites, four or more sites, five or more sites, six or more sites, seven or more sites, eight or more sites, nine or more sites, 10 or more sites, 11 or more sites, 12 or more sites, 13 or more sites, 14 or more sites, or 15 or more sites) in the respective test nucleic acid methylation fragment. All or a portion of the test dataset is applied to the supervised model thereby obtaining a determination, from the supervised model, as to whether the test subject has the first or second cancer state.

In some embodiments, the corresponding score is computed using the first error function. In some embodiments, the corresponding score for a respective nucleic acid methylation fragment is computed using a second error function that is different than the first error function.

In some embodiments, the corresponding score for a respective nucleic acid methylation fragment is computed as $A(f)=Loss(f, f')$ where f is the corresponding methylation pattern of the respective nucleic acid methylation fragment, f' is a reconstruction of the corresponding methylation pattern of the respective nucleic acid methylation fragment by the autoencoder upon inputting the corresponding methylation pattern and the corresponding nucleic acid sequence of the respective nucleic acid methylation fragment into the autoencoder, and Loss is a loss between f and f'. In some such embodiments, Loss is a reconstruction error between f and f', a Hamming distance between f and f', a cross entropy loss between f and f', a mean squared error between f and f', or a mean absolute error between f and f'.

In some embodiments, the corresponding score for a respective nucleic acid methylation fragment is computed as $A(f)=w_1*Loss(f, f')+w_2*Distance[E(f), E(f\_NC)]$ where $w_1$ is a first weight, f is the corresponding methylation pattern of the respective nucleic acid methylation fragment, f' is a reconstruction of the corresponding methylation pattern of the respective nucleic acid methylation fragment by the autoencoder upon inputting the corresponding methylation pattern and the corresponding nucleic acid sequence of the respective nucleic acid methylation fragment into the autoencoder, $w_2$ is a second weight, Loss is a loss between f and f', E(f) is an encoding produced by the autoencoder upon inputting the corresponding methylation pattern of the respective nucleic acid methylation fragment into the autoencoder, f_NC is a methylation pattern and nucleic acid sequence of a nucleic acid methylation fragment that localizes to the same genomic location as the respective nucleic acid methylation fragment and has the same sequence as the respective nucleic acid methylation fragment, E(f_NC) is an encoding produced by the autoencoder upon inputting f_NC into the autoencoder, and Distance is a distance measure or a similarity measure (e.g., cosine distance, Euclidian distance, Manhattan distance, Jaccard distance, correlation distance, Chi-square distance, or Mahalanobis distance) between E(f) and E(f_NC). In some embodiments, $w_1$ and $w_2$ each have a value of 1. In some alternative embodiments, $w_1$ and $w_2$ each have a different value.

In some embodiments, the error calculated for the trained autoencoder across the first training dataset satisfies an error threshold. In some embodiments, the error calculated by the first error function across the first training dataset satisfies an error threshold when the error is less than 15 percent, less than 10 percent, less than five percent, less than four percent, or less than three percent. In some embodiments the first training dataset or the second training dataset comprises a first corresponding nucleic acid sequence of a first nucleic acid methylation fragment in the corresponding plurality of nucleic acid methylation fragments determined by the methylation sequencing of nucleic acids in the biological sample obtained from the respective training subject. In some embodiments, the first corresponding nucleic acid sequence is from a forward strand or a reverse strand of the first nucleic acid methylation fragment. In some embodiments, the first corresponding nucleic acid sequence is a reverse strand of the first nucleic acid methylation fragment and is in reverse complement form or is flagged as being reverse strand of the first nucleic acid methylation fragment.

Another aspect of the present disclosure provides a method of forming a classifier for detecting a cancer state. The method is performed at a computer system comprising at least one processor and a memory storing at least one program for execution by the at least one processor. The at least one program comprises instructions for obtaining a training dataset, in electronic form. The training dataset comprises, for each respective training subject in a plurality of training subjects, a corresponding methylation pattern and a corresponding nucleic acid sequence of each respective nucleic acid methylation fragment in a corresponding plurality of nucleic acid methylation fragments determined by a methylation sequencing of nucleic acids in a biological sample obtained from the respective training subject. The corresponding methylation pattern comprises a methylation state of each respective CpG site in a corresponding plurality of CpG sites in the respective nucleic acid methylation fragment. Each training subject in the plurality of training subjects has the cancer state.

The at least one program further comprises instructions for training an untrained autoencoder, where the autoencoder includes an encoder and a decoder, using the corresponding methylation pattern and the corresponding nucleic acid sequence of each respective nucleic acid methylation fragment in each corresponding plurality of nucleic acid methylation fragments in the training dataset as input. The training comprises, for each corresponding nucleic acid sequence of each respective nucleic acid methylation fragment in each corresponding plurality of nucleic acid methylation fragments in the training dataset, evaluating a first error function for an error in the reconstruction by the autoencoder of the corresponding methylation pattern and the corresponding nucleic acid sequence of the corresponding nucleic acid methylation fragment, thereby forming a trained autoencoder.

In some embodiments, the at least one program further comprises instructions for obtaining a test dataset, in electronic form. The test dataset comprises, for a test subject, a corresponding methylation pattern and a corresponding nucleic acid sequence of each respective test nucleic acid methylation fragment in a plurality of test nucleic acid methylation fragments determined by a methylation sequencing of nucleic acids in a biological sample obtained from the test subject. The corresponding methylation pattern comprises a methylation state of each respective CpG site in a corresponding plurality of CpG sites in the respective test nucleic acid methylation fragment. All or a portion of the test dataset is applied to the trained autoencoder to determine whether the test subject has the cancer state, where the applying computes, for each respective test nucleic acid methylation fragment in the plurality of test nucleic acid methylation fragments in the test dataset, a corresponding score determined at least in part by a reconstruction of the corresponding methylation pattern of the respective nucleic acid methylation fragment by the trained autoencoder upon inputting the corresponding methylation pattern and the corresponding nucleic acid sequence of the respective test nucleic acid methylation fragment into the autoencoder.

Another aspect of the present disclosure provides a method of detecting a cancer state. The method is performed at a computer system comprising at least one processor and a memory storing at least one program for execution by the at least one processor. The at least one program comprises instructions for obtaining a test dataset in electronic form. The test dataset comprises, for a test subject, a corresponding methylation pattern and a corresponding nucleic acid sequence of each respective nucleic acid methylation fragment in a plurality of nucleic acid methylation fragments determined by a methylation sequencing of nucleic acids in a biological sample obtained from the test subject. The corresponding methylation pattern comprises a methylation state of each respective CpG site in a corresponding plurality of CpG sites in the respective nucleic acid methylation fragment.

The method further comprises applying the corresponding methylation pattern and the corresponding nucleic acid sequence of each respective nucleic acid methylation fragment in all or a portion of the plurality of nucleic acid methylation fragments to a trained autoencoder to determine whether the test subject has the cancer state. In so doing, there is computed, for each respective nucleic acid methylation fragment in the all or the portion of the plurality of nucleic acid methylation fragments, a corresponding score determined at least in part by a reconstruction of the corresponding methylation pattern of the respective nucleic acid methylation fragment by the trained autoencoder upon inputting the corresponding methylation pattern and the corresponding nucleic acid sequence of the respective nucleic acid methylation fragment into the trained autoencoder.

Another aspect of the present disclosure provides a computer system for discriminating a cancer state. The computer system comprises at least one processor and a memory storing at least one program for execution by the at least one processor. The at least one program comprises instructions for discriminating a cancer state. In some embodiments, the at least one program comprises instructions for performing any of the methods and embodiments disclosed herein, and/or any combinations thereof as will be apparent to one skilled in the art. In some embodiments, the at least one program is configured for execution by a computer.

Another aspect of the present disclosure provides a non-transitory computer-readable storage medium having stored thereon program code instructions that, when executed by a processor, cause the processor to perform a method of discriminating a cancer state. In some embodiments, the program code instructions comprise instructions for performing any of the methods and embodiments disclosed herein, and/or any combinations thereof. In some embodiments, the program code instructions are configured for execution by a computer or a computer system.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIG. 3 is a block diagram illustrating an example of a method for obtaining and preprocessing a dataset in accordance with some embodiments of the present disclosure.

FIG. 4 illustrates a method of applying a first threshold filter to the methylation pattern of each respective fragment in a plurality of fragments in accordance with some embodiments of the present disclosure.

FIGS. 5A, 5B, 5C, 5D, and 5E collectively illustrate an example flowchart of a method for discriminating between two cancer states in accordance with some embodiments of the present disclosure.

DETAILED DESCRIPTION

Figure 1:
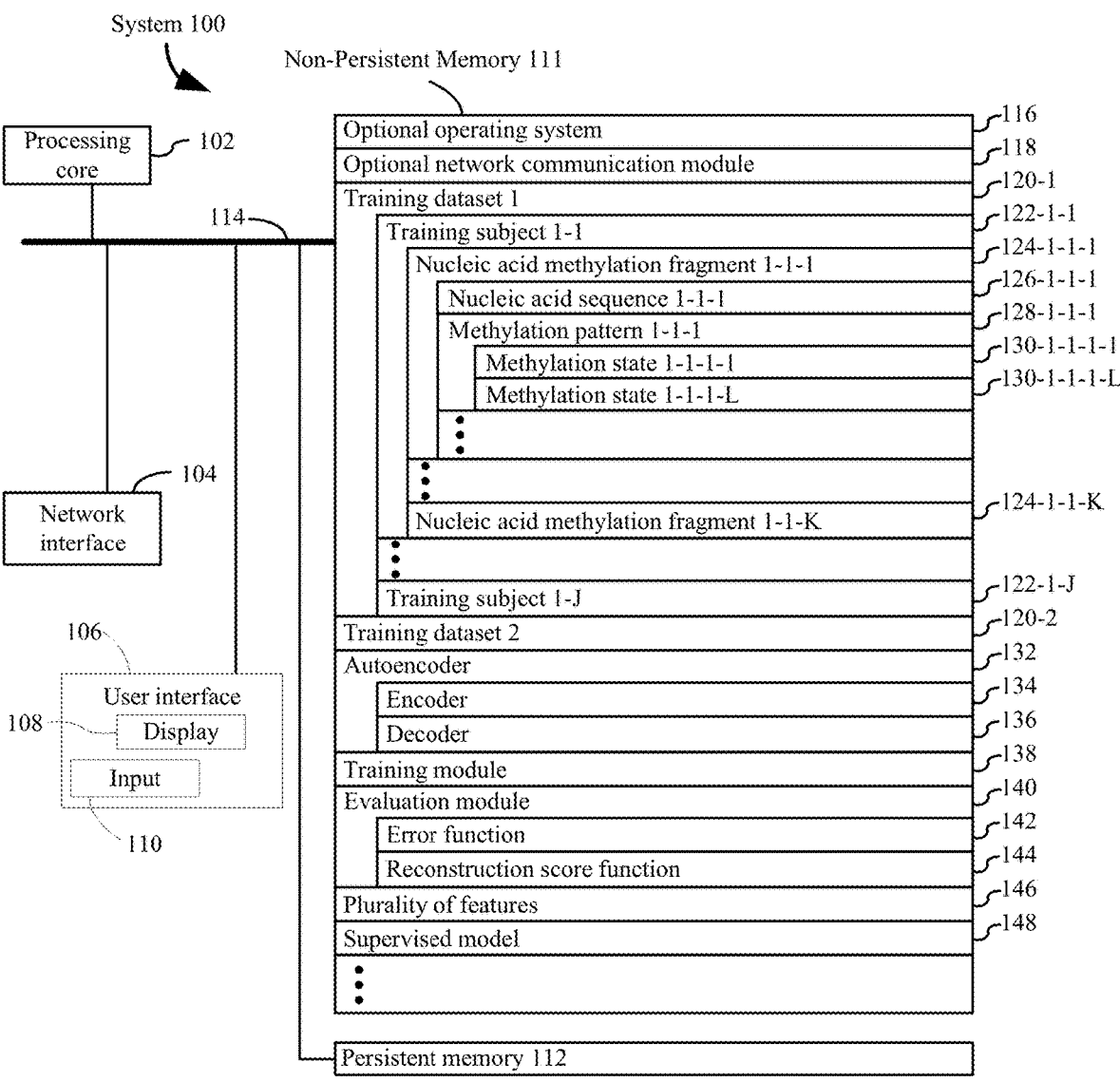
FIG. 1 is a block diagram illustrating an example of a computing system in accordance with some embodiments of the present disclosure.

One approach to handling the complexity of the search for biomarkers when using large-scale nucleic acid sequencing (e.g., methylation sequencing for detection of diseases such as cancer) is deep learning. Deep learning holds promise for using such biomarkers to model and infer complex biological patterns and non-linearities across the genome, and thus develop diagnostic tests for cancer.

Deep learning strategies using nucleic acid sequence data (e.g., nucleic acid methylation fragments) can be performed for various objectives relating to cancer, including classification, regression, inference and clustering. In particular, one method for classification of cancer is performed using a supervised or semi-supervised model, in which the model is trained using training samples labeled with one or more conditions of interest. The trained model can then be used to discriminate between a number of learned conditions, for a given test sample, thus classifying the test sample. See, for example, U.S. patent application Ser. No. 17/119,606, filed Dec. 11, 2020, the content of which is hereby incorporated herein by reference in its entirety.

Along with the promise and possibilities of applying deep learning to nucleic acid sequence data, there are numerous caveats and dangers to avoid, including large class imbalance due to low prevalence of cancer in a general population, insufficient number of training examples relative to the number of learned parameters, and susceptibility to overfit on biological or process-related noise, among others. For example, sample quality and/or purity in training datasets may vary due to the inclusion of mixed sample types, resulting in poor classifier performance (e.g., when using cell-free DNA from liquid biopsies, which can be derived from multiple cell and/or tissue origins). Obtaining a sufficient number of high-quality training samples that can be confidently annotated with the conditions of interest (e.g., cancer, non-cancer and/or cancer subtype) for accurate training of a classifier therefore presents a challenge.

One method for identifying such high-quality training samples is unsupervised anomaly detection, in which one or more unknown samples from a test dataset are assessed against a learned representation of a reference dataset (e.g., a distribution of data points from the reference dataset). Learned representations can be obtained by training an artificial neural network such as an autoencoder on a dataset of training samples from the reference condition of interest.

Provided herein are systems and methods for cancer condition determination using autoencoders to perform unsupervised anomaly detection and, thus, feature detection.

The present disclosure provides improved systems and methods for identifying anomalous training samples in training datasets, thus eliminating uninformative training samples that are representative of a reference dataset having a first condition of interest (e.g., healthy and/or normal) and generating a curated training dataset comprising discriminative features specific to a second condition of interest (e.g., cancer). As an example, anomalous methylation patterns can be identified using methylation fragment reconstruction scores (MFRS).

In some aspects, the systems and methods disclosed herein identify anomalous training samples concurrently with or independent of specific feature selection filters (e.g., percentage of methylation level) that can overlook non-linear or otherwise complex patterns with subtle differentiating characteristics between nucleic acid sequences from distinct origins. Such differentiating or discriminative features are subsequently used to train a classifier to discriminate between cancer conditions.

In some alternative aspects, the systems and methods disclosed herein provide a learned representation of a first condition of interest (e.g., healthy and/or normal) that can be used as a one-class classifier (e.g., a unary classifier) to identify the presence or absence of the first condition of interest (e.g., normal or abnormal).

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Definitions

As used herein, the term "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of $\pm 20\%$, $\pm 10\%$, $\pm 5\%$, or $\pm 1\%$ of a given value. The term "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to $\pm 10\%$. The term "about" can refer to $\pm 5\%$.

As used herein, the term "biological sample," "patient sample," or "sample" refers to any sample taken from a subject, which can reflect a biological state associated with the subject, and that includes cell-free DNA. Examples of biological samples include, but are not limited to, blood, whole blood, plasma, serum, urine, cerebrospinal fluid, fecal, saliva, sweat, tears, pleural fluid, pericardial fluid, or peritoneal fluid of the subject. A biological sample can include any tissue or material derived from a living or dead subject. A biological sample can be a cell-free sample. A biological sample can comprise a nucleic acid (e.g., DNA or RNA) or a fragment thereof. The term "nucleic acid" can refer to deoxyribonucleic acid (DNA), ribonucleic acid (RNA) or any hybrid or fragment thereof. The nucleic acid in the sample can be a cell-free nucleic acid. A sample can be a liquid sample or a solid sample (e.g., a cell or tissue sample). A biological sample can be a bodily fluid, such as blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. A biological sample can be a stool sample. In various embodiments, the majority of DNA in a biological sample that has been enriched for cell-free DNA (e.g., a plasma sample obtained via a centrifugation protocol) can be cell-free (e.g., greater than 50%, 60%, 70%, 80%, 90%, 95%, or 99% of the DNA can be cell-free). A biological sample can be treated to physically disrupt tissue or cell structure (e.g., centrifugation and/or cell lysis), thus releasing intracellular components into a solution which can further contain enzymes, buffers, salts, detergents, and the like which can be used to prepare the sample for analysis.

As used herein, the term "cancer" or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well-differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites.

As used herein, the term "cancer condition" refers to a condition of a sample relative to cancer, wherein each potential characteristic and/or measure of the condition refers to a "state" of the cancer condition. For example, a sample can have a cancer condition that is "cancer" or "non-cancer." Alternatively, a cancer condition can be a primary site of origin or a tissue-of-origin, such as breast cancer, lung cancer, prostate cancer, colorectal cancer, renal cancer, uterine cancer, pancreatic cancer, cancer of the esophagus, a lymphoma, head/neck cancer, ovarian cancer, a hepatobiliary cancer, a melanoma, cervical cancer, multiple myeloma, leukemia, thyroid cancer, bladder cancer, and gastric cancer. A cancer condition can be a cancer type or a tumor of a certain cancer type, or a fraction thereof, such as an adrenocortical carcinoma, a childhood adrenocortical carcinoma, a tumor of an AIDS-related cancer, kaposi sarcoma, a tumor associated with anal cancer, a tumor associated with an appendix cancer, an astrocytoma, a childhood (brain cancer) tumor, an atypical teratoid/rhabdoid tumor, a central nervous system (brain cancer) tumor, a basal cell carcinoma of the skin, a tumor associated with bile duct cancer, a bladder cancer tumor, a childhood bladder cancer tumor, a bone cancer (e.g., ewing sarcoma and osteosarcoma and malignant fibrous histiocytoma) tissue, a brain tumor, breast cancer tissue, childhood breast cancer tissue, a childhood bronchial tumor, burkitt lymphoma tissue, a carcinoid tumor (gastrointestinal), a childhood carcinoid tumor, a carcinoma of unknown primary, a childhood carcinoma of unknown primary, a childhood cardiac (heart) tumor, a central nervous system (e.g., brain cancer such as childhood atypical teratoid/rhabdoid) tumor, a childhood embryonal tumor, a childhood germ cell tumor, cervical cancer tissue, childhood cervical cancer tissue, cholangiocarcinoma tissue, childhood chordoma tissue, a chronic myeloproliferative neoplasm, a colorectal cancer tumor, a childhood colorectal cancer tumor, childhood craniopharyngioma tissue, a ductal carcinoma in situ (DCIS), a childhood embryonal tumor, endometrial cancer (uterine cancer) tissue, childhood ependymoma tissue, esophageal cancer tissue, childhood esophageal cancer tissue, esthesioneuroblastoma (head and neck cancer) tissue, a childhood extracranial germ cell tumor, an extragonadal germ cell tumor, eye cancer tissue, an intraocular melanoma, a retinoblastoma, fallopian tube cancer tissue, gallbladder cancer tissue, gastric (stomach) cancer tissue, childhood gastric (stomach) cancer tissue, a gastrointestinal carcinoid tumor, a gastrointestinal stromal tumor (GIST), a childhood gastrointestinal stromal tumor, a germ cell tumor (e.g., a childhood central nervous system germ cell tumor, a childhood extracranial germ cell tumor, an extragonadal germ cell tumor, an ovarian germ cell tumor, or testicular cancer tissue), head and neck cancer tissue, a childhood heart tumor, hepatocellular cancer (HCC) tissue, an islet cell tumor (pancreatic neuroendocrine tumors), kidney or renal cell cancer (RCC) tissue, laryngeal cancer tissue, leukemia, liver cancer tissue, lung cancer (non-small cell and small cell) tissue, childhood lung cancer tissue, male breast cancer tissue, a malignant fibrous histiocytoma of bone and osteosarcoma, a melanoma, a childhood melanoma, an intraocular melanoma, a childhood intraocular melanoma, a merkel cell carcinoma, a malignant mesothelioma, a childhood mesothelioma, metastatic cancer tissue, metastatic squamous neck cancer with occult primary tissue, a midline tract carcinoma with NUT gene changes, mouth cancer (head and neck cancer) tissue, multiple endocrine neoplasia syndrome tissue, a multiple myeloma/plasma cell neoplasm, myelodysplastic syndrome tissue, a myelodysplastic/myeloproliferative neoplasm, a chronic myeloproliferative neoplasm, nasal cavity and paranasal sinus cancer tissue, nasopharyngeal cancer (NPC) tissue, neuroblastoma tissue, non-small cell lung cancer tissue, oral cancer tissue, lip and oral cavity cancer and oropharyngeal cancer tissue, osteosarcoma and malignant fibrous histiocytoma of bone tissue, ovarian cancer tissue, childhood ovarian cancer tissue, pancreatic cancer tissue, childhood pancreatic cancer tissue, papillomatosis (childhood laryngeal) tissue, paraganglioma tissue, childhood paraganglioma tissue, paranasal sinus and nasal cavity cancer tissue, parathyroid cancer tissue, penile cancer tissue, pharyngeal cancer tissue, pheochromocytoma tissue, childhood pheochromocytoma tissue, a pituitary tumor, a plasma cell neoplasm/multiple myeloma, a pleuropulmonary blastoma, a primary central nervous system (CNS) lymphoma, primary peritoneal cancer tissue, prostate cancer tissue, rectal cancer tissue, a retinoblastoma, a childhood rhabdomyosarcoma, salivary gland cancer tissue, a sarcoma (e.g., a childhood vascular tumor, osteosarcoma, uterine sarcoma, etc.), Sézary syndrome (lymphoma) tissue, skin cancer tissue, childhood skin cancer tissue, small cell lung cancer tissue, small intestine cancer tissue, a squamous cell carcinoma of the skin, a squamous neck cancer with occult primary, a cutaneous t-cell lymphoma, testicular cancer tissue, childhood testicular cancer tissue, throat cancer (e.g., nasopharyngeal cancer, oropharyngeal cancer, hypopharyngeal cancer) tissue, a thymoma or thymic carcinoma, thyroid cancer tissue, transitional cell cancer of the renal pelvis and ureter tissue, unknown primary carcinoma tissue, ureter or renal pelvis tissue, transitional cell cancer (kidney (renal cell) cancer tissue, urethral cancer tissue, endometrial uterine cancer tissue, uterine sarcoma tissue, vaginal cancer tissue, childhood vaginal cancer tissue, a vascular tumor, vulvar cancer tissue, a Wilms tumor or other childhood kidney tumor. A cancer condition can be a stage of cancer, such as a predetermined stage of a breast cancer, a predetermined stage of a lung cancer, a predetermined stage of a prostate cancer, a predetermined stage of a colorectal cancer, a predetermined stage of a renal cancer, a predetermined stage of a uterine cancer, a predetermined stage of a pancreatic cancer, a predetermined stage of a cancer of the esophagus, a predetermined stage of a lymphoma, a predetermined stage of a head/neck cancer, a predetermined stage of a ovarian cancer, a predetermined stage of a hepatobiliary cancer, a predetermined stage of a melanoma, a predetermined stage of a cervical cancer, a predetermined stage of a multiple myeloma, a predetermined stage of a leukemia, a predetermined stage of a thyroid cancer, a predetermined stage of a bladder cancer, or a predetermined stage of a gastric cancer. A cancer condition can also be a survival metric, which can be a predetermined likelihood of survival for a predetermined period of time. Multiple samples from a single subject can have different cancer conditions or the same cancer condition. Multiple subjects can have different cancer conditions or the same cancer condition.

As used herein, Circulating Cell-free Genome Atlas or "CCGA" is defined as an observational clinical study that prospectively collects blood and tissue from newly diagnosed cancer patients as well as blood only from subjects who do not have a cancer diagnosis. The purpose of the study is to develop a pan-cancer classifier that distinguishes cancer from non-cancer and identifies tissue of origin. Example 1 provides further details of the CCGA dataset.

The term "classification" refers to any number(s) or other characters(s) that are associated with a particular property of a sample. For example, a "+" symbol (or the word "positive") can signify that a sample is classified as having deletions or amplifications. In another example, the term "classification" can refer to an amount of tumor tissue in the subject and/or sample, a size of the tumor in the subject and/or sample, a stage of the tumor in the subject, a tumor load in the subject and/or sample, and presence of tumor metastasis in the subject. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

As used herein, the terms "cell-free nucleic acid," "cell-free DNA," and "cfDNA" interchangeably refers to nucleic acid molecules that can be found outside cells, in bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids are used interchangeably as circulating nucleic acids. Examples of the cell-free nucleic acids include but are not limited to RNA, mitochondrial DNA, or genomic DNA. Cell-free nucleic acid originates from one or more healthy cells and/or from one or more cancer cells.

As used herein, the term "cell-free nucleic acids" refers to nucleic acid molecules that can be found outside cells, in bodily fluids such as blood, whole blood, plasma, serum, urine, cerebrospinal fluid, fecal, saliva, sweat, sweat, tears, pleural fluid, pericardial fluid, or peritoneal fluid of a subject. Cell-free nucleic acids originate from one or more healthy cells and/or from one or more cancer cells Cell-free nucleic acids are used interchangeably as circulating nucleic acids. Examples of the cell-free nucleic acid include but are not limited to RNA, mitochondrial DNA, or genomic DNA.

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of a constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the phrase "healthy," refers to a subject possessing good health. A healthy subject can demonstrate an absence of any malignant or non-malignant disease. A "healthy individual" can have other diseases or conditions, unrelated to the condition being assayed, which can normally not be considered "healthy."

As used herein, the term "methylation" refers to a modification of deoxyribonucleic acid (DNA) where a hydrogen atom on the pyrimidine ring of a cytosine base is converted to a methyl group, forming 5-methylcytosine. In particular, methylation tends to occur at dinucleotides of cytosine and guanine referred to herein as "CpG sites". In other instances, methylation may occur at a cytosine not part of a CpG site or at another nucleotide that's not cytosine; however, these are rarer occurrences. In this present disclosure, methylation is discussed in reference to CpG sites for the sake of clarity. Anomalous cfDNA methylation can be identified as hypermethylation or hypomethylation, both of which may be indicative of cancer status. As is well known in the art, DNA methylation anomalies (compared to healthy controls) can cause different effects, which may contribute to cancer.

Various challenges arise in the identification of anomalously methylated cfDNA fragments. First, determining a subject's cfDNA to be anomalously methylated only holds weight in comparison with a group of control subjects, such that if the control group is small in number, the determination loses confidence with the small control group. Additionally, among a group of control subjects' methylation status can vary which can be difficult to account for when determining a subject's cfDNA to be anomalously methylated. On another note, methylation of a cytosine at a CpG site causally influences methylation at a subsequent CpG site.

The principles described herein are equally applicable for the detection of methylation in a non-CpG context, including non-cytosine methylation. Further, the methylation state vectors may contain elements that are generally vectors of sites where methylation has or has not occurred (even if those sites are not CpG sites specifically). With that substitution, the remainder of the processes described herein are the same, and consequently, the inventive concepts described herein are applicable to those other forms of methylation.

As used herein, the term "methylation pattern" refers to a sequence of methylation states (e.g., a methylation state vector) for one or more CpG sites. Methylation states include, but are not limited to, methylated (e.g., represented as "M") and unmethylated (e.g., represented as "U"). For example, a methylation pattern spanning 5 CpG sites may be represented as "MMMMM" or "UUUUU", where each discrete symbol represents a methylation state at a single CpG site. A methylation pattern may or may not correspond to a specific genomic location and/or a specific one or more CpG sites in a reference genome.

As used herein a "methylome" can be a measure of an amount of DNA methylation at a plurality of sites or loci in a genome. The methylome can correspond to all of a genome, a substantial part of a genome, or relatively small portion(s) of a genome. A "tumor methylome" can be a methylome of a tumor of a subject (e.g., a human). A tumor methylome can be determined using tumor tissue or cell-free tumor DNA in plasma. A tumor methylome can be one example of a methylome of interest. A methylome of interest can be a methylome of an organ that can contribute nucleic acid, e.g., DNA into a bodily fluid (e.g., a methylome of brain cells, a bone, lungs, heart, muscles, kidneys, etc.). The organ can be a transplanted organ.

As used herein, the terms "nucleic acid" and "nucleic acid molecule" are used interchangeably. The terms refer to nucleic acids of any composition form, such as deoxyribo-nucleic acid (DNA, e.g., complementary DNA (cDNA), genomic DNA (gDNA) and the like), and/or DNA analogs (e.g., containing base analogs, sugar analogs and/or a non-native backbone and the like), all of which can be in single- or double-stranded form. Unless otherwise limited, a nucleic acid can comprise known analogs of natural nucleotides, some of which can function in a similar manner as naturally occurring nucleotides. A nucleic acid molecule can be in any form useful for conducting processes herein (e.g., linear, circular, supercoiled, single-stranded, double-stranded and the like). A nucleic acid in some embodiments can be from a single chromosome or fragment thereof (e.g., a nucleic acid sample may be from one chromosome of a sample obtained from a diploid organism). In certain embodiments, nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with proteins or other molecules. Nucleic acids also include derivatives, variants and analogs of DNA synthesized, replicated or amplified from single-stranded ("sense" or "antisense," "plus" strand or "minus" strand, "forward" reading frame or "reverse" reading frame) and double-stranded polynucleotides. Deoxyribonucleotides include deoxyadenosine, deoxycytidine, deoxyguanosine, and deoxythymidine. A nucleic acid may be prepared using a nucleic acid obtained from a subject as a template.

As used herein, the term "reference genome" refers to any particular known, sequenced or characterized genome, whether partial or complete, of any organism or virus that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). In some embodiments, sequence reads (e.g., single-end or paired-end reads) can be generated from one or both strands of a targeted nucleic acid fragment. The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as a DNA fragment.

As used herein the term "sequencing breadth" refers to what fraction of a particular reference genome (e.g., human reference genome) or part of the genome has been analyzed. The denominator of the fraction can be a repeat-masked genome, and thus 100% can correspond to all of the reference genome minus the masked parts. A repeat-masked genome can refer to a genome in which sequence repeats are masked (e.g., sequence reads align to unmasked portions of the genome). Any parts of a genome can be masked, and thus one can focus on any particular part of a reference genome. Broad sequencing can refer to sequencing and analyzing at least 0.1% of the genome.

As used herein, the term "sequencing depth," is interchangeably used with the term "coverage" and refers to the number of times a locus is covered by a consensus sequence read corresponding to a unique nucleic acid target molecule aligned to the locus; e.g., the sequencing depth is equal to the number of unique nucleic acid target molecules covering the locus. The locus can be as small as a nucleotide, or as large as a chromosome arm, or as large as an entire genome. Sequencing depth can be expressed as "Yx", e.g., 50×, 100×, etc., where "Y" refers to the number of times a locus is covered with a sequence corresponding to a nucleic acid target; e.g., the number of times independent sequence information is obtained covering the particular locus. In some embodiments, the sequencing depth corresponds to the number of genomes that have been sequenced. Sequencing depth can also be applied to multiple loci, or the whole genome, in which case Y can refer to the mean or average number of times a loci or a haploid genome, or a whole genome, respectively, is sequenced. When a mean depth is quoted, the actual depth for different loci included in the dataset can span over a range of values. Ultra-deep sequencing can refer to at least 100× in sequencing depth at a locus.

As used herein, the term "subject" refers to any living or non-living organism, including but not limited to a human (e.g., a male human, female human, fetus, pregnant female, child, or the like), a non-human animal, a plant, a bacterium, a fungus or a protist. Any human or non-human animal can serve as a subject, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale, and shark. In some embodiments, a subject is a male or female of any stage (e.g., a man, a woman or a child). A subject from whom a sample is taken, or is treated by any of the methods or compositions described herein can be of any age and can be an adult, infant or child. In some cases, the subject, e.g., patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between about 2 and about 20 years old, between about 20 and about 40 years old, or between about 40 and about 90 years old). A particular class of subjects, e.g., patients that can benefit from a method of the present disclosure is subjects, e.g., subjects over the age of 40, subjects over the age of 45, subjects over the age of 50, subjects over the age of 50, subjects over the age of 55, or subjects over the age of 60.

As used herein, the term "tissue" can correspond to a group of cells that group together as a functional unit. More than one type of cell can be found in a single tissue. Different types of tissue may consist of different types of cells (e.g., hepatocytes, alveolar cells or blood cells), but also can correspond to tissue from different organisms (mother vs. fetus) or to healthy cells vs. tumor cells. The term "tissue" can generally refer to any group of cells found in the human body (e.g., heart tissue, lung tissue, kidney tissue, nasopharyngeal tissue, oropharyngeal tissue). In some aspects, the term "tissue" or "tissue type" can be used to refer to a tissue from which a cell-free nucleic acid originates. In one example, viral nucleic acid fragments can be derived from blood tissue. In another example, viral nucleic acid fragments can be derived from tumor tissue.

As used herein the term "untrained model" (e.g., "untrained classifier" and/or "untrained autoencoder") refers to a machine learning model or algorithm such as a classifier or an autoencoder that has not been trained on a target dataset. In some embodiments, "training a model" refers to the process of training an untrained or partially untrained model. For instance, consider the case of a first canonical set of methylation state vectors (e.g., methylation patterns) and a second canonical set of methylation state vectors discussed below. The respective canonical sets of methylation state vectors are applied as collective input to an untrained classifier, in conjunction with the cell source of each respective reference subject represented by the first canonical set of methylation state vectors (hereinafter "primary training dataset") to train the untrained classifier on cell source thereby obtaining a trained classifier. Moreover, the term "untrained model" does not exclude the possibility that transfer learning techniques are used in such training of the untrained model. For instance, United States Patent Publication No. US 2020-0372296 A1 entitled "Systems and Methods for Determining Whether a Subject Has a Cancer Condition Using Transfer Learning," and Fernandes et al., 2017, "Transfer Learning with Partial Observability Applied to Cervical Cancer Screening," Pattern Recognition and Image Analysis: 8th Iberian Conference Proceedings, 243-250, each of which is hereby incorporated by reference, provide non-limiting examples of such transfer learning. In instances where transfer learning is used, the untrained classifier described above is provided with additional data over and beyond that of the primary training dataset. That is, in non-limiting examples of transfer learning embodiments, the untrained classifier receives (i) canonical sets of methylation state vectors and the cell source labels of each of the reference subjects represented by canonical sets of methylation state vectors ("primary training dataset") and (ii) additional data. Typically, this additional data is in the form of coefficients (e.g., regression coefficients) that were learned from another, auxiliary training dataset. Moreover, while a description of a single auxiliary training dataset has been disclosed, there is no limit on the number of auxiliary training datasets that may be used to complement the primary training dataset in training the untrained model in the present disclosure. For instance, in some embodiments, two or more auxiliary training datasets, three or more auxiliary training datasets, four or more auxiliary training datasets or five or more auxiliary training datasets are used to complement the primary training dataset through transfer learning, where each such auxiliary dataset is different than the primary training dataset. Any manner of transfer learning may be used in such embodiments. For instance, consider the case where there is a first auxiliary training dataset and a second auxiliary training dataset in addition to the primary training dataset. The coefficients learned from the first auxiliary training dataset (by application of a classifier such as regression to the first auxiliary training dataset) may be applied to the second auxiliary training dataset using transfer learning techniques (e.g., the above described two-dimensional matrix multiplication), which in turn may result in a trained intermediate classifier whose coefficients are then applied to the primary training dataset and this, in conjunction with the primary training dataset itself, is applied to the untrained classifier. Alternatively, a first set of coefficients learned from the first auxiliary training dataset (by application of a classifier such as regression to the first auxiliary training dataset) and a second set of coefficients learned from the second auxiliary training dataset (by application of a classifier such as regression to the second auxiliary training dataset) may each individually be applied to a separate instance of the primary training dataset (e.g., by separate independent matrix multiplications) and both such applications of the coefficients to separate instances of the primary training dataset in conjunction with the primary training dataset itself (or some reduced form of the primary training dataset such as principal components or regression coefficients learned from the primary training set) may then be applied to the untrained classifier in order to train the untrained classifier. In either example, knowledge regarding cell source (e.g., cancer type, etc.) derived from the first and second auxiliary training datasets is used, in conjunction with the cell source labeled primary training dataset), to train the untrained model.

The terminology used herein is for the purpose of describing particular cases only and is not intended to be limiting. As used herein, the singular forms "a," "an" and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

Details of an exemplary system are now described in conjunction with FIG. 1. FIG. 1 is a block diagram illustrating a system 100 in accordance with some implementations. The device 100 in some implementations includes at least one or more processing units CPU(s) 102 (also referred to as processors), one or more network interfaces 104, a display 106 having a user interface 108, an input device 110, a memory, and one or more communication buses 114 for interconnecting these components. The one or more communication buses 114 optionally include circuitry (sometimes called a chipset) that interconnects and controls communications between system components. The memory may be a non-persistent memory 111, a persistent memory 112, or any combination thereof. The non-persistent memory 111 typically includes high-speed random access memory, such as DRAM, SRAM, DDR RAM, ROM, EEPROM, flash memory, whereas the persistent memory typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid-state storage devices. Regardless of its specific implementation, the non-persistent memory 111 and/or the persistent memory 112 comprises at least one non-transitory computer-readable storage medium, and it stores thereon computer-executable executable instructions which can be in the form of programs, modules, and data structures.

In some embodiments, as shown in FIG. 1, the non-persistent memory 111 stores the following:

optional instructions, programs, data or information associated with optional operating system 116, which includes procedures for handling various basic system services and for performing hardware-dependent tasks;

optional instructions, programs, data or information associated with optional network communication module (or instructions) 118 for connecting the system 100 with other devices and/or to a communication network;

instructions, programs, data or information associated with training dataset 120 obtained in electronic form (e.g., a first training dataset 120-1 and a second training dataset 120-2);

instructions, programs, data or information associated with a respective plurality of training subjects 122 for each respective training dataset (e.g., a respective first plurality of training subjects 122-1-1, . . . ,122-1-J, where J is a positive integer, for the respective first training dataset), where each training subject in the first plurality of training subjects has a first cancer state and each training subject in the second plurality of training subjects has a second cancer state;

instructions, programs, data or information associated with a plurality of nucleic acid methylation fragments 124 for each respective training subject 122 (e.g., 124-1-1-1, . . . ,124-1-1-K, where K is a positive integer), comprising a corresponding nucleic acid sequence 126 (e.g., 126-1-1-1) and a corresponding methylation pattern 128 (e.g., 128-1-1-1) determined by methylation sequencing of nucleic acids in a biological sample obtained from the respective subject, where the corresponding methylation pattern comprises a methylation state 130 of each respective CpG site in a corresponding plurality of CpG sites in the respective nucleic acid methylation fragment (e.g., 130-1-1-1-1, . . . ,130-1-1-1-L, where L is a positive integer);

instructions, programs, data or information associated with an autoencoder 132 including an encoder 134 that encodes an input (e.g., a corresponding methylation pattern and a corresponding nucleic acid sequence of a corresponding nucleic acid methylation fragment) and a decoder 136 that reconstructs at least a portion of the input (e.g., the corresponding methylation pattern and/or the corresponding nucleic acid sequence of the corresponding nucleic acid methylation fragment), where the autoencoder can be untrained or trained;

instructions, programs, data or information associated with a training module 138 that trains the autoencoder 132 and/or the supervised model 148;

instructions, programs, data or information associated with an evaluation module 140 comprising:

at least one error function 142 that evaluates an error in the reconstruction by the autoencoder 132 of a corresponding methylation pattern 128 and a corresponding nucleic acid sequence 126 of a corresponding nucleic acid methylation fragment 124 (e.g., for each corresponding nucleic acid sequence of each respective nucleic acid methylation fragment in each corresponding plurality of nucleic acid methylation fragments in the first training dataset 120-1), and a reconstruction score function 144 that computes a reconstruction score that is determined at least in part by a reconstruction of a corresponding methylation pattern 128 of a respective nucleic acid methylation fragment 124 by a trained autoencoder 132 upon inputting the corresponding methylation pattern and the corresponding nucleic acid sequence 126 of the respective nucleic acid methylation fragment into the trained autoencoder (e.g., for each respective nucleic acid methylation fragment in each corresponding plurality of nucleic acid methylation fragments in the second training dataset 120-2);

instructions, programs, data or information associated with a plurality of features 146 identified using the second training dataset 120-2 and the trained autoencoder 132; and instructions, programs, data or information associated with a supervised model 148 that discriminates between the first cancer state and the second cancer state.

In various implementations, one or more of the above-identified elements are stored in one or more of the previously mentioned memory devices, and correspond to a set of instructions for performing various methods described herein. The above-identified modules, data, or programs (e.g., sets of instructions) may not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above-identified elements are stored in a computer system, other than that of the system 100, that is addressable by the system 100 so that the system 100 may retrieve all or a portion of such data.

Although FIG. 1 depicts a "system 100," the figure is intended more as functional description of the various features which may be present in computer systems than as a structural schematic of the implementations described herein. In practice, and as recognized by those of ordinary skill in the art, items shown separately could be combined and some items can be separate. Moreover, although FIG. 1 depicts certain data and modules in the memory (which can be non-persistent memory 111 or persistent memory 112), it should be appreciated that these data and modules, or portion(s) thereof, may be stored in more than one memory.

While a system in accordance with the present disclosure has been disclosed with reference to FIG. 1, methods in accordance with the present disclosure are now detailed. Any of the methods in accordance with embodiments of the present disclosure can make use of any of the assays, algorithms, or techniques, or combinations thereof, disclosed in U.S. Patent Publication No. US 2018-0237863 A1 entitled "Methods and Systems for Tumor Detection," and/ or International Patent Publication No. WO 2018/081130 entitled "Methods and Systems for Tumor Detection," the content of each of which is hereby incorporated herein by reference in its entirety, in order to determine a cancer condition in a test subject or a likelihood that the subject has the cancer condition.

FIGS. 5A-5E illustrate an example of a method in accordance with some embodiments of the present disclosure. Methods for Identifying Features that Discriminate Between a First and a Second Cancer State Referring to Block 502, one aspect of the present disclosure provides a method of discriminating between a first cancer state (e.g., healthy and/or non-cancer) and a second cancer state (e.g., cancer), where the first cancer state is different than the second cancer state, at a computer system 100 comprising at least one processor 102 and a memory 111/112 storing at least one program for execution by the at least one processor. The at least one program comprises instructions for performing the method.

Referring to Block 504, the method comprises obtaining a first training dataset 120, in electronic form. The first training dataset comprises, for each respective training subject 122 in a first plurality of training subjects, a corresponding methylation pattern 128 and a corresponding nucleic acid sequence 126 of each respective nucleic acid methylation fragment 124 in a corresponding plurality of nucleic acid methylation fragments determined by a methylation sequencing of nucleic acids in a biological sample obtained from the respective training subject 122. The corresponding methylation pattern 128 comprises a methylation state 130 of each respective CpG site (e.g., two or more sites, three or more sites, four or more sites, five or more sites, six or more sites, seven or more sites, eight or more sites, nine or more sites, 10 or more sites, 11 or more sites, 12 or more sites, 13 or more sites, 14 or more sites, or 15 or more sites) in a corresponding plurality of CpG sites in the respective nucleic acid methylation fragment 124, and each training subject 122 in the first plurality of training subjects has the first cancer state.

Training Subjects

In some embodiments, each training subject 122 in the first plurality of training subjects is any of the examples of subjects as defined above (see, Definitions). In some embodiments, each training subject in the first plurality of training subjects is a human. In some embodiments, the first plurality of training subjects is a study group. For example, in some embodiments, the first plurality of subjects is a plurality of participants from a CCGA study (see, e.g., Example 1 below).

Biological Samples

In some embodiments, the biological sample is any of the examples of biological samples as defined above (see, Definitions). In some embodiments, the biological sample is a liquid biological sample or a tissue sample. Referring to Blocks 506-508, in some embodiments, the biological sample is a blood sample (Block 506). In some embodiments, the biological sample comprises blood, whole blood, plasma, serum, urine, cerebrospinal fluid, fecal, saliva, sweat, tears, pleural fluid, pericardial fluid, or peritoneal fluid of the test subject (Block 508). In some embodiments, the biological sample consists of blood, whole blood, plasma, serum, urine, cerebrospinal fluid, fecal, saliva, sweat, tears, pleural fluid, pericardial fluid, or peritoneal fluid of the subject. In some embodiments, the biological sample comprises cell-free DNA (cfDNA). In some embodiments, the biological sample is derived from a cell source. In some embodiments, the biological sample is obtained from a test subject having cancer or from a healthy (e.g., non-cancer) test subject. In some embodiments, the biological sample is obtained from tumor tissue (e.g., cancer) or from healthy tissue (e.g., non-cancer).

Referring to Blocks 510-512, in some embodiments, the respective biological sample is homogenous for the first cancer state (e.g., a tissue sample) (Block 510). In some embodiments, the respective biological sample is a tumor sample that is homogenous for the first cancer state (Block 512). In some embodiments, the respective biological sample is non-homogenous for the first cancer state (e.g., a liquid biological sample that is non-homogenous for the first cancer state).

In some embodiments, the biological sample is obtained from an archived sample (e.g., a frozen, desiccated, or alternatively stored tissue biopsy or blood sample). The time between obtaining a biological sample and performing an assay, such as a sequencing assay, can be optimized to improve the sensitivity and/or specificity of the assay or method. In some embodiments, a biological sample can be obtained immediately before performing an assay. In some embodiments, a biological sample can be obtained, and stored for a period of time (e.g., hours, days or weeks) before performing an assay. In some embodiments, an assay can be performed on a sample within 1 day, 2 days, 3 days, 4 days, 5 days, 6 days, 1 week, 2 weeks, 3 weeks, 4 weeks, 5 weeks, 6 weeks, 7 weeks, 8 weeks, 3 months, 4 months, 5 months, 6 months, 1 year, or more than 1 year after obtaining the sample from the training subject.

Figure 7:
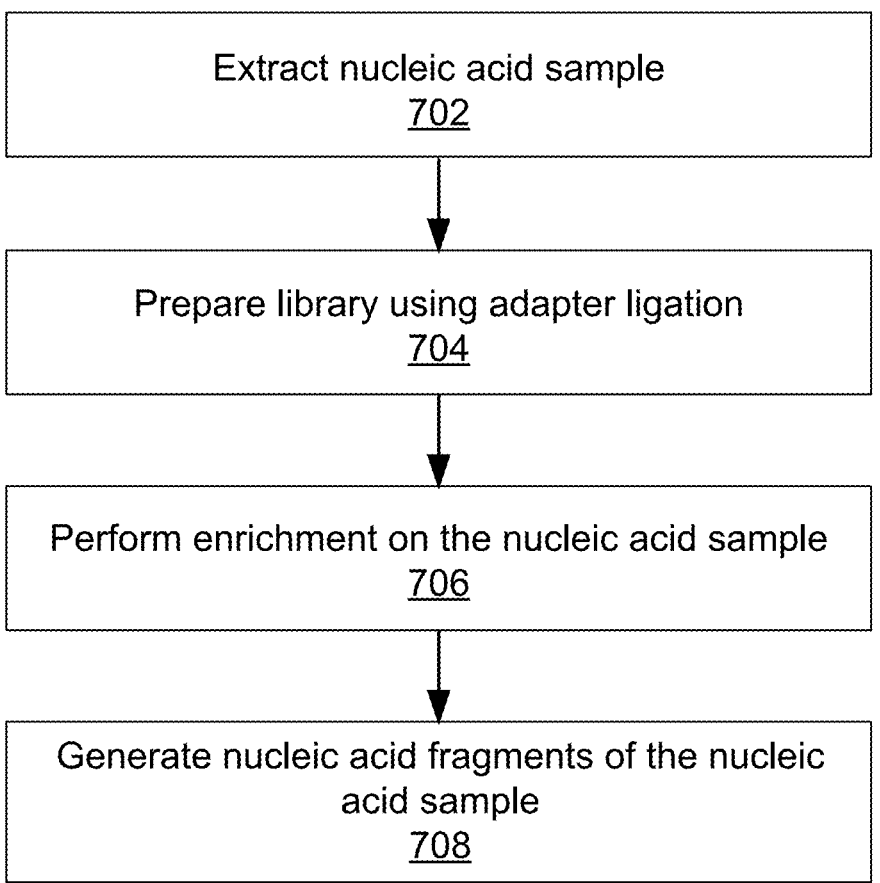
FIG. 7 illustrates a flowchart of a method for preparing a nucleic acid sample for sequencing in accordance with some embodiments of the present disclosure.
Figure 8:
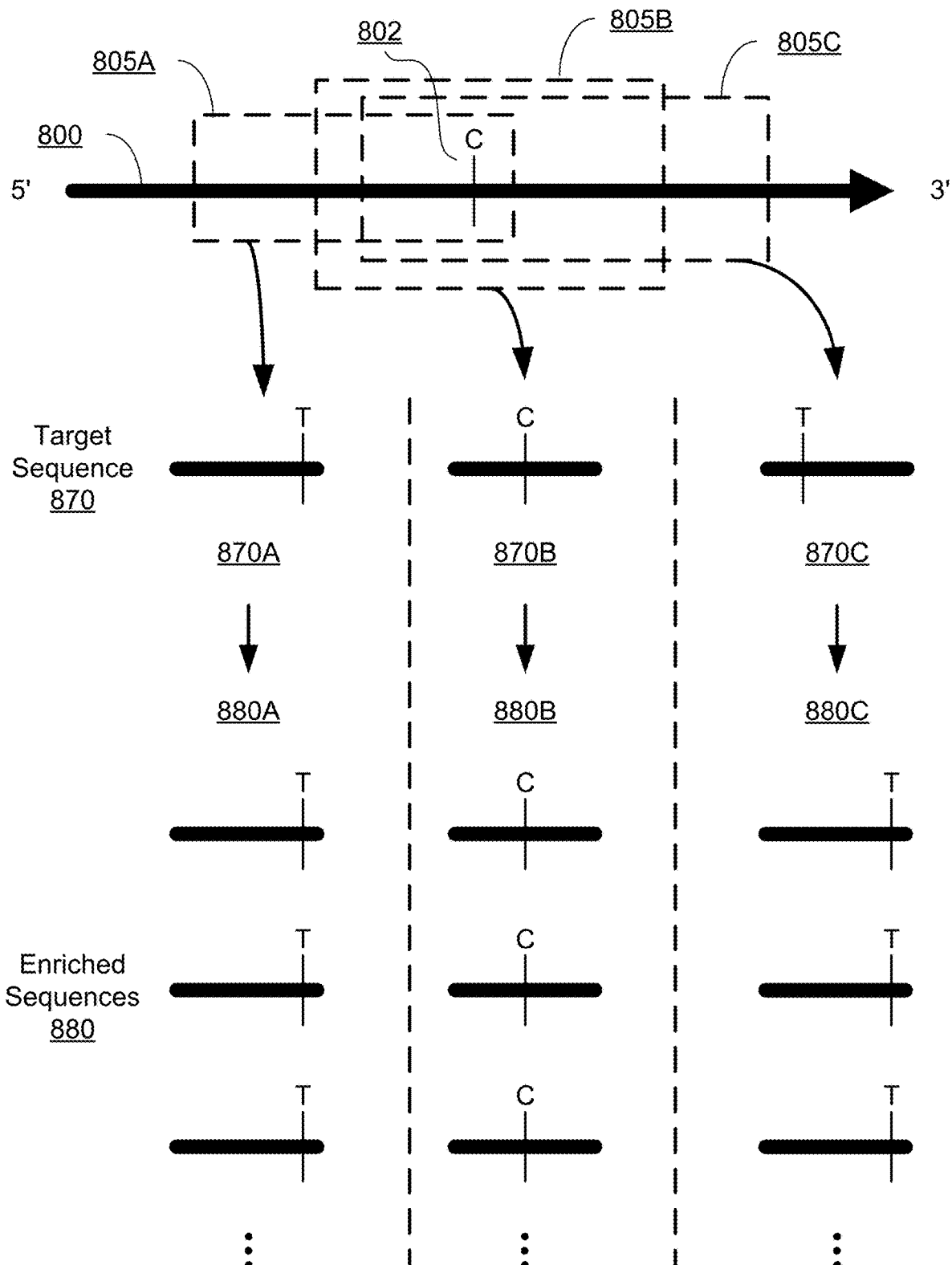
FIG. 8 illustrates a graphical representation of the process for obtaining nucleic acid methylation fragments in accordance with some embodiments of the present disclosure.
Figure 9:
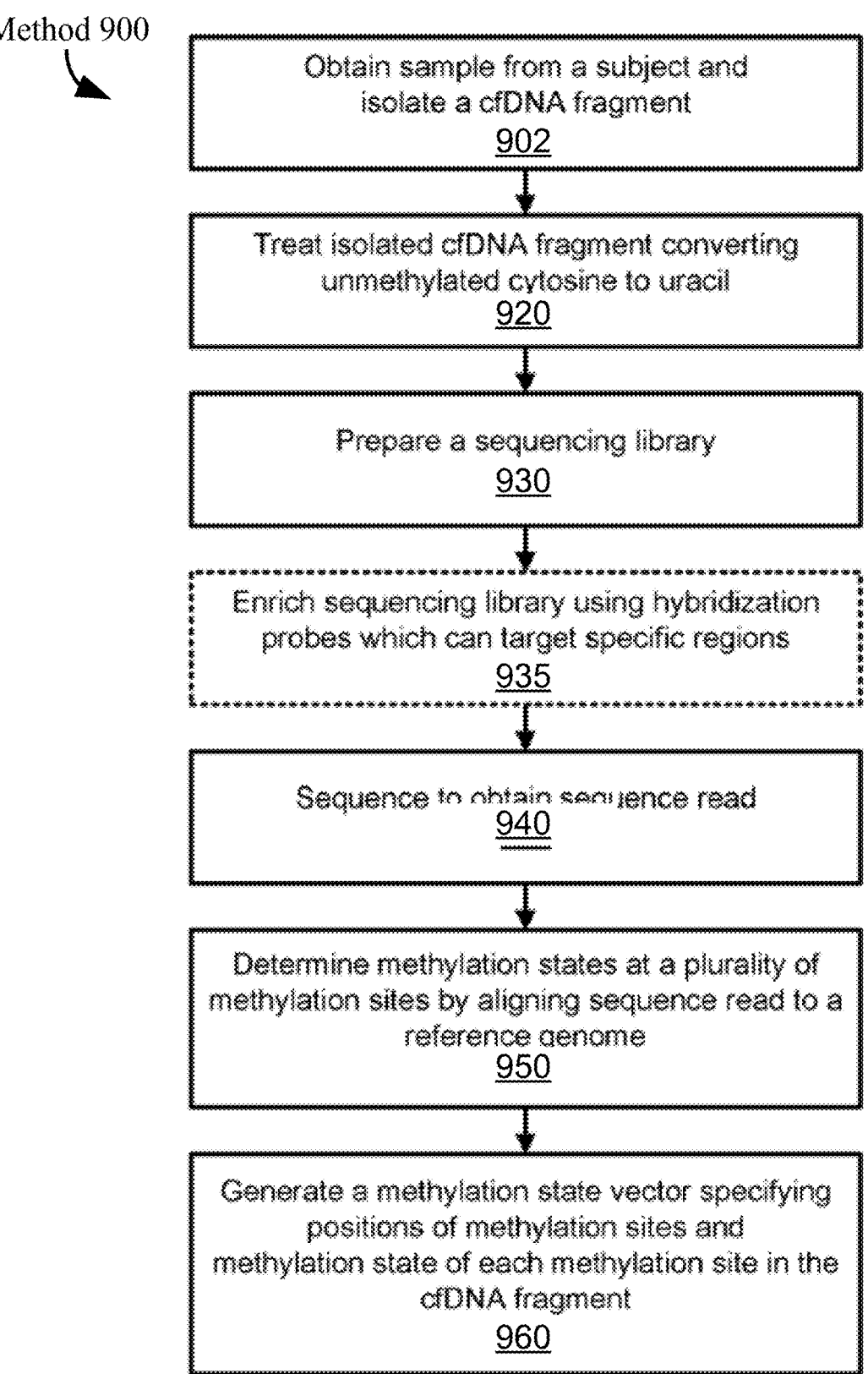
FIG. 9 illustrates an example flowchart of a method for obtaining methylation information for the purposes of screening for a cancer condition in a test subject in accordance with some embodiments of the present disclosure.

In some embodiments, the biological sample is a plurality of biological samples (e.g., a pooled sample comprising a plurality of samples). A plurality of biological samples can be pooled at any point prior to obtaining the first dataset. For example, in some embodiments, pooling the plurality of biological samples occurs prior to nucleic acid extraction (e.g., pooling a plurality of tissue and/or liquid biological samples), after nucleic acid extraction but before methylation sequencing (e.g., pooling a plurality of nucleic acid samples), or after methylation sequencing (e.g., pooling sequencing data from a plurality of sequencing assays). FIGS. 7, 8 and 9 illustrate example flowcharts of methods for preparing nucleic acid samples for sequencing and for obtaining sequencing and methylation sequencing data from biological samples, in accordance with some embodiments of the present disclosure (see, e.g., Examples 2 and 3 below). Obtaining Nucleic Acid Methylation Fragments In some embodiments, the nucleic acids in the respective biological sample obtained from the respective subject is any form of nucleic acid, or a combination thereof. For example, in some embodiments, the nucleic acids in the biological sample is a mixture of RNA and DNA. In some embodiments, the nucleic acids are DNA. In some embodiments, the nucleic acids are cell-free nucleic acids.

As used herein, a nucleic acid methylation fragment refers to a nucleic acid fragment comprising a corresponding methylation pattern (see, Definitions) and a corresponding nucleic acid sequence, where the corresponding methylation pattern and the corresponding nucleic acid sequence is determined by sequencing. In some embodiments, the corresponding methylation pattern and/or the corresponding nucleic acid sequence of each respective nucleic acid methylation fragment is obtained by one or more sequencing methods performed either simultaneously or separately.

The one or more sequencing methods can comprise any form of sequencing that can be used to obtain a number of sequence reads measured from nucleic acids (e.g., cell-free nucleic acids), including, but not limited to, high-throughput sequencing systems such as the Roche 454 platform, the Applied Biosystems SOLID platform, the Helicos True Single Molecule DNA sequencing technology, the sequencing-by-hybridization platform from Affymetrix Inc., the single-molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and Nanopore sequencing can also be used to obtain sequence reads from the nucleic acids (e.g., cell-free nucleic acids) in the biological sample.

For example, in some embodiments, the one or more sequencing methods comprise a whole genome sequencing assay. A whole-genome sequencing assay refers to a physical assay that generates sequence reads for a whole genome or a substantial portion of the whole genome which can be used to determine large variations such as copy number variations or copy number aberrations. Such a physical assay may employ whole genome sequencing techniques or whole-exome sequencing techniques.

In some embodiments, a whole-genome sequencing assay has an average sequencing depth of at least 1×, 2×, 3×, 4×, 5×, 6×, 7×, 8×, 9×, 10×, at least 20×, at least 30×, or at least 40× across the genome of the test subject. In some embodiments, the sequencing depth is about 30,000×.

In some embodiments, the one or more sequencing methods comprise a targeted panel sequencing assay. In some such embodiments, a targeted panel sequencing assay has an average sequencing depth of at least 50,000×, at least 55,000×, at least 60,000×, or at least 70,000× sequencing depth for the targeted panel of genes. In some such embodiments, the targeted panel of genes comprises between 450 and 500 genes. In some embodiments, the targeted panel of genes comprises a range of 500±5 genes, a range of 500±10 genes, or a range of 500±25 genes.

In some embodiments, the one or more sequencing methods comprise a methylation sequencing assay (see, Definitions). In some embodiments, the methylation sequencing assay is a whole genome or a targeted assay. In some such embodiments, the methylation sequencing is performed using tissue (e.g., a tumor biopsy) or a liquid biological sample (e.g., blood, plasma, and/or white blood cells). For example, referring to Block 514, in some embodiments, the methylation sequencing of nucleic acids in a biological sample obtained from the respective subject is methylation sequencing of cell-free nucleic acids in the biological sample. Referring to Block 516, in some embodiments, the methylation sequencing is i) whole-genome methylation sequencing or ii) targeted DNA methylation sequencing using a plurality of nucleic acid probes. In some embodiments, the plurality of nucleic acid probes comprises one hundred or more probes. In some embodiments, the plurality of nucleic acid probes comprises 100 or more, 200 or more, 300 or more, 400 or more, 500 or more, 600 or more, 700 or more, 800 or more, 900 or more, 1000 or more, 2000 or more, 3000 or more, 4000 or more 5000 or more, 6000 or more, 7000 or more, 8000 or more, 9000 or more, 10,000 or more, 25,000 or more, or 50,000 or more probes. In some embodiments, some or all of the probes uniquely map to a genomic region described in International Patent Publication No. WO2020154682A3, entitled "Detecting Cancer, Cancer Tissue or Origin, or Cancer Type," which is hereby incorporated by reference, including the Sequence Listing referenced therein. In some embodiments, some or all of the probes uniquely map to a genomic region described in International Patent Publication No. WO2020/069350A1, entitled "Methylated Markers and Targeted Methylation Probe Panel," which is hereby incorporated by reference, including the Sequence Listing referenced therein. In some embodiments, some or all of the probes uniquely map to a genomic region described in International Patent Publication No. WO2019/195268A2, entitled "Methylated Markers and Targeted Methylation Probe Panels," which is hereby incorporated by reference, including the Sequence Listing referenced therein.

In some embodiments, the one or more sequencing methods comprise whole-genome bisulfite sequencing (e.g., WGBS). In some such embodiments, WGBS identifies one or more methylation state vectors as described, for example, United States Patent Publication No. US 2019-0287652 A1 entitled "Anomalous Fragment Detection and Classification," or in accordance with any of the techniques disclosed in United States Patent Publication No. US 2020-0365229 A1, entitled "Model-Based Featurization and Classification," each of which is hereby incorporated by reference.

In some embodiments, a methylation sequencing assay (e.g., WGBS and/or targeted methylation sequencing) has an average sequencing depth including but not limited to up to about 1,000×, 2,000×, 3,000×, 5,000×, 10,000×, 15,000×, 20,000×, or 30,000×. In some embodiments, the methylation sequencing has a sequencing depth that is greater than 30,000×, e.g., at least 40,000× or 50,000×. See, Ziller et al., 2015, "Coverage recommendations for methylation analysis by whole-genome bisulfite sequencing," Nature Methods. 12(3):230-232, doi:10.1038/nmeth.3152, and Masser et al., 2015, "Targeted DNA Methylation Analysis by Next-generation Sequencing," J. Vis. Exp. (96), e52488, doi:10.3791/52488, which are hereby incorporated herein by reference in their entirety.

Referring to Blocks 518-520, in some embodiments, the methylation sequencing detects one or more 5-methylcytosine (5mC) and/or 5-hydroxymethylcytosine (5hmC) in respective nucleic acid methylation fragments (Block 518). In some embodiments, the methylation sequencing of nucleic acids comprises conversion of one or more unmethylated cytosines or one or more methylated cytosines, in respective nucleic acid methylation fragments, to a corresponding one or more uracils (Block 520). In some such embodiments, the one or more uracils are detected during the methylation sequencing as one or more corresponding thymines. In some such embodiments, the conversion of one or more unmethylated cytosines or one or more methylated cytosines comprises a chemical conversion, an enzymatic conversion, or combinations thereof.

For example, bisulfite conversion involves converting cytosine to uracil while leaving methylated cytosines (e.g., 5-methylcytosine or 5-mC) intact. In some DNA, about 95% of cytosines are not methylated in the DNA, and the resulting DNA fragments will include many uracils which, in the final sequence reads, are represented by thymines. To address this, in some embodiments, enzymatic conversion processes may be used to treat the nucleic acids prior to sequencing, which can be performed in various ways. One example of a bisulfite-free conversion comprises a bisulfite-free and base-resolution sequencing method, TET-assisted pyridine borane sequencing (TAPS), for non-destructive and direct detection of 5-methylcytosine and 5-hydroxymethyl-cytosine without affecting unmodified cytosines. See, Liu et al., "Bisulfite-free direct detection of 5-methylcytosine and 5-hydroxymethylcytosine at base resolution," Nat Biotechnol, doi: 10.1038/s41587-019-0041-2. Regardless of the specific enzymatic conversion approach, only the methylated cytosines are converted.

For further details regarding methylation sequencing (e.g., WGBS and/or targeted methylation sequencing), see, e.g., United States Patent Publication No. US 2019-0287652 A1, entitled "Methylation Fragment Anomaly Detection," and United States Patent Publication No. 2020-0385813 A1, entitled "Systems and Methods for Estimating Cell Source Fractions Using Methylation Information," each of which is hereby incorporated by reference. Other methods for methylation sequencing, including those disclosed herein and/or any modifications, substitutions, or combinations thereof, can be used to obtain fragment methylation patterns.

In some embodiments, the methylation state of a respective CpG site in the corresponding plurality of CpG sites in the respective nucleic acid methylation fragment is methylated when the respective CpG site is determined by the methylation sequencing to be methylated, unmethylated when the respective CpG site is determined by the methylation sequencing to not be methylated, and flagged as "other" when the methylation sequencing is unable to call the methylation state of the respective CpG site as methylation or unmethylated.

In some embodiments, a methylated state is represented as "M", and an unmethylated state is represented as "U". In some embodiments, the methylation state further includes but is not limited to unmethylated, methylated, ambiguous (e.g., meaning the underlying CpG is not covered by any reads in the pair of sequence reads), variant (e.g., meaning that the read is not consistent with a CpG occurring in its expected position based on the reference sequence and can be caused by a real variant at the site or a sequence error), or conflict (e.g., when the two reads both overlap a CpG but are not consistent). See, e.g., U.S. patent application Ser. No. 17/119,606, entitled "Cancer classification using patch convolutional neural networks," filed Dec. 11, 2020, which is hereby incorporated herein by reference in its entirety.

Processing of First Training Dataset

The first training dataset 120 can be of any size and comprise any number of nucleic acid methylation fragments in the corresponding plurality of nucleic acid methylation fragments, depending on the number, type, and coverage of the sequencing methods used, the number of biological samples obtained from a respective subject, and/or the number of training subjects in the first plurality of training subjects. For example, in some embodiments, the corresponding plurality of nucleic acid methylation fragments determined by a methylation sequencing of nucleic acids in a biological sample obtained from a single respective subject in the first training dataset or the second training dataset comprises one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments. In some embodiments, the first plurality of training subjects comprises 10 or more, 20 or more, 30 or more, 50 or more, 100 or more, 1000 or more, 2000 or more, 3000 or more, or 5000 or more training subjects.

In some embodiments, the first training dataset 120 is obtained in an electronic format (e.g., a BAM file and/or a RecordIO PRIO file). In some embodiments, the first training dataset 120 is obtained in a first electronic format (e.g., a BAM file) that is used to generate a second electronic format (e.g., a PRIO file and/or a BED file). In some embodiments, the first training dataset 120 comprises a fragment file comprising the methylation states (e.g., methylation patterns) of each respective nucleic acid methylation fragment in the plurality of nucleic acid methylation fragments.

In some embodiments, the methylation patterns of each respective nucleic acid methylation fragment can be mapped back to a reference genome (see, Definitions). In some preferred embodiments, each respective nucleic acid methylation fragment maps to a single location in the reference genome.

In some embodiments, mapping the methylation patterns of each respective nucleic acid methylation fragments to a reference genome comprises using a CpG index. For example, in some such embodiments, a CpG index comprises a list of each CpG site in the plurality of CpG sites (e.g., CpG 1, CpG 2, CpG 3, etc.) in a reference genome (e.g., a human genome). The CpG index further comprises a corresponding genomic location, in the corresponding reference genome, for each respective CpG site in the CpG index. Each CpG site in each respective nucleic acid methylation fragment is thus indexed to a specific location in the respective reference genome, which can be determined using the CpG index. For instance, in some embodiments the CpG index is obtained from MethHC, MethHC 2.0, MethDB, PubMeth, IMETHYL, experimental findings, and/or publications. See, for example, Huang et al., 2021, "MethHC 2.0: information repository of DNA methylation and gene expression in human cancer," Nucleic Acids Research 49(D1), D1268-D1275; Grunau et al., 2001, "MethDB—a public database for DNA methylation data," Nucleic Acids Research 29(1), 270-274; Ongenaert et al., "PubMeth: a cancer methylation database combining text-mining and expert annotation," Nucleic Acids Research: doi:10.1093/nar/gkm788; and Hachiya et al., 2017, "Genome-wide identification of inter-individually variable DNA methylation sites improves the efficacy of epigenetic association studies," NPJ Genom Med. 2017. 2:11, each of which is hereby incorporated by reference. In some embodiments, the reference genome is obtained in electronic format.

In some embodiments, the corresponding nucleic acid sequence of a respective nucleic acid methylation fragment is obtained by mapping the corresponding methylation pattern of the nucleic acid methylation fragment to a reference genome (e.g., using a CpG index), where the respective nucleic acid methylation fragment maps to a single location in the reference genome.

In some embodiments, the at least one program further comprises instructions for, after the obtaining (e.g. of the first training dataset) and prior to the training (e.g., of the untrained autoencoder), filtering each corresponding plurality of nucleic acid methylation fragments 124 of each training subject 122 by removing, from the corresponding plurality of nucleic acid methylation fragments, each respective nucleic acid methylation fragment that fails to satisfy one or more selection criteria.

In some such embodiments, the respective nucleic acid methylation fragment fails to satisfy a selection criterion in the one or more selection criteria when the methylation pattern of the respective nucleic acid methylation fragment has an output p-value that fails to satisfy a p-value threshold. In some embodiments, the output p-value of the respective nucleic acid methylation fragment is determined, at least in part, based upon a comparison of the methylation pattern of the respective nucleic acid methylation fragment over a plurality of CpG sites of the respective nucleic acid methylation fragment to a corresponding distribution of methylation patterns of those nucleic acid methylation fragments in the first training dataset that have the same corresponding plurality of CpG sites. For instance, consider the case where a respective nucleic acid methylation fragment has a corresponding pattern of MMUMU JMMUM for a particular set of 10 CpG sites. In some embodiments, to calculate the p-value of this fragment, the respective methylation pattern of this particular set of 10 CpG sites for each fragment in the first dataset, regardless of which subject they were measured from, is used to construct a corresponding state vector. The frequency of each respective methylation pattern exhibited by these fragments for the particular set of 10 CpG sites is used to calculate the probability of each such pattern. For instance, the probability of the pattern (state vector) MMMMMMMMMM, the probability for the pattern MUMMMMMMMM, the probability for the pattern MMUMMMMMMM and so forth is computed, for example, as described in United States Patent Publication No. US 2019-0287652 A1, the content of which is incorporated herein by reference. In particular, one embodiment of such computations is described in conjunction with step 420 of FIG. 4 of United States Patent Publication No. US 2019-0287652 A1. Next, the p-value score for the pattern (state vector) M MUM is computed based on the calculated probabilities of all the patterns (state vectors) for the 10 CpG sites observed across the nucleic acid methylation fragments in the first training dataset that have the same corresponding plurality of CpG sites. One embodiment of such computations is described in conjunction with step 430 of FIG. 4 of United States Patent Publication No. US 2019-0287652 A1. In some embodiments, the p-value for the pattern MMU-MUUMMUM is a summation of the calculated probabilities of all observed patterns (state vectors) that are less than or equal to the calculated probability of the pattern MMU-MUUMMUM across all the patterns for the 10 CpG sites observed across the nucleic acid methylation fragments in the first training dataset that have the same corresponding plurality of CpG sites.

In some embodiments, the removing, from the corresponding plurality of nucleic acid methylation fragments, each respective nucleic acid methylation fragment that fails to satisfy a p-value threshold removes more than 5%, more than 10%, more than 20%, more than 30%, more than 40%, more than 50%, more than 60%, more than 70%, more than 80%, more than 90%, more than 95%, more than 98%, or more than 99% of the corresponding plurality of nucleic acid methylation fragments. In some embodiments the p-value is between 0.0005 and 0.01 (e.g., only those fragments having a p-value of 0.0005 or less being retained, only those fragments having a p-value of 0.01 being retained, etc.). In some such embodiments, the p-value is between 0.00001 and 0.20. In some embodiments the p-value is between 0.0010 and 0.00020. In some embodiments the p-value is between 0.0010 and 0.01. In some embodiments the p-value is between 0.01 and 0.05. In some embodiments the p-value is between 0.05 and 0.2.

In some embodiments, the removing, from the corresponding plurality of nucleic acid methylation fragments, each respective nucleic acid methylation fragment that fails to satisfy a p-value threshold removes nucleic acid methylation fragments that are common (e.g., that have a high probability of observation) in the first training dataset, thereby retaining nucleic acid methylation fragments that are rare (e.g., that have a low probability of observation) in the first training dataset.

For example, without being bound to any particular theory of operation, in some embodiments, rare nucleic acid methylation fragments (e.g., that satisfy a p-value threshold) can provide greater discriminative power for the respective condition of interest of the respective training dataset. In particular, in some such embodiments, rare nucleic acid methylation fragments provide characteristic features and thus are more representative of the condition of interest. Additionally, in some embodiments, the removal of common nucleic acid methylation fragments (e.g., that fail to satisfy a p-value threshold) from a first training dataset removes nucleic acid methylation fragments with a high probability of observation in, for example, a second training dataset (e.g., of an unknown or test sample). In some such embodiments, common nucleic acid methylation fragments are likely to be uninformative with respect to discrimination between conditions of interest (e.g., between cancer and non-cancer).

The removal of nucleic acid methylation fragments that fail to satisfy a p-value threshold (e.g., fail to have a p-value that is less than the p-value threshold) from the plurality of nucleic acid methylation fragments therefore provides advantages over conventional methods by increasing the discriminative power of the remaining nucleic acid methylation fragments and thereby improving the performance of the unsupervised model (e.g., the autoencoder) as well as the downstream supervised model (e.g., the classifier). Furthermore, in some embodiments, the removal of such uninformative nucleic acid methylation fragments (e.g., more than 5%, more than 10%, more than 20%, more than 30%, more than 40%, more than 50%, more than 60%, more than 70%, more than 80%, more than 90%, more than 95%, more than 98%, or more than 99%) from the corresponding plurality of nucleic acid methylation fragments reduces the computational power required to train the autoencoder while retaining the efficacy of training.

In some embodiments, the respective nucleic acid methylation fragment from the first training dataset fails to satisfy a selection criterion in the one or more selection criteria when an output p-value provided by a trained Markov model, responsive to input of the methylation pattern of the respective nucleic acid methylation fragment, fails the selection criterion, and the trained Markov model is trained, at least in part, based upon evaluation of a methylation state of each CpG site in a plurality of CpG sites of the respective nucleic acid methylation fragment across those nucleic acid methylation fragments in the first training dataset that have the corresponding plurality of CpG sites.

For example, in some embodiments, a Markov model (e.g., a Hidden Markov Model or HMM) is used to determine the probability that a sequence of methylation states (comprising, e.g., "M" or "U") will be observed for a nucleic acid methylation fragment in a plurality of nucleic acid methylation fragments, given a set of probabilities that determine, for each state in the sequence, the likelihood of observing the next state in the sequence.

In some embodiments, the set of probabilities are obtained by training the HMI. Such training involves computing statistical parameters (e.g., the probability that a first state will transition to a second state (the transition probability) and/or the probability that a given methylation state will be observed for a respective CpG site (the emission probability)), given an initial training dataset of observed methylation state sequences (e.g., methylation patterns). In some embodiments, HMIs are trained using supervised training (e.g., using samples where the underlying sequence as well as the observed states are known). In some alternative embodiments, HMIs are trained using unsupervised training (e.g., Viterbi learning, maximum likelihood estimation, expectation-maximization training, and/or Baum-Welch training). For example, an expectation-maximization algorithm such as the Baum-Welch algorithm estimates the transition and emission probabilities from observed sample sequences and generates a parameterized probabilistic model that best explains the observed sequences. Such algorithms iterate the computation of a likelihood function until the expected number of correctly predicted states is maximized. See, e.g., Yoon, 2009, "Hidden Markov Models and their Applications in Biological Sequence Analysis," Curr. Genomics. September; 10(6): 402-415, doi: 10.2174/138920209789177575.

For example, FIG. 4 illustrates a method 214 of filtering a plurality of nucleic acid methylation fragments by removing each respective nucleic acid methylation fragment that fails to satisfy a p-value threshold, in accordance with some embodiments of the present disclosure. The filter is applied to the methylation pattern of each respective nucleic acid methylation fragment in the first plurality of nucleic acid methylation fragments in the respective first training dataset, using the methylation patterns observed across the first plurality of nucleic acid methylation fragments. Each respective methylation pattern of each respective nucleic acid methylation fragment (e.g., Fragment One, . . . , Fragment N) comprises a corresponding one or more methylation sites (e.g., CpG sites) identified with a methylation site identifier and a corresponding methylation pattern, represented as a sequence of 1's and 0's, where each "1" represents a methylated CpG site in the one or more CpG sites and each "0" represents an unmethylated CpG site in the one or more CpG sites. The methylation patterns observed across the first plurality of nucleic acid methylation fragments are used to build a methylation state distribution for the CpG site states collectively represented by the first plurality of nucleic acid methylation fragments (e.g., CpG site A, CpG site B, CpG site ZZZ).

As described in FIG. 4, transition probabilities between states for a Hidden Markov Model (HMM) are represented by the arrows in the illustration, and can be determined using the methylation state distribution for the CpG site states (e.g., using an expectation-maximization algorithm such as the Baum-Welch algorithm), thereby training the HMM. Hidden Markov model are described, for example, in Schliep et al., 2003, Bioinformatics 19(1):i255-i263. For each respective nucleic acid methylation fragment in the first plurality of nucleic acid methylation fragments, the trained HMM is used to determine the likelihood of occurrence of the methylation pattern of the respective fragment (e.g., using a forward algorithm). Nucleic acid methylation fragments whose likelihoods of occurrence fail to satisfy a first threshold value of the first threshold filter (e.g., their methylation patterns are too common in the first plurality of nucleic acid methylation fragments) are discarded.

In some embodiments, the respective nucleic acid methylation fragment fails to satisfy a selection criterion in the one or more selection criteria when the methylation pattern of the respective nucleic acid methylation fragment has an output p-value that fails to satisfy (e.g., is greater than) a p-value threshold, and the output p-value of the respective nucleic acid methylation fragment is determined by a method other than a Hidden Markov Model. In some embodiments, the output p-value of the respective nucleic acid methylation fragment is determined using a mixture model (such as see, for example, McLachlan et al., Bioinformatics 18(3):413-422, 2002). In some embodiments, the output p-value of the respective nucleic acid methylation fragment is determined using a learned representation.

In some embodiments, the output p-value is between 0.00001 and 0.20. In some embodiments, the output p-value is 0.05 (e.g., where the likelihood of observing the methylation pattern of the respective nucleic acid methylation pattern in the plurality of nucleic acid methylation patterns in the first training dataset is less than 5%). In some embodiments, the output p-value is determined empirically (e.g., as a hyperparameter) based at least in part on one or more requirements for precision (e.g., increased rarity) and/or sensitivity (e.g., greater numbers of training samples).

In some embodiments, a p-value threshold filter is not applied to the corresponding plurality of nucleic acid methylation fragments.

In some embodiments, the respective nucleic acid methylation fragment fails to satisfy a selection criterion in the one or more selection criteria when the respective nucleic acid methylation fragment has less than a threshold sequencing depth. That is, for a given training subject, the respective nucleic acid methylation fragment has less than a threshold sequencing depth in the sequencing done for the given training subject. In some such embodiments, the threshold sequencing depth is 5×, 6×, 7×, 8×, 9×, 10×, 15×, 20×, 25×, or 30×, or greater particularly when the sequencing is whole genome sequencing. In some such embodiments, the threshold sequencing depth is 50×, 100×, 200×, 400×, 800×, 1000×, 2000×, 5000×, 10000×, or 25000×, particularly when the sequencing is targeted sequencing.

In some embodiments, the respective nucleic acid methylation fragment fails to satisfy a selection criterion in the one or more selection criteria when the respective nucleic acid methylation fragment has less than a threshold number of CpG sites. In some embodiments, the threshold number of CpG sites is 4, 5, 6, 7, 8, 9, 10, 11, 12, 13, 14, or 15. In some embodiments, the threshold number of CpG sites is determined (e.g., as a hyperparameter) based at least in part on a requirement that each possible methylation pattern of each respective nucleic acid methylation fragment has a threshold likelihood of occurrence (e.g., a likelihood of ⅛ for a sequence of 3 CpG sites, a likelihood of 1/32 for a sequence of 5 CpG sites, etc.).

In some embodiments, the respective nucleic acid methylation fragment fails to satisfy a selection criterion in the one or more selection criteria when the respective nucleic acid methylation fragment has less than a threshold number of residues. For example, in some embodiments, each respective nucleic acid methylation fragment has a length in residues (e.g., base pairs and/or k-mers) that is independent of the number of CpG sites in the respective nucleic acid methylation fragment. Thus, in some embodiments, a selection criterion applies a minimum length requirement to the plurality of nucleic acid methylation fragments prior to anomaly detection. In some embodiments, the threshold number of residues is 32 or 64. In some embodiments, the threshold number of residues is a fixed value between 20 and 90. In some embodiments, the threshold number of residues is greater than 90, greater than 100, greater than 150, or greater than 200.

In some embodiments, the threshold number of residues is determined (e.g., as a hyperparameter) based at least in part on a requirement that the nucleic acid sequence of each respective nucleic acid methylation fragment maps to less than a threshold number of locations in a reference genome. In some preferred embodiments, the threshold number of residues is determined based on a requirement that the nucleic acid sequence of each respective nucleic acid methylation fragment maps to a single location in a reference genome.

In some embodiments, the filtering removes a nucleic acid methylation fragment in the plurality of nucleic acid methylation fragments that has the same corresponding methylation pattern and the same corresponding nucleic acid sequence as another nucleic acid methylation fragment in the plurality of nucleic acid methylation fragments (e.g., exact duplicates are discarded). However, in some experiments a count of duplicated fragments is kept and used to compute a weighting for each fragment that is subsequently used in the loss function used to evaluate the autoencoder.

In some embodiments, the filtering retains a nucleic acid methylation fragment in the plurality of nucleic acid methylation fragments that has the same corresponding methylation pattern and a different corresponding nucleic acid sequence as another nucleic acid methylation fragment in the plurality of nucleic acid methylation fragments.

In some embodiments, the filtering retains a nucleic acid methylation fragment in the plurality of nucleic acid methylation fragments that has a different corresponding methylation pattern but the same corresponding nucleic acid sequence as another nucleic acid methylation fragment in the plurality of nucleic acid methylation fragments.

The removal of exact duplicates provides advantages over conventional methods by collapsing datasets such that each unique nucleic acid methylation fragment (e.g., having at least a unique methylation pattern and/or a unique nucleic acid sequence) is represented in the processed training dataset only once, thereby reducing the computational burden and improving efficiency. The removal of exact duplicates further does not obstruct the detection of anomalous fragments (e.g., in the second training dataset compared to the first training dataset), which in some embodiments is independent of copy number or variant frequencies.

In some embodiments, additional selection criteria can be applied to the plurality of nucleic acid methylation fragments, including but not limited to association with or inclusion of transcription factor encoding, transcription factor datasets, biological and functional pathways of interest, annotations of interest, known cancer markers, and/or any combinations or modifications thereof.

In some embodiments, the filtering removes nucleic fragments that map onto a blacklist of known noisy genomic positions. In some embodiments the blacklist is all or a portion of the ENCODE blacklist. See Ameniya et al. 2019, "The ENCODE Blacklist: Identification of Problematic Regions of the Genome," Scientific Reports 9, article number 9354.

In some embodiments, each respective nucleic acid methylation fragment that is greater than a predetermined length (e.g., in CpG site dimensions and/or in residue dimensions) is truncated by removing a portion of the nucleic acid methylation fragment such that the resulting sequence segment (e.g., as used herein, "sequence segment" refers to a truncated nucleic acid methylation fragment) has the predetermined length (e.g., in CpG site dimensions and/or in residue dimensions).

In some embodiments, the predetermined length is 100 base pairs or more, 128 base pairs or more, 200 base pairs or more, 256 base pairs or more, or 400 base pairs or more.

In some embodiments, each respective nucleic acid methylation fragment that is greater than a predetermined length (e.g., in CpG site dimensions and/or in residue dimensions) is truncated by windowing across the respective nucleic acid methylation fragment with a predetermined stride, thereby breaking the respective nucleic acid methylation fragment into two or more sequence segments, where the window size is equal to or less than the predetermined length, such that the two or more sequence segments each have the predetermined length, each have at least the threshold number of CpG sites, and collectively replace the respective nucleic acid methylation fragment in the corresponding plurality of nucleic acid methylation fragments as input.

In some embodiments, the length of the stride is the same as the window size. In some embodiments, the length of the stride is different from the window size. In some such embodiments, the length of the stride is less than the window size. In some such embodiments, the two or more sequence segments overlap in sequence. In some embodiments, the two or more sequence segments comprise 2, 3, 4, 5, 6, 7, 8, 9, 10, 11, 12, 13, 14, 15, 16, 17, 18, 19, 20, or more than 20 sequence segments.

In some embodiments, one or more sequence segments in the two or more sequence segments fail to satisfy a selection criterion in the one or more selection criteria when the respective one or more sequence segments has less than a threshold number of residues and/or less than a threshold number of CpG sites. In some such embodiments, the one or more sequence segments that fail to satisfy a selection criterion are discarded.

In some embodiments, each respective nucleic acid methylation fragment that is less than a predetermined length (e.g., in CpG site dimensions and/or in residue dimensions) is padded to be the predetermined length prior to training the autoencoder. In some such embodiments, the padding comprises adding one or more dummy residues and/or one or more dummy methylation sites to the respective nucleic acid methylation fragment. In some embodiments, the padding comprises using the nucleic acid methylation fragment mapped to a reference genome to extend the nucleic acid methylation fragment to the predetermined length, based on the corresponding sequence in the reference genome.

In some embodiments, one or more sequence segments, obtained by windowing and striding, that fail to satisfy a selection criterion in the one or more selection criteria when the respective one or more sequence segments has less than a threshold number of residues and/or less than a threshold number of CpG sites, are padded to be the predetermined length.

In some embodiments, the nucleic acid methylation fragment fails to satisfy a selection criterion in the one or more selection criteria when the respective nucleic acid methylation fragment has less than a threshold number of CpG sites (e.g., less than 4, 5, 6, 7, 8, 9, 10, 11, 12, 13, 14, or 15 CpG sites), the obtaining the first training dataset pads each nucleic acid methylation fragment in the corresponding plurality of nucleic acid methylation fragments that is less than a predetermined length to be the predetermined length prior to training the untrained autoencoder, and the obtaining the first training dataset truncates each respective nucleic acid methylation fragment in the corresponding plurality of nucleic acid methylation fragment that is greater than the predetermined length by windowing across the respective nucleic acid methylation fragment with a predetermined stride, thereby breaking the respective nucleic acid methylation fragment into two or more sequence segments. In some such embodiments, the two or more sequence segments each have the predetermined length, each have at least the threshold number of CpG sites (e.g., at least 3, 4, 5, 6, 7, 8, 9, 10, 11, 12, 13, 14, or 15 CpG sites), and collectively replace the respective nucleic acid methylation fragment in the corresponding plurality of nucleic acid methylation fragments as input to the training of the untrained autoencoder.

In some embodiments, the stride is between 90 and 300 nucleotides. In some embodiments, the stride is 100, 128, or 256 nucleotides.

In some embodiments, the obtaining the first training dataset truncates a first nucleic acid methylation fragment in the corresponding plurality of nucleic acid methylation fragments, which is longer than a predetermined length, at a site of variance, conflicting methylation call, or ambiguous call within the first nucleic acid methylation fragment, thereby shortening the first nucleic acid methylation fragment to terminate at the site. For example, in an embodiment, a nucleic acid methylation fragment having a nucleic acid sequence of "TACTGGCGA . . . CGGCCTCG . . . TTTCAAC" and a methylation pattern of "111000X0010" would be split at the "X" (e.g., conflicted) position and the "X" CpG site would be removed from the resulting sequence segments. Using a minimum threshold number of 5 CpG sites, the first sequence segment obtained from the splitting "111000" would be retained, and the second sequence segment "0010" would be discarded.

In some embodiments, CpG sites comprising variant, conflicted, or ambiguous methylation states are not terminated or removed from the nucleic acid methylation fragments.

In some embodiments, one or more sequence segments have different lengths (e.g., in CpG site dimensions and/or residue dimensions). In some alternative embodiments, each respective sequence segment in the plurality of sequence segments, that serve as input for the training the untrained autoencoder, are the same length (e.g., in CpG site dimensions and/or in residue dimensions).

In some embodiments, p-value filtering is performed after the initial preprocessing of nucleic acid methylation fragments (e.g., filtering by size, splitting, truncating, and/or padding). For example, in some embodiments, the p-value determination is dependent on the parameters of the resulting sequence segments (e.g., the length of the sequence segments and/or nucleic acid methylation fragments, where longer nucleic acid methylation fragments comprise lower p-values than shorter fragments). In some such embodiments, each nucleic acid methylation fragment in the plurality of nucleic acid methylation fragments is processed to be a predetermined length prior to the p-value filtering.

In some embodiments, p-value filtering is performed prior to the preprocessing of the nucleic acid methylation fragments. In some embodiments, p-value filtering is performed prior to the removal of duplicates. In some embodiments, the filtering and/or preprocessing of the first training dataset is performed in any order, combinations, and/or with any modifications as will be apparent to one skilled in the art.

Figure 2:
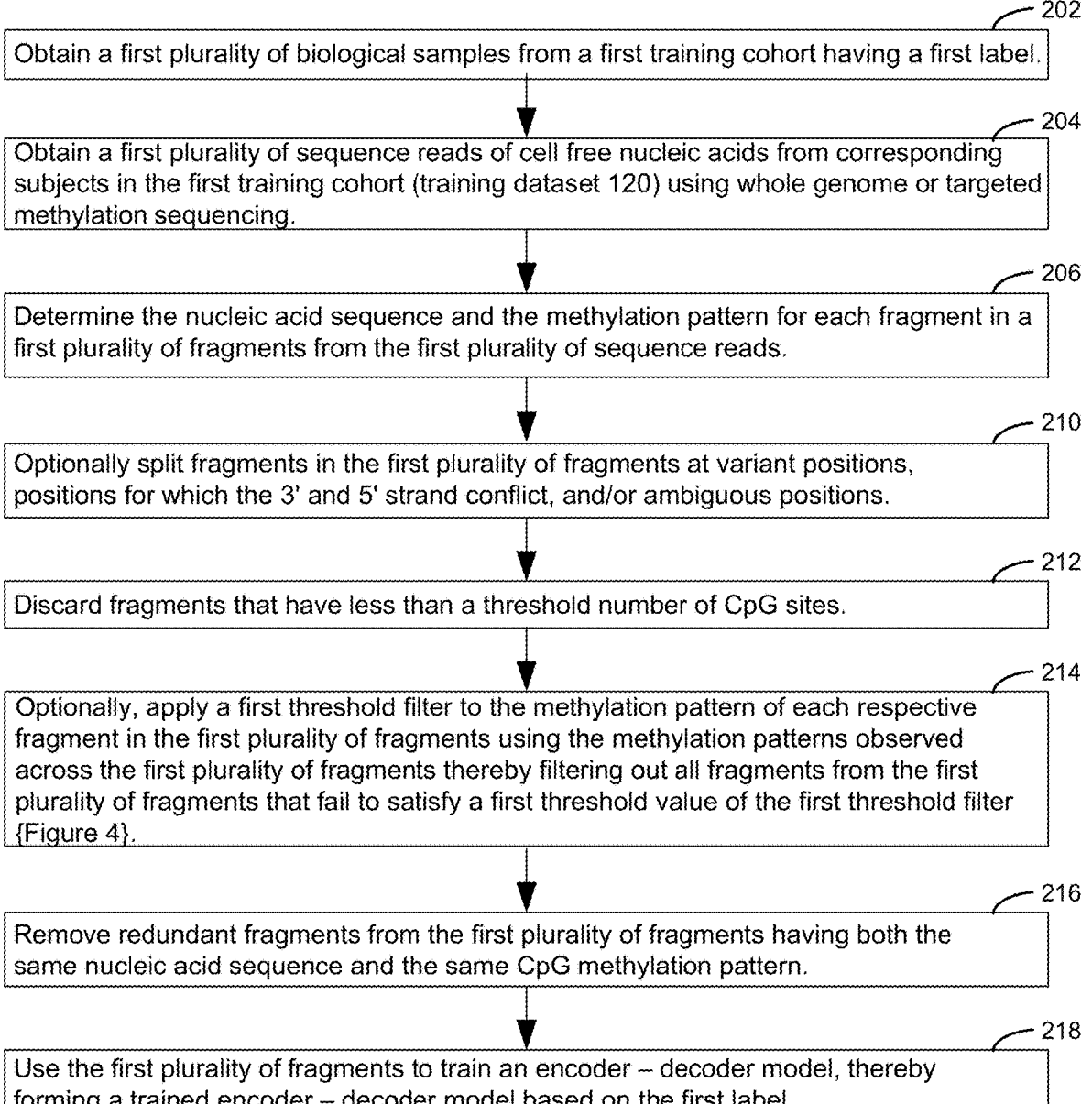
FIG. 2 is a block diagram illustrating an example of a method for obtaining and preprocessing a dataset in accordance with some embodiments of the present disclosure.

For example, FIG. 2 illustrates a flowchart of an example method for obtaining and processing a first training dataset, in accordance with some preferred embodiments. Referring to Block 202, the method comprises obtaining a first plurality of biological samples from a first training cohort having a first label. Referring to Block 204, the first plurality of sequence reads of cell-free nucleic acids from corresponding subjects in the first training cohort are obtained using whole-genome or targeted methylation sequencing. Referring to Block 206, the nucleic acid sequence and the methylation pattern for each fragment in a first plurality of fragments are determined from the first plurality of sequence reads. Referring to Block 210, fragments in the first plurality of fragments are optionally split at known variant positions, positions for which paired-end reads conflict, and/or ambiguous positions. For example, only a portion of the fragment can be used or multiple portions of the fragment can be treated as separate fragments. Referring to Block 212, fragments that have less than a threshold number of CpG sites are discarded. Referring to Block 214, a first threshold filter is optionally applied to the methylation pattern of each respective fragment in the first plurality of fragments using the methylation patterns observed across the first plurality of fragments thereby filtering out all fragments from the first plurality of fragments that fail to satisfy a first threshold value of the first threshold filter. See, for example, FIG. 4. Referring to Block 216, redundant fragments having both the same nucleic acid sequence and the same CpG methylation pattern are removed from the first plurality of fragments. Referring to Block 218, the first plurality of fragments are used to train an encoder-decoder model, thereby forming a trained encoder-decoder model based on the first label.

In a specific embodiment, the method illustrated in FIG. 2 can be performed using processing steps to remove ambiguous/variant/conflicted CpG sites, a minimum length requirement (e.g., variable length, minimum 32 residues, minimum 5 CpG sites), and p-value filtering.

In some embodiments, the training of the untrained autoencoder uses as input a dataset (e.g., training dataset 120-1) comprising a plurality of nucleic acid methylation fragments 124 and/or sequence segments, after any desired preprocessing and/or filtering of the first training dataset as described in the present disclosure. In some embodiments, the input dataset used for training the untrained autoencoder is different from the first training dataset initially obtained, as determined by a methylation sequencing of nucleic acids in a biological sample from a respective subject.

Autoencoder Architecture

Referring to Block 522 of FIG. 5B, the systems and methods of the present enclosure include training an untrained autoencoder, where the untrained autoencoder includes an encoder 134 and a decoder 136, using the corresponding methylation pattern and the corresponding nucleic acid sequence of each respective nucleic acid methylation fragment 124 in each corresponding plurality of nucleic acid methylation fragments in the first training dataset 120-1 as input, by, for each corresponding nucleic acid sequence of each respective nucleic acid methylation fragment in each corresponding plurality of nucleic acid methylation fragments in the first training dataset, evaluating a first error function for an error in the reconstruction by the autoencoder 132 of the corresponding methylation pattern and the corresponding nucleic acid sequence of the corresponding nucleic acid methylation fragment 124, thereby forming a trained autoencoder 132.

In some embodiments, and as used interchangeably herein, the corresponding plurality of nucleic acid methylation fragments in the first training dataset used as input for training the untrained autoencoder comprises one or more sequence segments (e.g., nucleic acid methylation fragments preprocessed and/or filtered as described in the present disclosure).

Referring to Block 524, in some embodiments, the encoder 134 encodes the corresponding methylation pattern and the corresponding nucleic acid sequence of the corresponding nucleic acid methylation fragment in each corresponding plurality of nucleic acid methylation fragments in the first training dataset thereby forming a plurality of latent features, and the decoder 136 decodes the plurality of latent features into a reconstruction of the corresponding methylation pattern and the corresponding nucleic acid sequence of the corresponding nucleic acid methylation fragment.

Figure 10:
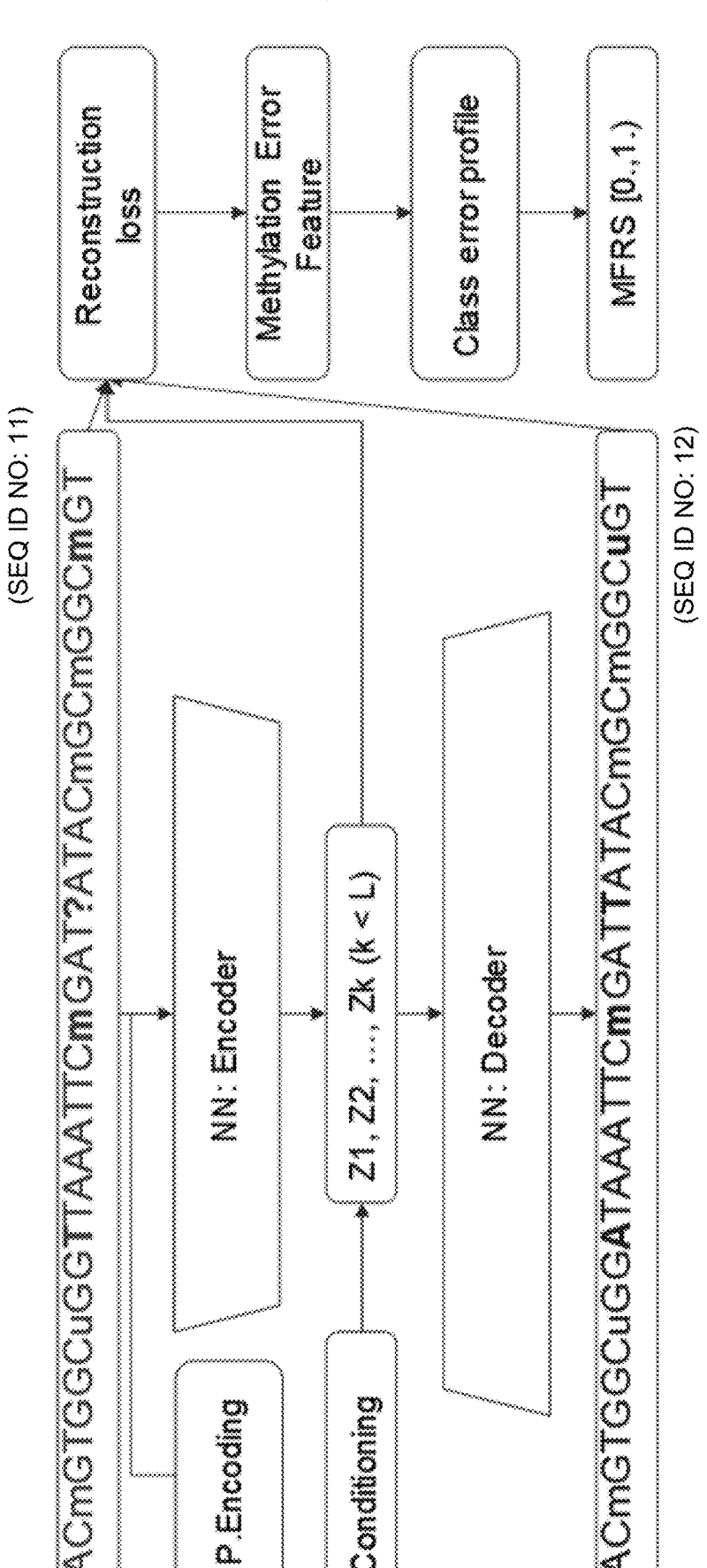
FIG. 10 illustrates an example flowchart of a method of calculating methylation fragment reconstruction scores using an autoencoder, in accordance with some embodiments of the present disclosure.

FIG. 10 illustrates a method for using an autoencoder to encode a nucleic acid methylation fragment. Generally, in some such embodiments, the autoencoder 132 learns to encode, for each respective training input (e.g., a nucleic acid methylation fragment), a latent representation of the respective input (specifically, for example, the corresponding methylation pattern and/or the nucleic acid sequence of the respective nucleic acid methylation fragment). The autoencoder 132 then attempts to reconstruct the input using the learned latent representation of the input. Training an autoencoder on one or more training inputs, in some embodiments, results in a trained autoencoder that produces more accurate reconstructions of test inputs that are similar to the training inputs, but produces less accurate reconstructions of test inputs that are dissimilar to the training inputs, based on the learned latent representations of the one or more training inputs, where the similarity or dissimilarity of the reconstruction to the original input is determined using a reconstruction loss function such as an error function.

In some embodiments, the latent representation is generated as a set (e.g., a vector and/or an N-dimensional tensor) of encodings (e.g., embeddings). In some embodiments, the set of encodings comprises 10 or weights, 1000 or more weights, 10,000 or more weights, or 100,000 or more weights, where the value of each weight is refined and adjusted during the training of the autoencoder 132 with the training dataset 120. In some embodiments, the autoencoder 132 comprises 10 or weights, 1000 or more weights, 10,000 or more weights, or 100,000 or more weights.

In some embodiments, the autoencoder 132 is trained on the sequence and methylation pattern of 100 or more nucleic acid methylation fragments, 200 or more nucleic acid methylation fragments, 300 or more nucleic acid methylation fragments, 500 or more nucleic acid methylation fragments, 1000 or more nucleic acid methylation fragments, 5000 or more nucleic acid methylation fragments, 10,000 or more nucleic acid methylation fragments, 50,000 or more nucleic acid methylation fragments, 100,000 or more nucleic acid methylation fragments, 500,000 or more nucleic acid methylation fragments, or $1 \times 10^6$ or more nucleic acid methylation fragments.

In some embodiments, the autoencoder is constrained to encode a compressed latent representation of the training and/or the test input. In some such embodiments, such compression prevents overfitting by facilitating the construction of latent representations that capture complex patterns and structural relationships (e.g., patterns of k-mers and corresponding methylation states), rather than the reproduction of exact features observed in the training inputs. The compressed latent representations can thus be used for reconstructing both known training inputs and unknown test inputs.

In some embodiments, the compressed representation is generated using a parameter that limits the size of the embeddings layer (e.g., a hidden layer comprising the values of the latent representation), thus limiting the memory capacity of the autoencoder. For example, in some embodiments, the size of the embeddings layer is constrained to be ½ the size of the input. In some embodiments, the size of the embeddings layer is constrained to be less than ¼, less than ½, or less than ¾ the size of the input. In some embodiments, the size of the embeddings layer is determined at least partly by evaluating a first error function for an error in the reconstruction of the autoencoder of the corresponding methylation pattern and the corresponding nucleic acid sequence of the corresponding nucleic acid methylation fragment. In some embodiments, the embedding layer is conditioned on one or more observed variables, such as fragment genomic position.

In some embodiments, the values in the embeddings layer are constrained to be between a first number and a second number. In some such embodiments, the first number is zero and the second number is one. In some embodiments, the encoding is one-hot encoding. In some such embodiments, the values in the embeddings layer are constrained to be either a zero or a one.

In some embodiments, the autoencoder comprises one hidden layer. In some embodiments, the autoencoder comprises 1 or more, 2 or more, 3 or more, 4 or more, 5 or more, 6 or more, 7 or more, 8 or more, 9 or more, or 10 or more hidden layers.

In some embodiments, the autoencoder is a feed-forward artificial neural network.

Referring to Block 526, in some embodiments, the autoencoder is a variational autoencoder (see, for example, Kingma and Max, 2019, *Foundations and Trends in Machine Learning*, 12(4), ISSN 1935-8237), a conditional variational autoencoder (CVAE), a stacked denoising deep autoencoder (see, for example, Zheng, 2019, *Stacked Denoising Auto-Encoder for Short-Term Load Forecasting: Deep Learning with Stacked Denoising Auto-Encoder Algorithm*, Lambert Academic Publishing), a deep recurrent autoencoder, a convolutional autoencoder, or a transformer network. In some embodiments, the autoencoder includes a generative adversarial network (GAN), for example a variational autoencoder generative adversarial network (VAE-GAN) architecture. In some embodiments, the autoencoder is a contractive autoencoder. In some embodiments, the autoencoder is a long short-term memory (LSTM) recurrent neural network. In some embodiments, the LSTM recurrent neural network comprises a stacked bidirectional encoder and a stacked decoder.

In some preferred embodiments, the autoencoder is a variational autoencoder, and the latent representation is constrained to be a predefined distribution, such that each value in the embeddings layer is drawn from the predefined distribution. In some such embodiments, the predefined distribution is a Gaussian distribution. In some embodiments, the predefined distribution is a mixture of Gaussian distributions. Thus, for example, referring to FIG. 10, the tensors $Z_1$, $Z_2$, . . . , $Z_k$ of the embeddings layer of a variational autoencoder are assigned such that plotting the values of each tensor generates a Gaussian distribution.

In some embodiments, the predefined distribution further comprises parameters for one or more measures of central tendency (e.g., mean) and/or measures of error (e.g., standard deviation). In some such embodiments, the raw parameters for such measures are predicted by the autoencoder based on one or more training inputs (e.g., from a first training dataset 120). For example, for a nucleic acid sequence in a respective nucleic acid methylation fragment 124 in the first training dataset, in some implementations, the autoencoder generates a plurality of embeddings representing the mean and standard deviation of each nucleotide base in the sequence. Reconstruction of the respective nucleic acid methylation fragment by the decoder is performed by sampling from the plurality of embeddings and passing these values to the decoder.

Variational autoencoders can provide advantages for purposes of anomaly detection by assigning greater weight to highly discriminative features (e.g., patterns) identified by the autoencoder, while assigning lesser weight to poorly discriminative features. See, for example, Kristiadi, 2016, "Variational Autoencoder: Intuition and Implementation," and Doersch, 2016, "Tutorial on variational autoencoders." arXiv preprint arXiv:1606.05908.

In some embodiments, the training the autoencoder 132, for a respective nucleic acid methylation fragment 124 in a corresponding plurality of nucleic acid methylation fragments in the first training dataset 120, feeds the autoencoder 132 the corresponding methylation pattern 128 of the respective nucleic acid methylation fragment 124.

In some embodiments, the training the autoencoder 132, for a respective nucleic acid methylation fragment 124 in a corresponding plurality of nucleic acid methylation fragments in the first training dataset 120, feeds the autoencoder 132 the corresponding nucleic acid sequence 126 of the respective nucleic acid methylation fragment 124. In some such embodiments, the corresponding nucleic acid sequence is broken into a plurality of overlapping k-mers. As used herein, the term k-mer refers to all of a sequence's subsequences of length k, such that the sequence AGAT would have four monomers (A, G, A, and T), three 2-mers (AG, GA, AT), two 3-mers (AGA and GAT) and one 4-mer (AGAT). More generally, a sequence of length L will have L−k+1 k-mers and $n^k$ total possible k-mers, where n is the number of possible monomers (e.g. four in the case of DNA). In some embodiments, k-mers of a specific length k within the nucleic acid sequence 126 of the fragment 124 are used, rather than using k-mers of all possible lengths within the sequence. In some alternative embodiments, the corresponding nucleic acid sequence is a plurality of residues, that is the linear order of the entire sequence of the fragment, rather than subsequences of the sequence of the fragment.

Referring to Block 528, in some embodiments, the autoencoder is a deep recurrent autoencoder and the training the autoencoder, for a respective sequence read in a corresponding plurality of sequence reads in the first training dataset feeds a first track of the deep recurrent autoencoder the corresponding nucleic acid sequence of the respective nucleic acid methylation fragment broken up into a plurality of k-mers, and feeds a second track of the deep recurrent autoencoder the corresponding methylation pattern of the respective nucleic acid methylation fragment.

In some embodiments, the autoencoder is a deep recurrent autoencoder and the training the autoencoder, for a respective nucleic acid methylation fragment in a corresponding plurality of nucleic acid methylation fragments in the first training dataset feeds a first track of the deep recurrent autoencoder the corresponding nucleic acid sequence of the respective nucleic acid methylation fragment on a residue basis, and feeds a second track of the deep recurrent autoencoder the corresponding methylation pattern of the respective nucleic acid methylation fragment.

In some embodiments, the autoencoder is provided, as input, both the corresponding methylation pattern and the corresponding nucleic acid sequence of a respective nucleic acid methylation fragment, and the autoencoder encodes latent representations comprising relational patterns between the corresponding methylation pattern and the genomic context of the corresponding methylation pattern. In some embodiments, the respective nucleic acid methylation sequence is mapped to a genomic location (e.g., by using a CpG index and/or aligning the corresponding nucleic acid sequence to a reference genome). In some embodiments, the mapping to a genomic location occurs prior to or subsequent to the training of the autoencoder. In some such embodiments, the corresponding nucleic acid sequence has at least a threshold length (e.g., a threshold number of CpGs and/or a threshold number of residues) such that the respective nucleic acid methylation sequence aligns to a single location in the reference genome. For example, in some such embodiments, the respective nucleic acid methylation fragment is greater than 50, greater than 100, greater than 150, or greater than 200 residues long. In some such embodiments, the respective nucleic acid methylation fragment comprises greater than 3, greater than 4, greater than 5, or greater than 6 CpG sites.

In some embodiments, the autoencoder is provided, as input, both the corresponding methylation pattern and the corresponding nucleic acid sequence of a respective nucleic acid methylation fragment, broken up into a plurality of k-mers, and the autoencoder encodes latent representations comprising relational patterns between the corresponding methylation pattern and one or more k-mers in the plurality of k-mers. In some embodiments, k is 3, 4, 5, 6, 7, 8, 9, 10, or more than 10. In some embodiments, the plurality of k-mers comprises k-mers of different lengths. In some embodiments, the plurality of k-mers comprises k-mers of the same length.

In some embodiments, the autoencoder is provided, as input, the genomic location of a corresponding methylation pattern of a respective nucleic acid methylation fragment, where the genomic location of the corresponding methylation pattern comprises one or more values of a CpG index.

As described above, referring again to Block 522, the reconstruction by the autoencoder of the input comprises reconstructing the corresponding methylation pattern and the corresponding nucleic acid sequence of the corresponding nucleic acid methylation fragment. In some embodiments, the reconstruction by the autoencoder 132 of the input comprises reconstructing the corresponding methylation pattern or the corresponding nucleic acid sequence of the corresponding nucleic acid methylation fragment.

As described above, referring again to Block 522, training the autoencoder comprises the evaluating a first error function for an error in the reconstruction (e.g., reconstruction loss) by the autoencoder of the corresponding methylation pattern and the corresponding nucleic acid sequence of the corresponding nucleic acid methylation fragment, thereby forming a trained autoencoder.

In some embodiments, for each respective nucleic acid methylation fragment, the reconstruction loss is evaluated across the entire fragment.

In some embodiments, the training the untrained autoencoder comprises backpropagation of the embeddings values in the embeddings layer. For example, in some general embodiments of machine learning (e.g., deep learning), backpropagation is a method of training a network with hidden layers (e.g. such as autoencoder 132) comprising a plurality of weights (e.g., embeddings). The output of an untrained model (e.g., the reconstruction by untrained autoencoder) is generated using a set of arbitrarily selected initial weights. The output is then compared with the original input (e.g., the corresponding methylation pattern and the corresponding nucleic acid sequence of the respective nucleic acid methylation fragment) and the error is computed (e.g., using a loss function). The weights are then updated such that the error is minimized (e.g., according to the loss function). In some embodiments, any one of a variety of backpropagation algorithms and/or methods are used to update the first and second plurality of weights, as will be apparent to one skilled in the art.

In some embodiments, the training the autoencoder forms a trained autoencoder following a first evaluation of a first error function. In some such embodiments, the training the autoencoder forms a trained autoencoder following a first updating of the plurality of embeddings based on a first evaluation of a first error function. In some alternative embodiments, the training the autoencoder forms a trained autoencoder following at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of the first error function. In some such embodiments, the training the autoencoder forms a trained autoencoder following at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million updatings of the plurality of embeddings based on the at least 1, at least 2, at least 3, at least 4, at least 5, at least 6, at least 7, at least 8, at least 9, at least 10, at least 20, at least 30, at least 40, at least 50, at least 100, at least 500, at least 1000, at least 10,000, at least 50,000, at least 100,000, at least 200,000, at least 500,000, or at least 1 million evaluations of the first error function.

Referring to Block 530, in some embodiments, the training the untrained autoencoder comprises evaluating the first error function for an error in the reconstruction by the autoencoder in accordance with a gradient descent algorithm. See, for example, Nguyen et al., 2019, "On the Dynamics of Gradient Descent for Autoencoders," Proceedings of the 22nd International Conference on Artificial Intelligence and Statistics (AISTATS) 2019, Naha, Okinawa, Japan. PMLR: Volume 89, which is hereby incorporated by reference.

In some embodiments, the training the autoencoder forms a trained autoencoder when the autoencoder satisfies a minimum performance requirement. For example, referring to Block 532, in some embodiments, the error calculated for the trained autoencoder across the first training dataset satisfies an error threshold. In some embodiments, the error calculated by the first error function across the first training dataset satisfies an error threshold when the error is less than five percent. In some embodiments, the error calculated by the first error function across the first training dataset satisfies an error threshold when the error is less than 20 percent, less than 18 percent, less than 15 percent, less than 10 percent, less than 5 percent, or less than 3 percent.

Processing of Second Training Dataset

Referring to Block 534, some embodiments of the systems and methods of the present disclosure obtain a second training dataset 120-2, in electronic form. The second training dataset comprises, for each respective subject in a second plurality of training subjects, a corresponding methylation pattern and a corresponding nucleic acid sequence of each respective nucleic acid methylation fragment in a corresponding plurality of nucleic acid methylation fragments determined by a methylation sequencing of nucleic acids in a biological sample obtained from the respective subject. The corresponding methylation pattern comprises a methylation state of each respective CpG site in a corresponding plurality of CpG sites e.g., two or more sites, three or more sites, four or more sites, five or more sites, six or more sites, seven or more sites, eight or more sites, nine or more sites, 10 or more sites, 11 or more sites, 12 or more sites, 13 or more sites, 14 or more sites, or 15 or more sites) in the respective nucleic acid methylation fragment, and each training subject in the second plurality of training subjects has the second cancer state.

In some embodiments, the methylation sequencing of nucleic acids in a biological sample obtained from the respective subject of the second training dataset 120-2 is methylation sequencing of cell-free nucleic acids in the biological sample. In some embodiments, the biological sample is a blood sample. In some embodiments, the biological sample comprises blood, whole blood, plasma, serum, urine, cerebrospinal fluid, fecal, saliva, sweat, tears, pleural fluid, pericardial fluid, or peritoneal fluid of the test subject.

In some embodiments, the respective biological sample for the second dataset is homogenous for the second cancer state. In some embodiments, the respective biological sample for the second dataset is a tumor sample that is homogenous for the second cancer state. In some embodiments, the respective biological sample for the second dataset is non-homogenous for the second cancer state. In some embodiments, the respective biological sample for the second dataset is a cfDNA sample that is non-homogenous for the second cancer state.

In some embodiments, the respective biological sample of the second training dataset is the same type of sample (e.g., liquid or tissue) as the respective biological sample of the first training dataset.

In some embodiments, the respective biological sample of the second training dataset 120-2 is a different type of sample (e.g., liquid or tissue) as the respective biological sample of the first training dataset 120-1.

Referring to Block 536, in some embodiments, the corresponding plurality of nucleic acid methylation fragments determined by methylation sequencing of nucleic acids in a biological sample obtained from the respective subject in the first training dataset or the second training dataset comprises one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments.

Referring to Block 538, in some embodiments, the second plurality of training subjects comprises 30 or less, 50 or less, 100 or less, or 1000 or less training subjects. In some embodiments, the first training dataset data is available from larger numbers of subjects than the second training dataset and the disclosed systems and methods advantageously make use of the data that is more readily available (the first dataset) to train the autoencoder and then use the trained autoencoder to find features within the data that is less readily available (the second dataset) that can be used to develop a classifier to discern the cancer state associated with the second dataset (e.g., to discriminate between the first cancer state and the second cancer state, where the first cancer state is represented by the first dataset and the second cancer state is represented by the second cancer state).

In some embodiments, the second training dataset is obtained using any of the methods, test subjects, biological samples, and/or sequencing methods disclosed herein (e.g., using any of the methods and/or embodiments described for the first training dataset).

In some embodiments, the disclosed systems and methods, after obtaining the second training dataset and prior to the using the second training dataset, filter each corresponding plurality of nucleic acid methylation fragments of the second training dataset by removing, from the corresponding plurality of nucleic acid methylation fragments, each respective nucleic acid methylation fragment that fails to satisfy one or more selection criteria.

In some embodiments, the same filtering criterion that were applied to the first training dataset described above are applied to the second training dataset.

In some embodiments, the respective nucleic acid methylation fragment fails to satisfy a selection criterion in the one or more selection criteria when the methylation pattern of the respective nucleic acid methylation fragment has an output p-value that fails to satisfy a p-value threshold, where the p-value of the respective nucleic acid methylation fragment is determined, at least in part, based upon a comparison of the methylation pattern of the respective nucleic acid methylation fragment over a plurality of CpG sites of the respective nucleic acid methylation fragment to a corresponding distribution of methylation patterns of those nucleic acid methylation fragments in the first training dataset that have the corresponding plurality of CpG sites.

In some embodiments, the respective nucleic acid methylation fragment fails to satisfy a selection criterion in the one or more selection criteria when the methylation pattern of the respective nucleic acid methylation fragment has an output p-value that fails to satisfy a p-value threshold, where the p-value of the respective nucleic acid methylation fragment is determined, at least in part, based upon a comparison of the methylation pattern of the respective nucleic acid methylation fragment over a plurality of CpG sites of the respective nucleic acid methylation fragment to a corresponding distribution of methylation patterns of those nucleic acid methylation fragments in the second training dataset that have the corresponding plurality of CpG sites.

In some embodiments, the respective nucleic acid methylation fragment from the second training dataset fails to satisfy a selection criterion in the one or more selection criteria when a p-value of a trained Markov model, responsive to input of the methylation pattern of the respective nucleic acid methylation fragment, fails the selection criterion, and the trained Markov model is trained, at least in part, based upon evaluation of a methylation state of each CpG site in a plurality of CpG sites of the respective nucleic acid methylation fragment across those nucleic acid methylation fragments in the first training dataset that have the corresponding plurality of CpG sites.

In some embodiments, the respective nucleic acid methylation fragment from the second training dataset fails to satisfy a selection criterion in the one or more selection criteria when a p-value of a trained Markov model, responsive to input of the methylation pattern of the respective nucleic acid methylation fragment, fails the selection criterion, and the trained Markov model is trained, at least in part, based upon evaluation of a methylation state of each CpG site in a plurality of CpG sites of the respective nucleic acid methylation fragment across those nucleic acid methylation fragments in the second training dataset that have the corresponding plurality of CpG sites.

In some such embodiments, the p-value is between 0.00001 and 0.20. In some embodiments the p-value is between 0.0010 and 0.00020. In some embodiments the p-value is between 0.0010 and 0.01. In some embodiments the p-value is between 0.01 and 0.05. In some embodiments the p-value is between 0.05 and 0.2.

In some embodiments, the respective nucleic acid methylation fragment fails to satisfy a selection criterion in the one or more selection criteria when the respective nucleic acid methylation fragment has less than a threshold number of CpG sites. In some such embodiments, the threshold number of CpG sites is 4, 5, 6, 7, 8, 9, 10, 11, 12, 13, 14, or 15. In some embodiments, the threshold number of CpG sites is determined (e.g., as a hyperparameter) based at least in part on a requirement that each possible methylation pattern of each respective nucleic acid methylation fragment has a threshold likelihood of occurrence (e.g., a likelihood of $\frac{1}{8}$ for a sequence of 3 CpG sites, a likelihood of $\frac{1}{32}$ for a sequence of 5 CpG sites, etc.).

In some embodiments, the respective nucleic acid methylation fragment fails to satisfy a selection criterion in the one or more selection criteria when the respective nucleic acid methylation fragment has less than a threshold number of residues. For example, in some embodiments, each respective nucleic acid methylation fragment has a length in residues (e.g., base pairs and/or k-mers) that is independent of the number of CpG sites in the respective nucleic acid methylation fragment. Thus, in some embodiments, a selection criterion applies a minimum length requirement to the plurality of nucleic acid methylation fragments prior to anomaly detection. In some embodiments, the threshold number of residues is 32 or 64. In some embodiments, the threshold number of residues is a fixed value between 20 and 90. In some embodiments, the threshold number of residues is greater than 90, greater than 100, greater than 150, or greater than 200.

In some embodiments, the threshold number of residues is determined (e.g., as a hyperparameter) based at least in part on a requirement that the nucleic acid sequence of each respective nucleic acid methylation fragment maps to less than a threshold number of locations in a reference genome. In some preferred embodiments, the threshold number of residues is determined based on a requirement that the nucleic acid sequence of each respective nucleic acid methylation fragment maps to a single location in a reference genome.

In some embodiments, the filtering removes a nucleic acid methylation fragment in the plurality of nucleic acid methylation fragments of the second dataset that has the same corresponding methylation pattern and the same corresponding nucleic acid sequence as another nucleic acid methylation fragment in the plurality of nucleic acid methylation fragments.

In some embodiments, the filtering retains a nucleic acid methylation fragment in the plurality of nucleic acid methylation fragments that has the same corresponding methylation pattern and a different corresponding nucleic acid sequence as another nucleic acid methylation fragment in the plurality of nucleic acid methylation fragments.

In some embodiments, the filtering of the second training dataset retains a nucleic acid methylation fragment in the plurality of nucleic acid methylation fragments that has a different corresponding methylation pattern and a same corresponding nucleic acid sequence as another nucleic acid methylation fragment in the plurality of nucleic acid methylation fragments.

In some embodiments, the filtering of the second training dataset removes nucleic fragments that map onto a blacklist of known noisy genomic positions. In some embodiments the blacklist is all or a portion of the ENCODE blacklist. See Ameniya et al. 2019, "The ENCODE Blacklist: Identification of Problematic Regions of the Genome," Scientific Reports 9, article number 9354.

In a particular embodiment, the nucleic acid methylation fragment fails to satisfy a selection criterion in the one or more selection criteria when the respective nucleic acid methylation fragment has less than a threshold number of CpG sites. Further, in these particular embodiments, the obtaining the second training dataset pads each nucleic acid methylation fragment in the corresponding plurality of nucleic acid methylation fragments that is less than a predetermined length to be the predetermined length prior to training the autoencoder. Further, in these particular embodiments the obtaining the second training dataset truncates each respective nucleic acid methylation fragment in the corresponding plurality of nucleic acid methylation fragment that is greater than the predetermined length by windowing across the respective nucleic acid methylation fragment with a predetermined stride, thereby breaking the respective nucleic acid methylation fragment into two or more sequence segments. Each sequence segment in the two or more sequence segments has the predetermined length and at least the threshold number of CpG sites. The two or more sequence segments collectively replace the respective nucleic acid methylation fragment in the corresponding plurality of nucleic acid methylation fragments as input to the using of the second training dataset. In some such embodiments, the stride is between 90 and 300 nucleotides. In some embodiments, the stride is 100, 128, or 256 nucleotides.

In some embodiments, the obtaining the second training dataset truncates a first nucleic acid methylation fragment in the corresponding plurality of nucleic acid methylation fragment, which is longer than a predetermined length, at a site of variance, conflicting methylation call, or ambiguous call within the first nucleic acid methylation fragment, thereby shortening the first nucleic acid methylation fragment to terminate at the site.

In some embodiments, the second training dataset is processed using any of the methods disclosed herein (e.g., using any of the methods and/or embodiments described for the first training dataset). In some embodiments, the filtering and/or preprocessing of the second training dataset is performed in any order, combinations, and/or with any modifications as will be apparent to one skilled in the art.

For example, FIG. 3 illustrates a flowchart of an example method for obtaining and processing a second training dataset, in accordance with some preferred embodiments. Referring to Block 302, the method comprises obtaining a second plurality of biological samples from a second training cohort having a second label. Referring to Block 304, the second plurality of sequence reads of cell-free nucleic acids from corresponding subjects in the second training cohort are obtained using whole-genome or targeted methylation sequencing. Referring to Block 306, the nucleic acid sequence and the methylation pattern for each fragment in a second plurality of fragments are determined from the second plurality of sequence reads. See, for example, United States Patent Publication No. US 2019-0287652 A1, entitled "Anomalous Fragment Detection and Classification," United States Patent Publication No. US 2020-0239964 A1 entitled "Anomalous Fragment Detection and Classification," and United States Patent Publication No. US 2020-0239965 A1, entitled "Source of Origin Deconvolution Based on Methylation Fragments in Cell-Free DNA Samples," each of which is hereby incorporated by reference, for methods on determining methylation patterns of sequence reads. Referring to Block 308, fragments in the second plurality of fragments are optionally split at variant positions, positions for which the 3' and 5' paired-end reads conflict, and/or ambiguous positions. Referring to Block 310, fragments that have less than a threshold number of CpG sites (less than 3 sites, less than 4 sites, less than 5 sites, less than 6 sites, less than 7 sites, less than 8 sites, less than 9 sites, less than 10 sites, less than 11 sites, less than 12 sites, less than 13 sites, less than 14 sites, less than 15 sites, less than 20 sites, less than 30 sites, less than 50 sites) are discarded in some embodiments. Referring to Block 312, all fragments from the second plurality of fragments that have both the same nucleic acid sequence and the same CpG methylation pattern are removed in some embodiments. Referring to Block 314, one or more second threshold filters is optionally applied to each respective fragment in the second plurality of fragments by comparing the methylation pattern of the respective fragments to the observed methylation patterns in the second plurality of fragments to compute a likelihood of occurrence of the methylation pattern for each of the respective fragments, thereby filtering out fragments from the second plurality of fragments that fail to satisfy a second threshold value (e.g. fail to have a p-value that is lower than a particular threshold value) of the second threshold filter. See, for example, FIG. 4 which illustrates how to compute a p-value for a particular methylation pattern based on the methylation patterns exhibited by a plurality of fragments. While FIG. 4 is directed to using a plurality of fragments drawn from the first training dataset, the principles disclosed in FIG. 4 can likewise be applied to determining the p-value of the methylation pattern of a fragment using a plurality of fragments drawn from the second training dataset. Referring to Block 316, a fragment error score for each fragment in the second plurality of fragments is obtained using the autoencoder 132 that was previously training using the first training dataset. Referring to Block 318, a third plurality of fragments in the second plurality of fragments that satisfy an encoder-decoder model error threshold is selected. Referring to Block 320, the methylation pattern and nucleic acid sequence fragments in the third plurality of fragments are used to train a classifier to discriminate the specified disease condition.

In some embodiments, the using the second training dataset and the trained autoencoder uses as input for the trained autoencoder a dataset comprising a plurality of nucleic acid methylation fragments and/or sequence segments of the second training dataset 120-2, after any desired preprocessing and/or filtering of the second training dataset as described in the present disclosure. In some embodiments, the using the second training dataset and the trained autoencoder uses a dataset that is different from the second training dataset initially obtained, as determined by a methylation sequencing of nucleic acids in a biological sample from a respective subject.

Methylation Fragment Reconstruction Scores

Referring to Block 540, the method further comprises using the second training dataset 120-2 and the trained autoencoder 132 to identify a plurality of features 146 from among a plurality of sequences or a plurality of methylation patterns represented by the second training dataset, by computing, for each respective nucleic acid methylation fragment in each corresponding plurality of nucleic acid methylation fragments in the second training dataset, a corresponding score determined at least in part by a reconstruction of the corresponding methylation pattern of the respective nucleic acid methylation fragment by the autoencoder 132 upon inputting the corresponding methylation pattern and the corresponding nucleic acid sequence of the respective nucleic acid methylation fragment into the trained autoencoder.

For example, in some embodiments, the trained autoencoder trained on the first training dataset 120-1 reconstructs the corresponding methylation pattern of a respective nucleic acid methylation fragment from the second training dataset (e.g., a test or unknown sample). The reconstruction of the fragment from the second training dataset is scored based on the accuracy of the reconstruction (e.g., using a loss function and/or a methylation fragment reconstruction score (MFRS)). Each respective reconstruction score for each nucleic acid methylation fragment in the second training dataset is assessed based on the similarity to the reconstruction scores of the training dataset (e.g., via raw score values and/or a histogram plot of the distribution of scores). In some such embodiments, one or more nucleic acid methylation fragments having a higher score is therefore deemed to have a higher error in the reconstruction, and therefore is considered to be anomalous.

Figure 6:
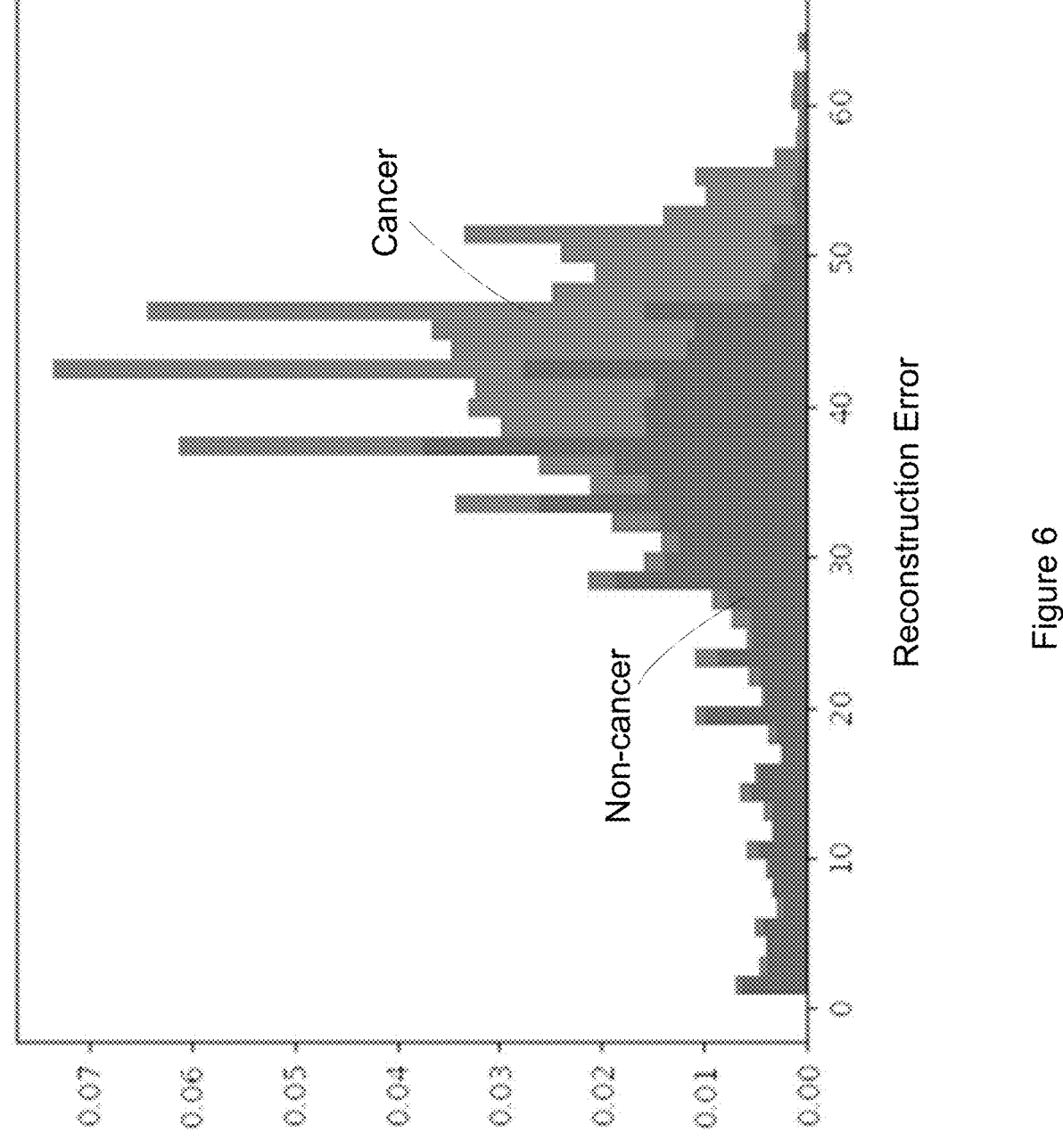
FIG. 6 illustrates an example of methylation pattern anomaly detection using autoencoders, in accordance with some embodiments of the present disclosure.
Figure 11:
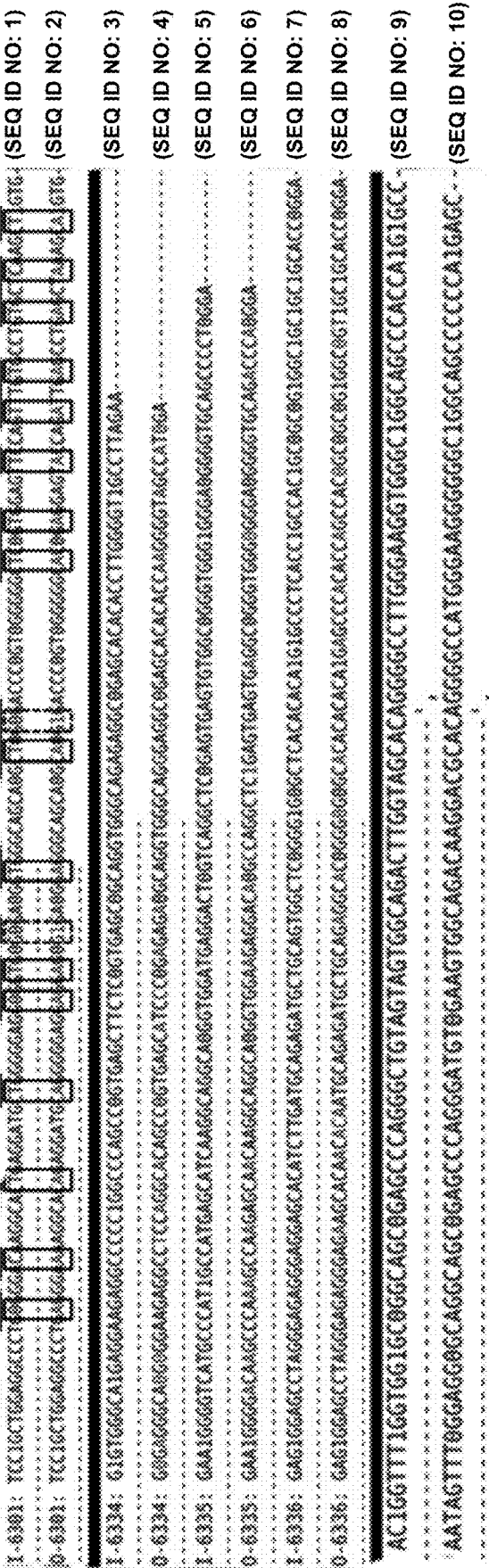
FIG. 11 illustrates example input and output nucleic acid sequences for nucleic acid methylation fragments, in accordance with some embodiments of the present disclosure, where "I" indicates input nucleic acid sequences before encoding by the encoder, and "O" indicates output nucleic acid sequences after reconstruction by the decoder.

FIGS. 11 and 6 illustrate example reconstruction output produced by an autoencoder 132. Specifically, FIG. 11 illustrates example input and output nucleic acid sequences for a plurality of nucleic acid methylation fragments, in accordance with some embodiments of the present disclosure. "I" indicates input into the encoder 132 (e.g., corresponding nucleic acid sequences and corresponding methylation patterns for a plurality of nucleic acid methylation fragments), while "O" indicates output from the decoder (e.g., reconstructions). Letters A, G, C, and T indicate nucleotide bases and numbers 0 and 1 indicate unmethylated and methylated states, respectively. Boxes indicate errors in the reconstruction, where dashed lines highlight errors in methylation pattern reconstruction, and solid lines highlight errors in nucleic acid sequence reconstruction.

FIG. 6 illustrates an example of sample-level methylation pattern anomaly detection using the corresponding reconstruction scores determined after reconstruction by an autoencoder 132, in accordance with some embodiments of the present disclosure. Each histogram in FIG. 6 shows the distribution of reconstruction error scores from two test samples, one that has cancer and one that does not have cancer) used as input into a trained autoencoder trained on a non-cancer training dataset, where the x-axis denotes the reconstruction error score and the y-axis denotes the normalized number of fragments with the respective reconstruction error score. The dark gray histogram shows a reconstruction error profile for a non-cancer test sample. The light gray histogram shows a reconstruction error profile for a cancer test sample. Each test sample comprises a respective plurality of nucleic acid methylation fragments. As depicted in FIG. 6, the distribution of reconstruction error scores from the cancer test sample reveals a greater number of nucleic acid methylation fragments with high (e.g., greater than 40) reconstruction error scores compared to the non-cancer distribution. Thus, when using an autoencoder trained on a non-cancer training dataset, fragments with high reconstruction error scores in comparison to the non-cancer distribution are deemed anomalous.

In some embodiments, the corresponding score is determined by the reconstruction of the corresponding methylation pattern of the respective nucleic acid methylation fragment by the autoencoder 132 upon inputting the corresponding methylation pattern and the corresponding nucleic acid sequence of the respective nucleic acid methylation fragment into the trained autoencoder. In some embodiments, the corresponding score is determined by the reconstruction of the corresponding methylation pattern and the corresponding nucleic acid sequence of the respective nucleic acid methylation fragment by the autoencoder upon inputting the corresponding methylation pattern and the corresponding nucleic acid sequence of the respective nucleic acid methylation fragment into the trained autoencoder.

Referring to Block 542, in some embodiments, the corresponding score for a respective nucleic acid methylation fragment is determined by the correctness of the reconstruction of the corresponding methylation pattern of the respective nucleic acid methylation fragment by the autoencoder, and is independent of the correctness of the reconstruction of the corresponding nucleic acid sequence of the respective nucleic acid methylation fragment by the autoencoder. In other words, the score in such embodiments is not dependent on how well the autoencoder reconstructs the nucleic acid sequence of input fragment but rather is just dependent on how well the autoencoder reconstructs the methylation pattern of input fragment. In fact, in such embodiments it is possible that the autoencoder makes no attempt to reconstruct the sequence of the input nucleic acid fragment at all since it is not used in the scoring in such embodiments. In fact, in some such embodiments, the autoencoder is not trained on the sequences of the fragments of the first training set since nucleic acid sequence reconstruction does not form a basis of the fragment scoring in such embodiments.

Referring to Block 544, in some embodiments, the corresponding score for a respective nucleic acid methylation fragment is determined by the correctness of the reconstruction of the corresponding methylation pattern of the respective nucleic acid methylation fragment by the autoencoder, and is further determined by the correctness of the reconstruction of the corresponding nucleic acid sequence of the respective nucleic acid methylation fragment by the autoencoder. In other words, in such embodiments, the corresponding score for the respective nucleic acid methylation fragment is a function of both the correctness of the reconstruction of the corresponding methylation pattern of the respective nucleic acid methylation fragment by the auto-encoder (A) and the correctness of the reconstruction of the corresponding nucleic acid sequence of the respective nucleic acid methylation fragment by the autoencoder (B). In some embodiments this function is the simple summation of A and B to arrive at the corresponding score.

In some embodiments the function is the weighted combination $x_1A+x_2B$, where A is weighed by $x_1$ and B is weighted by $x_2$, and $x_1$ and $x_2$ are independent of each other. In some such nonlimiting embodiments, $x_1$ and $x_2$ are each in the range of 0 to 1 inclusive. In some such nonlimiting embodiments, $x_1$ and $x_2$ are each not zero.

In some embodiments the function is the weighted combination $x_1A*x_2B$, where A is weighed by $x_1$ and B is weighted by $x_2$, and $x_1$ and $x_2$ are independent of each other. In some such nonlimiting embodiments, $x_1$ and $x_2$ are each in the range of 0 to 1 inclusive. In some such nonlimiting embodiments, $x_1$ and $x_2$ are each not zero.

In some embodiments the function is the weighted combination $(x_1A÷x_2B)$ or $(x_2B÷x_1A)$, where A is weighed by $x_1$ and B is weighted by $x_2$, and $x_1$ and $x_2$ are independent of each other. In some such nonlimiting embodiments, $x_1$ and $x_2$ are each in the range of 0 to 1 inclusive. In some such nonlimiting embodiments, $x_1$ and $x_2$ are each not zero.

In some embodiments the function is a weighted logarithmic combination $\log(x_1A+x_2B)$ or $\log(x_1A*x_2B)$, where log is to any base (e.g., 10, 2, or is a natural logarithm), A is weighed by $x_1$ and B is weighted by $x_2$, and $x_1$ and $x_2$ are independent of each other. In some such nonlimiting embodiments, $x_1$ and $x_2$ are each real values are each in the range of 0 to 1 inclusive. In some such nonlimiting embodiments, $x_1$ and $x_2$ are each not zero.

In some such embodiments, the correctness of the reconstruction of the corresponding methylation pattern of the respective nucleic acid methylation fragment is determined, at least in part, by the Hamming distance between the reconstruction of the corresponding methylation pattern of the respective nucleic acid methylation fragment and the actual methylation pattern of the respective nucleic acid methylation fragment. For example, in some embodiments, the Hamming distance for two methylation patterns is calculated as a sum of the number of positions at which the methylation states in the reconstruction differ from the methylation states in the original input fragment. For instance, consider the example input methylation pattern 11011001, where each "1" corresponds to a methylated CpG site and each "0" corresponds to an unmethylated CpG site. Suppose that the autoencoder 132 returns the string 10011101. To compute the Hamming distance, the input and output strings are combined as $11011001⊕10011101=01000100$. Since 01000100 contains two 1s, the Hamming distance, d(11011001, 10011101) is 2 in this example. In some embodiments, the correctness of the reconstruction of the corresponding methylation pattern of the respective nucleic acid methylation fragment is determined, at least in part, by the Levenshtein distance between the reconstruction of the corresponding methylation pattern of the respective nucleic acid methylation fragment and the actual methylation pattern of the respective nucleic acid methylation fragment.

In some embodiments, the corresponding score for the respective nucleic acid methylation fragment is constrained to be between a first number and a second number. In some such embodiments, the first number is zero and the second number is one. For instance, in some such embodiments, the Hamming distance is normalized by the number of CpG sites in the input string. In the above example, $11011001⊕10011101=01000100$, the Hamming distance of 2 would be divided by 8 in order to normalize for 8 CpG sites so that the normalized score is ⅜ or 0.25.

Referring to Block 546, in some embodiments, the corresponding score is computed using the first error function (e.g., the first error function used for training the untrained autoencoder). Referring to Block 548, in some embodiments, the corresponding score for a respective nucleic acid methylation fragment is computed using a second error function that is different than the first error function.

In some embodiments, for each respective nucleic acid methylation fragment, the corresponding score is computed using a first or a second error function that is computed across the entire fragment.

In some embodiments, the corresponding score is computed using a loss function. In some such embodiments, the loss function includes but is not limited to a cross-entropy loss function, a hinge loss function, a Huber loss function, a Kullback-Leibler loss function, a Euclidean distance log function, an element-wise KL Divergence, a mean absolute error or L1 loss function, and/or a mean squared error or L2 loss function.

In some embodiments, the corresponding score for a respective nucleic acid methylation fragment is computed by the autoencoder 132 as:

$$A(f)=\text{Loss}(f,f')$$

where f is the corresponding methylation pattern of the respective nucleic acid methylation fragment, f' is a reconstruction of the corresponding methylation pattern of the respective nucleic acid methylation fragment by the autoencoder upon inputting the corresponding methylation pattern and the corresponding nucleic acid sequence of the respective nucleic acid methylation fragment into the autoencoder, and Loss is a loss between f and f' (e.g., the methylation reconstruction error).

In some such embodiments, Loss is a reconstruction error between f and f', a Hamming distance between f and f', a cross entropy loss between f and f', a mean squared error between f and f', or a mean absolute error between f and f'.

In some embodiments, the corresponding score is a sum of the reconstruction error and a distance measure.

For example, in some embodiments, the corresponding score for a respective nucleic acid methylation fragment is computed as:

$$A(f)=w_1*\text{Loss}(f,f')+w_2*\text{Distance}[E(f),E(f\_NC)]$$

where $w_1$ is a first weight, f is the corresponding methylation pattern of the respective nucleic acid methylation fragment, f' is a reconstruction of the corresponding methylation pattern of the respective nucleic acid methylation fragment by the autoencoder upon inputting the corresponding methylation pattern and the corresponding nucleic acid sequence of the respective nucleic acid methylation fragment into the autoencoder, $w_2$ is a second weight, Loss is a loss between f and f', E(f) is an encoding produced by the autoencoder upon inputting the corresponding methylation pattern of the respective nucleic acid methylation fragment into the autoencoder, f_NC is a methylation pattern and nucleic acid sequence of a nucleic acid methylation fragment that localizes to the same genomic location as the respective nucleic acid methylation fragment and has the same sequence as the respective nucleic acid methylation fragment, E(f_NC) is an encoding produced by the autoencoder upon inputting f_NC into the autoencoder, and Distance is a distance measure or a similarity measure between E(f) and E(f_NC).

In some embodiments, Distance is a cosine distance, Levenshtein distance, Hamming distance, Euclidian distance, Manhattan distance, Jaccard distance, correlation distance, Chi-square distance, or Mahalanobis distance.

In some embodiments, $w_1$ and $w_2$ each have a value of 1. In some embodiments, $w_1$ and $w_2$ each have a different value. In some embodiments, $w_1$ and $w_2$ each have a different real value between 0 and 1 inclusive.

Identification of Features

In some preferred embodiments, the plurality of features comprises one or more nucleic acid methylation fragments that have a high likelihood of being representative (e.g., discriminative) for a cancer condition (e.g., of a first or a second cancer condition). In some such embodiments, the plurality of features comprises one or more nucleic acid methylation fragments that are determined to be anomalous based in part by the reconstruction error (e.g., MFRS) of the one or more nucleic acid methylation fragments. In some such embodiments, the plurality of features comprises two or more, three or more, 10 or more, 15 or more 20 or more, 50 or more or 100 or more nucleic acid methylation fragments that are determined to be anomalous based in part by the reconstruction error (e.g., MFRS) of the one or more nucleic acid methylation fragments. In some embodiments, some or all of the features uniquely map to a genomic region described in International Patent Publication No. WO2020154682A3, entitled "Detecting Cancer, Cancer Tissue or Origin, or Cancer Type," which is hereby incorporated by reference, including the Sequence Listing referenced therein. In some embodiments, some or all of the probes uniquely map to a genomic region described in International Patent Publication No. WO2020/069350A1, entitled "Methylated Markers and Targeted Methylation Probe Panel," which is hereby incorporated by reference, including the Sequence Listing referenced therein. In some embodiments, some or all of the probes uniquely map to a genomic region described in International Patent Publication No. WO2019/195268A2, entitled "Methylated Markers and Targeted Methylation Probe Panels," which is hereby incorporated by reference, including the Sequence Listing referenced therein.

Referring to Block 550 of FIG. 5D, in some embodiments, each nucleic acid sequence represented by the second dataset that corresponds to one or more nucleic acid methylation fragments in the second dataset receiving a corresponding score that satisfies an error threshold is identified as a feature in the plurality of features. For example, in some such embodiments, a feature in the plurality of features is the corresponding nucleic acid sequence of a respective nucleic acid methylation fragment that is determined to be anomalous based on the reconstruction error of the corresponding methylation pattern.

In some embodiments, a corresponding score (e.g., MFRS) satisfies an error threshold when the corresponding score is greater than 30, greater than 40, greater than 50, greater than 60, or greater than 70. In some embodiments, a corresponding score satisfies an error threshold when the error is greater than 80 percent, greater than 82 percent, greater than 85 percent, greater than 90 percent, greater than 95 percent, or greater than 97 percent.

In some embodiments, a corresponding score satisfies an error threshold when the corresponding score is greater than the score of 80 percent or more, 85 percent or more, 90 percent or more, 95 percent or more, 98 percent or more or 99 percent or more of the unique nucleic acid methylation fragments in the training dataset 120-2.

In some embodiments, a feature in the plurality of features is selected based at least in part on a ranking of a corresponding score and/or a ranking of an error in the reconstruction.

For example, referring to Block 552, in some embodiments, the using the second training dataset and the trained autoencoder to identify a plurality of features selects a methylation pattern associated with a corresponding score on the basis that it is in the top N corresponding scores (e.g., achieved by the computing) as a feature in the plurality of features. In some such embodiments, N is between 100 and 2000. In some embodiments, N is 1000.

In some embodiments, the using the second training dataset and the trained autoencoder to identify a plurality of features selects a methylation pattern associated with a corresponding score on the basis of the position of the corresponding score in a first distribution of corresponding scores (e.g., a histogram). In some such embodiments, the position of the corresponding score in a first distribution of corresponding scores is compared against a second distribution of corresponding scores. See, for example, FIG. 6.

In some embodiments, a feature in the plurality of features is a characteristic of a respective one or more nucleic acid methylation fragments, other than the corresponding nucleic acid sequences of the respective one or more nucleic acid methylation fragments.

In some such embodiments, a feature in the plurality of features includes but is not limited to the encodings (e.g., the values of the embeddings layer) of a respective nucleic acid methylation fragment that is determined to be anomalous based on the reconstruction error of the corresponding methylation pattern, the combined (e.g., concatenated) encodings of the plurality of nucleic acid methylation fragments that are determined to be anomalous based on the reconstruction errors of the corresponding plurality of methylation patterns, and/or the combined (e.g., concatenated) encodings of all the nucleic acid methylation fragments in the second training dataset.

In some embodiments, a feature in the plurality of features includes but is not limited to the reconstruction score (e.g., the MFRS and/or the error) of a respective nucleic acid methylation fragment that is determined to be anomalous based on the reconstruction error of the corresponding methylation pattern, the combined (e.g., concatenated) reconstruction scores of the plurality of nucleic acid methylation fragments that are determined to be anomalous based on the reconstruction errors of the corresponding plurality of methylation patterns, and/or the combined (e.g., concatenated) reconstruction scores of all the nucleic acid methylation fragments in the second training dataset.

In some embodiments, a feature in the plurality of features includes but is not limited to all or a portion of the methylation pattern, the genomic location and/or the CpG index of one or more CpG sites in a respective nucleic acid methylation fragment that is determined to be anomalous based on the reconstruction error of the corresponding methylation pattern. For example, in some such embodiments, a feature in the plurality of features can include an association between a respective methylation pattern and a specific location in a reference genome.

In some preferred embodiments, a feature in the plurality of features includes one or more characteristics (e.g., a corresponding nucleic acid sequence and/or a corresponding methylation pattern) of a nucleic acid methylation fragment that aligns to a single location in a reference genome. In some such embodiments, the respective feature can provide greater discriminative power compared to, for example, a nucleic acid methylation fragment comprising a corresponding nucleic acid sequence that localizes to at least a first and a second location in a reference genome, where the corresponding methylation pattern at the first location is anomalous and the corresponding methylation pattern at the second location is not anomalous.

In some embodiments, a feature in the plurality of features is an MFRS for one or more CpG sites. In some such embodiments, a feature in the plurality of features is a parameter computed using a plurality of MFRS for one or more CpG sites across a plurality of nucleic acid methylation fragments. For example, in some embodiments, a feature is the average MFRS at one or more CpG sites, which can be used for classification purposes in a similar manner to a β-score or an M-score. See, for example, U.S. patent application Ser. No. 17/119,606, titled "Cancer Classification Using Patch Convolutional Neural Networks," filed Dec. 11, 2020. In some embodiments, one or more MFRS is used to create a sample-level feature vector. For example, in some embodiments, the MFRS is used as a replacement for fragment hypermethylation and/or hypomethylation in a sample-level feature vector.

In some embodiments, a nucleic acid sequence of a respective nucleic acid methylation fragment that is identified as a feature in the plurality of features is used to identify further characteristics for classification, including but not limited to the biological context of the nucleic acid methylation fragment. In some such embodiments, a nucleic acid sequence of a respective nucleic acid methylation fragment that is identified as a feature in the plurality of features is used, e.g., to select low noise regions, panel genes, and/or other informative regions.

Discriminating Cancer States

Referring to Block 554 of FIG. 5E, in some embodiments the systems and methods of the present disclose use the plurality of features identified above to train a supervised model 148 that discriminates between the first cancer state and the second cancer state.

Referring to Block 556, in some embodiments, the first cancer state is absence of cancer. Referring to Block 558, in some embodiments, the second cancer state is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the first cancer state is a first stage (e.g., stage I, II, III, or IV) of a specified cancer, and the second cancer state is a second stage (e.g., stage I, II, III, or IV and other than stage 1) of the specified cancer.

In some embodiments, the specified cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the second cancer state is a stage of adrenal cancer, a stage of biliary tract cancer, a stage of bladder cancer, a stage of bone/bone marrow cancer, a stage of brain cancer, a stage of breast cancer, a stage of cervical cancer, a stage of colorectal cancer, a stage of cancer of the esophagus, a stage of gastric cancer, a stage of head/neck cancer, a stage of hepatobiliary cancer, a stage of kidney cancer, a stage of liver cancer, a stage of lung cancer, a stage of ovarian cancer, a stage of pancreatic cancer, a stage of pelvis cancer, a stage of pleura cancer, a stage of prostate cancer, a stage of renal cancer, a stage of skin cancer, a stage of stomach cancer, a stage of testis cancer, a stage of thymus cancer, a stage of thyroid cancer, a stage of uterine cancer, a stage of lymphoma, a stage of melanoma, a stage of multiple myeloma, or a stage of leukemia.

In some embodiments, the first cancer state is a first tissue of origin, and the second cancer state is a second tissue of origin that is different from the first cancer state. In some embodiments, the first cancer state is a first type or subtype, and the second cancer state is a second type or subtype that is different from the first cancer state.

In some preferred embodiments, the first cancer state is absence of cancer (e.g., non-cancer or healthy) and the second cancer state is presence of cancer. In some such embodiments, the untrained autoencoder is trained (e.g., using backpropagation) using a first training dataset comprising a sufficient number of training samples (e.g., from a healthy cohort) to avoid overfitting. For example, in one exemplary embodiment, the first training dataset 120-1 comprises at least 10,000,000 fragments, at least 5, 6, 7, 8, 9, 10, 11, 12, 13, 14, or 15 methylation sites per fragment, and an average sequencing depth of between about 200× and 10,000×. In some embodiments, the average sequencing depth is around 100×, 200×, 500×, 1000×, 1500×, 2000×, 2500×, 3000×, 4000×, or 5000×. In some embodiments, the average sequencing depth is calibrated to account for effects for enrichment probes in a targeted methylation assay. For example, a sequencing depth of 150× in using enriched samples may equate to 500× or higher depth in un-enriched samples. In some further such embodiments, the second training dataset 120-2 is used with the trained autoencoder 132 to generate reconstruction scores (e.g., MFRS), and the nucleic acid sequences of poorly scored nucleic acid methylation fragments are selected as features to be used to train the supervised model 148, where the features are inputted into the classifier (supervised model 148) with labels indicating the respective cancer state. Such embodiments of the disclosed systems and methods are advantageous in that they improve the training of the supervised model 148 by limiting the input features used for training the supervised model 148 to the anomalous and thus highly discriminative features. In addition, such embodiments of the disclosed systems and methods are advantageous in that they do not require both the first and the second training dataset to comprise a high number of training samples, thus allowing for anomalous fragments to be identified for relatively rare cancer conditions (e.g., for the second training dataset 120-2).

In some embodiments, the disclosed systems and methods are used to identify biomarkers by identifying anomalous methylation patterns indicative of a cancer state. In some such embodiments, the cancer state is a specified type of cancer that lacks an existing screening test (e.g., lung cancer).

In some embodiments, the disclosed systems and methods are used to construct a unary classifier (e.g., X versus not-X) for a specified cancer state. In some such embodiments, the disclosed systems and methods are used to training a plurality of autoencoders. In such endeavors, a different respective training dataset in a plurality of training datasets is used to train a corresponding autoencoder, where the respective training dataset represents a particular cancer state in a plurality of cancer states, and where each trained autoencoder functions as a unary classifier for the corresponding cancer state. In some embodiments, 2, 3, 4, 5, 6, 7, 8, 9, 10, 11, 12, 13, 14, 15, or 16 autoencoders are trained, where each such respective autoencoder is trained to discriminate a different particular cancer state on a unary basis. In some embodiments, 2, 3, 4, 5, 6, 7, 8, 9, 10, 11, 12, 13, 14, 15, or 16 autoencoders are trained, where each such respective autoencoder is trained to discriminate between a different pair of cancer states (e.g., first and second cancer state, etc.)

In some embodiments, the disclosed systems and methods are used as a rapid screen to identify biological samples comprising anomalous fragments (e.g., a reflex model using an autoencoder trained on a non-cancer training dataset) for further investigation and/or analysis (e.g., further classification using a supervised model). In some such embodiments, this provides advantages by screening out samples that do not have the cancer state of interest, thus reducing the computational burden and effort required to run a plurality of downstream analyses.

Referring to Block 560 of FIG. 5E, in some embodiments, the using the plurality of features comprises using the corresponding score of each feature in the plurality of features to compute a corresponding CpG average reconstruction score for each CpG site in a second plurality of CpG sites found in the plurality of features, thereby computing a plurality of corresponding CpG average reconstruction scores. In some such embodiments, the plurality of corresponding CpG average reconstruction scores is used to select low noise regions in a reference genome, regions of a reference genome for targeted sequencing, or regions of the reference genome that are informative for discriminating between the first cancer state and the second cancer state.

For example, in some embodiments, the plurality of features are used to identify informative characteristics associated with a specified cancer state. Example of such informative characteristics include, but not limited to, transcription factor bindings, complex genomic rearrangements (CGRs) implicated in cancer and other diseases, alternative annotations and/or genome browser tracks, gene expression within or flanking the respective nucleic acid sequence, mutations, variant calling, low-depth information from whole-genome sequencing and/or WGBS (e.g., at 30x), high-depth information from targeted sequence and/or targeted methylation sequencing, contamination, and/or other biological context.

Supervised Models

Referring to Block 562 of FIG. 5E, in some embodiments, the supervised model 148 is a logistic regression model or a multinomial logistic regression algorithm. Logistic regression algorithms, including multivariate logistic regression, are disclosed in Agresti, *An Introduction to Categorical Data Analysis*, 1996, Chapter 5, pp. 103-144, John Wiley & Son, New York, which is hereby incorporated by reference.

Referring to Block 564 of FIG. 5E, in some embodiments, the supervised model 148 is a neural network algorithm (e.g., a convolutional neural network). Neural network algorithms, including convolutional neural network algorithms, are disclosed in See, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference.

In some embodiments, the supervised model 148 is a support vector machine algorithm. SVM algorithms are described in Cristianini and Shawe-Taylor, 2000, "An Introduction to Support Vector Machines," Cambridge University Press, Cambridge; Boser et al., 1992, "A training algorithm for optimal margin classifiers," in Proceedings of the 5$^{th}$ Annual ACM Workshop on Computational Learning Theory, ACM Press, Pittsburgh, Pa., pp. 142-152; Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y.; Duda, *Pattern Classification*, Second Edition, 2001, John Wiley & Sons, Inc., pp. 259, 262-265; and Hastie, 2001, *The Elements of Statistical Learning*, Springer, New York; and Furey et al., 2000, *Bioinformatics* 16, 906-914, each of which is hereby incorporated by reference in its entirety. When used for classification, SVMs separate a given set of binary labeled data training set (e.g., by tumor fraction value) with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space.

In some embodiments, the supervised model 148 is a Naive Bayes algorithm. The Naive Bayes algorithm is described in Taheri and Mammadov, "Learning the naive Bayes classifier with optimization models," International Journal of Applied Mathematics and Computer Science 23(4), 787-795, which is hereby incorporated by reference.

In some embodiments, the supervised model 148 is a nearest neighbor algorithm. Given a query point $x_0$, the k training points $x_{(r)}$, . . . , k closest in distance to $x_0$ are identified and then the point $x_0$ is classified using the k nearest neighbors. Ties can be broken at random. In some embodiments, Euclidean distance in feature space is used to determine distance as:

$$d_{(i)} = \|x_{(i)} - x_{(0)}\|$$

In some embodiments, when the nearest neighbor algorithm is used, the measurement data for the plurality of features 146 across the second dataset 120-2 used to compute the linear discriminant is standardized to have mean zero and variance 1. The plurality of features 146 $\{p_1, . . . , p_{N-K}\}$ represents the feature space into which reference entities of the second training set are plotted. In some embodiments, the nearest neighbor rule is refined to address issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc.; and Hastie, 2001, *The Elements of Statistical Learning, Springer*, New York, each of which is hereby incorporated by reference in its entirety.

In some embodiments, the supervised model 148 is a boosted trees algorithm, a random forest algorithm, or a decision tree algorithm. Decision trees are described generally by Duda, 2001, *Pattern Classification*, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can be used is a classification and regression tree (CART). Other specific decision tree algorithms include, but are not limited to, ID3, C4.5, MART, and Random Forests. CART, ID3, and C4.5 are described in Duda, 2001, *Pattern Classification*, John Wiley & Sons, Inc., New York, pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests—Random Features," Technical Report 567, Statistics Department, U.C. Berkeley, September 1999, which is hereby incorporated by reference in its entirety.

In some embodiments, the supervised model 148 is a linear model, such as a linear regression algorithm. Linear regression algorithms are described in Chapter 3 of Hastie et al., *The Elements of Statistical Learning, Data Mining, Inference, and Prediction*, Springer series in Statistics, Springer-Verlag, New York, which is hereby incorporated by reference.

In some embodiments, the supervised model is a gradient boosting machine. See, for example, Feng et al., 2020, "Soft Gradient Boosting Machine," arXiv:2006.04059, which is hereby incorporated by reference, for a general description of gradient boosting machines.

Supervised models (e.g., classifiers) are described in further detail in, e.g., U.S. Provisional patent application Ser. No. 17/119,606, entitled "Cancer classification using patch convolutional neural networks," filed Dec. 11, 2020, and United States Patent Publication No. US 2020-0385813 A1, entitled "Systems and Methods for Estimating Cell Source Fractions Using Methylation Information," each of which is hereby incorporated herein by reference in its entirety.

In some embodiments, the supervised model 148 is trained to predict a disease condition such as, for example, a cancer condition and/or a stage of a cancer condition from any of the cancer conditions described herein.

In some embodiments, any of the features described herein are used to train the supervised model (e.g., methylation patterns, nucleic acid sequences, reconstruction scores, MFRS, embeddings, alternative features and/or any combinations and/or modifications as will be apparent to one skilled in the art).

In some embodiments, a supervised model is trained for each respective cancer state in the plurality of cancer states described above (see, Discriminating Cancer States).

Referring to Block 566, in some embodiments, the supervised model is trained using (i) the methylation pattern of each respective nucleic acid methylation fragment in the plurality of features across the first and second plurality of training subjects and (ii) an indication for each respective nucleic acid methylation fragment as to whether the nucleic acid methylation fragment originates from a training subject with the first cancer state or a training subject with the second cancer state.

In some embodiments, the supervised model is a Kullback-Leibler distance between a first distribution and a second distribution, where the first distribution comprises a first plurality of corresponding scores for the plurality of features across the nucleic acid methylation fragments of the first training dataset or the second training dataset, and the second distribution comprises a second plurality of corresponding scores for a plurality of nucleic acid methylation fragments obtained from a biological sample of a test subject. For example, the Kullback-Leibler distance measures the divergence between the respective masses of a first and a second distribution (e.g., between the reconstruction and the original).

In some embodiments, the systems and methods of the present disclosure obtain a test dataset, in electronic form, where the test dataset comprises, for a test subject, a corresponding methylation pattern and a corresponding nucleic acid sequence of each respective nucleic acid methylation fragment in a plurality of test nucleic acid methylation fragments determined by a methylation sequencing of nucleic acids in a biological sample obtained from the test subject. In such embodiments, the corresponding methylation pattern comprises a methylation state of each respective CpG site in a corresponding plurality of CpG sites in the respective test nucleic acid methylation fragment. All or a portion of the test dataset is applied to the supervised model thereby obtaining a determination, from the supervised model, as to whether the test subject has the first cancer state or the second cancer state.

In some such embodiments, the test dataset is obtained and/or processed using any of the methods and/or embodiments disclosed herein (e.g., for the first and the second training datasets). In some embodiments, the supervised model is trained on any of the features disclosed herein.

Recurring basis. In some embodiments, the determination, from the supervised model 148, as to whether the test subject has the first cancer state or the second cancer state is repeated on a recurring basis for the test subject over time for minimal residual disease and recurrence monitoring. In some such embodiments, the determination, from the supervised model, as to whether the test subject has the first cancer state or the second cancer state is performed from a first sample obtained before and a second sample obtained after a cancer treatment of the test subject to assess the efficacy of the cancer treatment.

In some embodiments, the determination, from the supervised model 148, as to whether the test subject has the first cancer state or the second cancer state is repeated at each respective time point in a plurality of time points across an epoch, thus obtaining a corresponding cancer assessment, in a plurality of cancer assessments, for the test subject at each respective time point. In some embodiments this plurality of cancer assessments (where each cancer assessment is a determination, from the supervised model, as to whether the test subject has the first cancer state or the second cancer state at a particular time point) is used to determine a state or progression of a disease condition in the test subject during the epoch.

In some embodiments, each epoch is a period of months and each time point in the plurality of time points is a different time point in the period of months. In some embodiments, the period of months is less than four months. In some embodiments, each epoch is one month long. In some embodiments, each epoch is two months long. In some embodiments, each epoch is three months long. In some embodiments, each epoch is four months long. In some embodiments, each epoch is five, six, seven, eight, nine, ten, eleven, twelve, thirteen, fourteen, fifteen, sixteen, seventeen, eighteen, nineteen, twenty, twenty-one, twenty-two, twenty-three or twenty-four months long.

In some embodiments, the epoch is a period of years and each time point in the plurality of time points is a different time point in the period of years. In some embodiments, the period of years is between one year and ten years. In some embodiments, the period of years is one year, two years, three years, four years, five years, six years, seven years, eight years, nine years, or ten years. In some embodiment the epoch is between one and thirty years.

In some embodiments, the epoch is a period of hours and each time point in the plurality of time points is a different time point in the period of hours. In some embodiments, the period of hours is between one hour and twenty-four hours. In some embodiments, the period of hours is 1, 2, 3, 4, 5, 6, 7, 8, 9, 10, 11, 12, 13, 14, 15, 16, 17, 18, 19, 20, 21, 22, 23, or 24 hours.

In some embodiments, a diagnosis of the test subject is changed when the determination, from the supervised model 148, as to whether the test subject has the first cancer state or the second cancer state is observed to change by a threshold amount across the epoch. For instance, in some embodiments, the diagnosis is changed from having cancer to being in remission. As another example, in some embodiments, the diagnosis is changed from not having cancer to having cancer. As another example, in some embodiments, the diagnosis is changed from having a first stage of a cancer to having a second stage of a cancer. As another example, in some embodiments, the diagnosis is changed from having a second stage of a cancer to having a third stage of a cancer. As still another example, in some embodiments, the diagnosis is changed from having a third stage of a cancer to having a fourth stage of a cancer. As still another example, in some embodiments, the diagnosis is changed from having a cancer that has not metastasized to having a cancer that has metastasized.

In some embodiments, a prognosis of the test subject is changed when the determination, from the supervised model 148, as to whether the test subject has the first cancer state or the second cancer state is observed to change during an epoch. For example, in some embodiments, the prognosis involves life expectancy and the prognosis is changed from a first life expectancy to a second life expectancy, where the first and second life expectancy differ in their duration. In some embodiments, the change in prognosis increases the life expectancy of the subject. In some embodiments, the change in prognosis decreases the life expectancy of the subject.

In some embodiments, a treatment of the test subject is changed when the determination, from the supervised model, as to whether the test subject has the first cancer state or the second cancer state is observed to change during an epoch. In some embodiments, the changing of the treatment comprises initiating a cancer medication, increasing the dosage of a cancer medication, stopping a cancer medication, and/or decreasing the dosage of the cancer medication. In some embodiments, the changing of the treatment comprises initiating or terminating treatment of the test subject with Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof. In some embodiments, the changing of the treatment comprises increasing or decreasing a dosage of Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof administered to the test subject.

In some embodiments, a treatment regimen is applied to the test subject based, at least in part, on the determination, from the supervised model 148, as to whether the test subject has the first cancer state or the second cancer state. In some embodiments, the treatment regimen comprises applying an agent for cancer to the test subject. In some embodiments, the agent for cancer is a hormone, an immune therapy, radiography, or a cancer drug. In some embodiments, the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof.

In some embodiments, the test subject has been treated with an agent for cancer and the determination, from the supervised model 148, as to whether the test subject has the first cancer state or the second cancer state is used to evaluate a response of the subject to the agent for cancer. In some embodiments, the agent for cancer is a hormone, an immune therapy, radiography, or a cancer drug. In some embodiments, the agent for cancer is Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof.

In some embodiments, the test subject has been treated with an agent for cancer and the determination, from the supervised model, as to whether the test subject has the first cancer state or the second cancer state is used to determine whether to intensify or discontinue the agent for cancer in the test subject.

In some embodiments, the test subject has been subjected to a surgical intervention to address the cancer and the determination, from the supervised model 148, as to whether the test subject has the first cancer state or the second cancer state is used to evaluate a condition of the test subject in response to the surgical intervention. In some embodiments the condition is a metric based upon the determination, from the supervised model, as to whether the test subject has the first cancer state or the second cancer state using the methods provided in the present disclosure.

Methods for Training an Autoencoder to Detect a Cancer State

Another aspect of the present disclosure provides a method of forming a classifier 148 for detecting a cancer state. In such embodiments a training dataset is obtained in electronic form. The training dataset comprises, for each respective training subject in a plurality of training subjects, a corresponding methylation pattern and a corresponding nucleic acid sequence of each respective nucleic acid methylation fragment in a corresponding plurality of nucleic acid methylation fragments determined by a methylation sequencing of nucleic acids in a biological sample obtained from the respective training subject. The corresponding methylation pattern comprises a methylation state of each respective CpG site in a corresponding plurality of CpG sites in the respective nucleic acid methylation fragment. Each training subject in the plurality of training subjects has the cancer state.

An untrained autoencoder is trained using the training dataset. The autoencoder 132 includes an encoder 134 and a decoder 136. The autoencoder is trained using he corresponding methylation pattern and the corresponding nucleic acid sequence of each respective nucleic acid methylation fragment in each corresponding plurality of nucleic acid methylation fragments in the training dataset as input. The training comprises, for each corresponding nucleic acid sequence of each respective nucleic acid methylation fragment in each corresponding plurality of nucleic acid methylation fragments in the training dataset, evaluating a first error function for an error in the reconstruction by the autoencoder of the corresponding methylation pattern and the corresponding nucleic acid sequence of the corresponding nucleic acid methylation fragment, thereby forming a trained autoencoder.

In some embodiments, a test dataset is obtained in electronic form. The test dataset comprises, for a test subject, a corresponding methylation pattern and a corresponding nucleic acid sequence of each respective test nucleic acid methylation fragment in a plurality of test nucleic acid methylation fragments determined by a methylation sequencing of nucleic acids in a biological sample obtained from the test subject. The corresponding methylation pattern comprises a methylation state of each respective CpG site in a corresponding plurality of CpG sites in the respective test nucleic acid methylation fragment. The method further comprises applying all or a portion of the test dataset to the trained autoencoder to determine whether the test subject has the cancer state by computing, for each respective test nucleic acid methylation fragment in the plurality of test nucleic acid methylation fragments in the test dataset, a corresponding score based at least in part by a reconstruction of the corresponding methylation pattern of the respective nucleic acid methylation fragment by the trained autoencoder upon inputting the corresponding methylation pattern and the corresponding nucleic acid sequence of the respective test nucleic acid methylation fragment into the autoencoder.

In some embodiments, the cancer state is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the cancer state is a stage of a specified cancer. In some such embodiments, the specified cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the training dataset comprises a plurality of nucleic acid methylation fragments obtained from a plurality of training subjects having two or more cancer states (e.g., a plurality of specified cancers, stages, tissue of origins, subtypes, and/or cancer-associated attributes). In some such embodiments, obtaining the training dataset comprises pooling two or more biological samples.

Methods for Using Trained Autoencoders to Detect a Cancer State

Another aspect of the present disclosure provides a method of detecting a cancer state. A test dataset is obtained in electronic form. The test dataset comprises, for a test subject, a corresponding methylation pattern and a corresponding nucleic acid sequence of each respective nucleic acid methylation fragment in a plurality of nucleic acid methylation fragments determined by a methylation sequencing of nucleic acids in a biological sample obtained from the test subject. The corresponding methylation pattern comprises a methylation state of each respective CpG site in a corresponding plurality of CpG sites in the respective nucleic acid methylation fragment. The method further comprises applying the corresponding methylation pattern and the corresponding nucleic acid sequence of each respective nucleic acid methylation fragment in all or a portion of the plurality of nucleic acid methylation fragments to a trained autoencoder to determine whether the test subject has the cancer state by computing, for each respective nucleic acid methylation fragment in the all or the portion of the plurality of nucleic acid methylation fragments, a corresponding score based at least in part by a reconstruction of the corresponding methylation pattern of the respective nucleic acid methylation fragment by the trained autoencoder upon inputting the corresponding methylation pattern and the corresponding nucleic acid sequence of the respective nucleic acid methylation fragment into the trained autoencoder.

In some embodiments, the test dataset is obtained and/or processed using any of the methods and/or embodiments disclosed herein, and/or any combinations and/or modifications as will be apparent to one skilled in the art.

In some embodiments, the test dataset has the same state of cancer as the training dataset used for training the trained autoencoder. In some embodiments, the test dataset has a different state of cancer from the training dataset used for training the trained autoencoder.

In some embodiments, the using the test dataset and the trained autoencoder to detect a cancer state comprises any of the methods and/or embodiments described herein (e.g., using a second training dataset and a trained autoencoder as a unary classifier to detect a cancer state).

In some embodiments, the cancer state is absence of cancer.

In some embodiments, the cancer state is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the cancer state is a stage of a specified cancer. In some such embodiments, the specified cancer is adrenal cancer, biliary tract cancer, bladder cancer, bone/bone marrow cancer, brain cancer, breast cancer, cervical cancer, colorectal cancer, cancer of the esophagus, gastric cancer, head/neck cancer, hepatobiliary cancer, kidney cancer, liver cancer, lung cancer, ovarian cancer, pancreatic cancer, pelvis cancer, pleura cancer, prostate cancer, renal cancer, skin cancer, stomach cancer, testis cancer, thymus cancer, thyroid cancer, uterine cancer, lymphoma, melanoma, multiple myeloma, leukemia, or a combination thereof.

In some embodiments, the cancer state includes any of the cancer states described herein.

Systems for Cancer Condition Determination

Another aspect of the present disclosure provides a computer system for discriminating between a first cancer state and a second cancer state, where the first cancer state is different than the second cancer state. Another aspect of the present disclosure provides a computer system for forming a classifier for detecting a cancer state. Another aspect of the present disclosure provides a computer system for detecting a cancer state.

The computer system comprises at least one processor and a memory storing at least one program for execution by the at least one processor, the at least one program comprising instructions. In some embodiments, the at least one program comprises instructions for performing any of the methods and embodiments described herein and/or any combinations or alternatives thereof as will be apparent to one skilled in the art.

Another aspect of the present disclosure provides a non-transitory computer-readable storage medium storing program code instructions that, when executed by a processor, cause the processor to perform a method for discriminating between a first cancer state and a second cancer state, where the first cancer state is different than the second cancer state. Another aspect of the present disclosure provides a non-transitory computer-readable storage medium storing program code instructions that, when executed by a processor, cause the processor to perform a method of forming a classifier for detecting a cancer state. Another aspect of the present disclosure provides a non-transitory computer-readable storage medium storing program code instructions that, when executed by a processor, cause the processor to perform a method of detecting a cancer state.

In some embodiments, the program code instructions cause the processor to perform any of the methods and embodiments described herein and/or any combinations or alternatives thereof as will be apparent to one skilled in the art.

EXAMPLES

Example 1—Circulating Cell-Free Genome Atlas Study (CCGA)

Subjects from the CCGA [NCT02889978] were used in the Examples of the present disclosure.

CCGA is a prospective, multi-center, observational cfDNA-based early cancer detection study that has enrolled 15,254 demographically-balanced participants at 141 sites. Blood samples were collected from the 15,254 enrolled participants (56% cancer, 44% non-cancer) from subjects with newly diagnosed therapy-naive cancer (C, case) and participants without a diagnosis of cancer (noncancer [NC], control) as defined at enrollment.

In a first cohort (pre-specified substudy) (Approach 1), plasma cfDNA extractions were obtained from 3,583 CCGA and STRIVE participants (CCGA: 1,530 cancer subjects and 884 non-cancer subjects; STRIVE 1,169 non-cancer participants). STRIVE is a multi-center, prospective, cohort study enrolling women undergoing screening mammography (99, 259 participants enrolled). Blood was collected (n=1,785) from 984 CCGA participants with newly diagnosed, untreated cancer (20 tumor types, all stages) and 749 participants with no cancer diagnosis (controls) for plasma cfDNA extraction. This preplanned substudy included 878 cases, 580 controls, and 169 assay controls (n=1627) across twenty tumor types and all clinical stages.

Three sequencing assays were performed on the blood drawn from each participant: 1) paired cfDNA and white blood cell (WBC)-targeted sequencing (60,000×, 507 gene panel) for single nucleotide variants/indels (the ART sequencing assay); a joint caller removed WBC-derived somatic variants and residual technical noise; 2) paired cfDNA and WBC whole-genome sequencing (WGS; 35×) for copy number variation; a novel machine learning algorithm generated cancer-related signal scores; joint analysis identified shared events; and 3) cfDNA whole-genome bisulfite sequencing (WGBS; 34×) for methylation; normalized scores were generated using abnormally methylated fragments. In addition, tissue samples were obtained from participants with cancer only, such that 4) whole-genome sequencing (WGS; 30×) was performed on paired tumor and WBC gDNA for identification of tumor variants for comparison.

In a second pre-specified substudy (Approach 2), a targeted, rather than whole-genome, bisulfite sequencing assay was used to develop a classifier of cancer versus non-cancer and tissue-of-origin based on a targeted methylation sequencing approach. For Approach 2, 3,133 training participants and 1,354 validation samples (775 having cancer; 579 not having cancer as determined at enrollment, prior to confirmation of cancer versus non-cancer status) were used. Plasma cfDNA was subjected to a bisulfite sequencing assay (the COMPASS assay) targeting the most informative regions of the methylome, as identified from a unique methylation database and prior prototype whole-genome and targeted sequencing assays, to identify cancer and tissue-defining methylation signal. Of the original 3,133 samples reserved for training, only 1,308 samples were deemed clinically evaluable and analyzable. Analysis was performed on a primary analysis population n=927 (654 cancer and 273 non-cancer) and a secondary analysis population n=1,027 (659 cancer and 373 non-cancer). Finally, genomic DNA from formalin-fixed, paraffin-embedded (FFPE) tumor tissues and isolated cells from tumors was subjected to whole-genome bisulfite sequencing (WGBS) to generate a large database of cancer-defining methylation signals for use in panel design and in training to optimize performance.

See, e.g., Klein et al., 2018, "Development of a comprehensive cell-free DNA (cfDNA) assay for early detection of multiple tumor types: The Circulating Cell-free Genome Atlas (CCGA) study," J. Clin. Oncology 36(15), 12021-12021; doi: 10.1200/JCO.2018.36.15 suppl.12021, and Liu et al., 2019, "Genome-wide cell-free DNA (cfDNA) methylation signatures and effect on tissue of origin (TOO) performance," J. Clin. Oncology 37(15), 3049-3049; doi: 10.1200/JCO.2019.37.15 suppl.3049, each of which is hereby incorporated herein by reference in its entirety.

Example 2—Obtaining a Plurality of Sequence Reads

FIG. 7 is a flowchart of method 700 for preparing a nucleic acid sample for sequencing according to one embodiment. The method 700 includes, but is not limited to, the following steps. For example, any step of method 700 may comprise a quantitation sub-step for quality control or other laboratory assay procedures known to one skilled in the art.

In Block 702, a nucleic acid sample (DNA or RNA) is extracted from a subject. The sample may be any subset of the human genome, including the whole genome. The sample may be extracted from a subject known to have or suspected of having cancer. The sample may include blood, plasma, serum, urine, fecal, saliva, other types of bodily fluids, or any combination thereof. In some embodiments, methods for drawing a blood sample (e.g., syringe or finger prick) may be less invasive than procedures for obtaining a tissue biopsy, which may require surgery. The extracted sample may comprise cfDNA and/or ctDNA. For healthy individuals, the human body may naturally clear out cfDNA and other cellular debris. If a subject has a cancer or disease, ctDNA in an extracted sample may be present at a detectable level for diagnosis.

In Block 704, a sequencing library is prepared. Library procedures vary with the type of sequencing assay. For example, for methylation sequencing, bisulfite or enzymatic conversion can be used to convert un-methylated or methylated cytosines in a target nucleic acid molecule. In some embodiments, unique molecular identifiers (UMI) can be added to the nucleic acid molecules (e.g., DNA molecules) through adapter ligation. The UMIs are short nucleic acid sequences (e.g., 4-10 base pairs) that are added to ends of DNA fragments during adapter ligation. In some embodiments, UMIs are degenerate base pairs that serve as a unique tag that can be used to identify sequence reads originating from a specific DNA fragment. During PCR amplification following adapter ligation, the UMIs are replicated along with the attached DNA fragment. This provides a way to identify sequence reads that came from the same original fragment in downstream analysis. Due to disruption caused by bisulfite conversion, UMIs are not typically used. One of skill in the art would understand that, in embodiments where double-stranded target nucleic acids are preserved after methylation related processing (e.g., enzymatic conversion of only methylated cytosines), it is possible to use the UMI to track original nucleic acid molecules to facilitate sequencing error correction and subsequent variant analysis.

In some embodiments, nucleic acid sequence fragments from both the positive and reverse strands of cell-free nucleic acids in a biological sample are used in the datasets of the present disclosure.

In some embodiments where the sequencing disrupts UMIs or where UMIs are not available, such as bisulfate conversion, the nucleic acid sequences determined from the reverse strands of nucleic acid sequence fragments are converted to their reverse complement prior to use with the disclosed autoencoders.

In alternative embodiments, again where the sequencing disrupts UMIs or where UMIs are not available, the nucleic acid sequences determined from the reverse strands of nucleic acid sequence fragments are not converted to their reverse complements, but rather are flagged (e.g., electronically flagged as being from reverse strands) prior to use with the disclosed autoencoders. In other words, nucleic acid sequences obtained from the reverse strands of nucleic acid sequence fragments are electronically tracked in the sequencing process as being from reverse strands. In such embodiments, the autoencoder includes a channel for determining whether each such respective nucleic acid sequence is from a forward reading or reverse reading strand of a cell-free nucleic acid methylation fragment based on whether or not the data is flagged as being (or not being) from a reverse strand.

In still other embodiments, again where the sequencing disrupts UMIs or UMIs are unavailable, the nucleic acid sequences determined from the reverse strands of nucleic acid sequence fragments are converted to their reverse complements and also are flagged (e.g., electronically flagged as being from reverse strands) prior to use with the disclosed autoencoders. In other words, nucleic acid sequences obtained from the reverse strands of nucleic acid sequence fragments are electronically tracked in the sequencing process as being from reverse strands and are reverse complemented. In such embodiments, the autoencoder optionally includes a channel for determining whether each such respective nucleic acid sequence is from a forward reading or reverse reading strand of a cell-free nucleic acid fragment based on whether or not the data is flagged as being (or not being) from a reverse strand.

In Block 706, targeted DNA sequences are enriched from the library. During enrichment, hybridization probes (also referred to herein as "probes") are used to target, and pull down, nucleic acid fragments informative for the presence or absence of cancer (or disease), cancer status, or a cancer classification (e.g., cancer class or tissue of origin). For a given workflow, the probes may be designed to anneal (or hybridize) to a target (complementary) strand of DNA. The target strand may be the "positive" strand (e.g., the strand transcribed into mRNA, and subsequently translated into a protein) or the complementary "negative" strand. The probes may range in length from 10s, 100s, or 1000s of base pairs. In one embodiment, the probes are designed based on a methylation site panel. In one embodiment, the probes are designed based on a panel of targeted genes to analyze particular mutations or target regions of the genome (e.g., of the human or another organism) that are suspected to correspond to certain cancers or other types of diseases. Moreover, the probes may cover overlapping portions of a target region. In Block 708, these probes are used to general sequence reads of the nucleic acid sample.

FIG. 8 is a graphical representation of the process for obtaining sequence reads according to one embodiment. FIG. 8 depicts one example of a nucleic acid segment 800 from the sample. The nucleic acid segment 800 can be a single-stranded nucleic acid segment. In some embodiments, the nucleic acid segment 800 is a double-stranded cfDNA segment. The illustrated example depicts three regions 805A, 805B, and 805C of the nucleic acid segment that can be targeted by different probes. Specifically, each of the three regions 805A, 805B, and 805C includes an overlapping position on the nucleic acid segment 800. An example overlapping position is depicted in FIG. 8 as the cytosine ("C") nucleotide base 802. The cytosine nucleotide base 802 is located near a first edge of region 805A, at the center of region 805B, and near a second edge of region 805C.

In some embodiments, one or more (or all) of the probes are designed based on a gene panel or methylation site panel to analyze particular mutations or target regions of the genome (e.g., of the human or another organism) that are suspected to correspond to certain cancers or other types of diseases. By using a targeted gene panel or methylation site panel rather than sequencing all expressed genes of a genome, also known as "whole-exome sequencing," the method 800 may be used to increase sequencing depth of the target regions, where depth refers to the count of the number of times a given target sequence within the sample has been sequenced. Increasing sequencing depth reduces the required input amounts of the nucleic acid sample.

Hybridization of the nucleic acid sample 800 using one or more probes results in an understanding of a target sequence 870. As shown in FIG. 8, the target sequence 870 is the nucleotide base sequence of the region 805 that is targeted by a hybridization probe. The target sequence 870 can also be referred to as a hybridized nucleic acid fragment. For example, target sequence 870A corresponds to region 805A targeted by a first hybridization probe, target sequence 870B corresponds to region 805B targeted by a second hybridization probe, and target sequence 870C corresponds to region 805C targeted by a third hybridization probe. Given that the cytosine nucleotide base 802 is located at different locations within each region 805A-C targeted by a hybridization probe, each target sequence 870 includes a nucleotide base that corresponds to the cytosine nucleotide base 802 at a particular location on the target sequence 870.

After a hybridization step, the hybridized nucleic acid fragments are captured and may also be amplified using PCR. For example, the target sequences 870 can be enriched to obtain enriched sequences 880 that can be subsequently sequenced. In some embodiments, each enriched sequence 880 is replicated from a target sequence 870. Enriched sequences 880A and 880C that are amplified from target sequences 870A and 870C, respectively, also include the thymine nucleotide base located near the edge of each sequence read 880A or 880C. As used hereafter, the mutated nucleotide base (e.g., thymine nucleotide base) in the enriched sequence 880 that is mutated in relation to the reference allele (e.g., cytosine nucleotide base 802) is considered as the alternative allele. Additionally, each enriched sequence 880B amplified from target sequence 870B includes the cytosine nucleotide base located near or at the center of each enriched sequence 880B.

In Block 708, sequence reads are generated from the enriched DNA sequences, e.g., enriched sequences 880 shown in FIG. 8. Sequencing data may be acquired from the enriched DNA sequences by known means in the art. For example, the method 800 may include next-generation sequencing (NGS) techniques including synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators.

In some embodiments, the sequence reads may be aligned to a reference genome using known methods in the art to determine alignment position information. The alignment position information may indicate a beginning position and an end position of a region in the reference genome that corresponds to a beginning nucleotide base and end nucleotide base of a given sequence read. Alignment position information may also include sequence read length, which can be determined from the beginning position and end position. A region in the reference genome may be associated with a gene or a segment of a gene.

In various embodiments, a sequence read is comprised of a read pair denoted as $R_1$ and $R_2$. For example, the first read $R_1$ may be sequenced from a first end of a nucleic acid fragment whereas the second read $R_2$ may be sequenced from the second end of the nucleic acid fragment. Therefore, nucleotide base pairs of the first read $R_1$ and second read $R_2$ may be aligned consistently (e.g., in opposite orientations) with nucleotide bases of the reference genome. Alignment position information derived from the read pair $R_1$ and $R_2$ may include a beginning position in the reference genome that corresponds to an end of a first read (e.g., $R_1$) and an end position in the reference genome that corresponds to an end of a second read (e.g., $R_2$). In other words, the beginning position and end position in the reference genome represent the likely location within the reference genome to which the nucleic acid fragment corresponds. An output file having SAM (sequence alignment map) format or BAM (binary)

format may be generated and output for further analysis such as methylation state determination.

Example 3—Generation of Methylation State Vector

FIG. 9 is a flowchart describing a process 900 of sequencing a fragment of cfDNA to obtain a methylation state vector, according to an embodiment in accordance with the present disclosure.

Referring to step 902, the cfDNA fragments are obtained from the biological sample (e.g., as discussed above in conjunction with Example 2). Referring to step 920, the cfDNA fragments are treated to convert unmethylated cytosines to uracils. In one embodiment, the DNA is subjected to a bisulfite treatment that converts the unmethylated cytosines of the fragment of cfDNA to uracils without converting the methylated cytosines. For example, a commercial kit such as the EZ DNA Methylation™—Gold, EZ DNA Methylation™—Direct or an EZ DNA Methylation™—Lightning kit (available from Zymo Research Corp (Irvine, Calif.)) is used for the bisulfite conversion in some embodiments. In other embodiments, the conversion of unmethylated cytosines to uracils is accomplished using an enzymatic reaction. For example, the conversion can use a commercially available kit for converting unmethylated cytosines to uracils, such as APOBEC-Seq (NEBiolabs, Ipswich, Mass.).

From the converted cfDNA fragments, a sequencing library is prepared (step 930). Optionally, the sequencing library is enriched 935 for cfDNA fragments, or genomic regions, that are informative for cancer status using a plurality of hybridization probes. The hybridization probes are short oligonucleotides capable of hybridizing to particularly specified cfDNA fragments, or targeted regions, and enriching for those fragments or regions for subsequent sequencing and analysis. Hybridization probes may be used to perform a targeted, high-depth analysis of a set of specified CpG sites of interest to the researcher. Once prepared, the sequencing library or a portion thereof can be sequenced to obtain a plurality of sequence reads (940). The sequence reads may be in a computer-readable, digital format for processing and interpretation by computer software.

From the sequence reads, a location and methylation state for each of CpG site is determined based on alignment of the sequence reads to a reference genome (950). A methylation state vector for each fragment specifying a location of the fragment in the reference genome (e.g., as specified by the position of the first CpG site in each fragment, or another similar metric), a number of CpG sites in the fragment, and the methylation state of each CpG site in the fragment (960).

For details regarding WGBS, see, e.g., United States Patent Application No. Publication No. US 2019-0287652 A1, entitled "Anomalous Fragment Detection and Classification," and United States Patent Publication No. 2020-0385813 A1, entitled "Systems and Methods for Estimating Cell Source Fractions Using Methylation Information," each of which is hereby incorporated by reference.

Conclusion

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A method comprising:

A) obtaining a test dataset, in electronic form, wherein:
the test dataset comprises, for a test subject, a corresponding methylation pattern and a corresponding nucleic acid sequence of each respective nucleic acid methylation fragment in a plurality of nucleic acid methylation fragments determined by a methylation sequencing of nucleic acids in a biological sample obtained from the test subject, and
the corresponding methylation pattern comprises a methylation state of each respective CpG site in a corresponding plurality of CpG sites in the respective nucleic acid methylation fragment; and B) training an autoencoder by a training process that comprises two stages, and the two stages comprises:
using a first stage of supervised training to train an untrained autoencoder using a first methylation pattern dataset that comprises training samples of a first cancer state indicating an absence of cancer, wherein the first stage of supervised training determines similarities of output reconstructions compared to the first methylation pattern dataset,
selecting a second methylation pattern dataset based on one or more selection criteria, the second methylation pattern dataset comprising training samples of the first cancer state and training samples of a second cancer state indicating a presence of cancer according to the one or more selection criteria, and
using a second stage of supervised training to train the trained autoencoder using the second methylation pattern dataset to generate reconstruction scores;

C) applying the trained autoencoder to the corresponding methylation pattern and the corresponding nucleic acid sequence of each respective nucleic acid methylation fragment in all or a portion of the plurality of nucleic acid methylation fragments to determine whether the test subject has a cancer state, wherein the trained autoencoder includes 1000 or more weights, and wherein the C) applying comprises:
for each respective nucleic acid methylation fragment in the all or the portion of the plurality of nucleic acid methylation fragments:
(i) using the trained autoencoder to reconstruct a corresponding methylation pattern based on the corresponding nucleic acid sequence of the respective nucleic acid methylation fragment;
(ii) computing a corresponding score determined at least in part by the reconstructed methylation pattern; and
(ii) determining, as an output, whether the test subject has the cancer state using each corresponding score;

D) determining, based on the output, that the cancer state of the test subject is the second cancer state; and E) causing an administration of a treatment of the cancer state to the test subject based on determining that the cancer state is the second cancer state, wherein the treatment includes administering a dosage of Lenalidomid, Pembrolizumab, Trastuzumab, Bevacizumab, Rituximab, Ibrutinib, Human Papillomavirus Quadrivalent (Types 6, 11, 16, and 18) Vaccine, Pertuzumab, Pemetrexed, Nilotinib, Nilotinib, Denosumab, Abiraterone acetate, Promacta, Imatinib, Everolimus, Palbociclib, Erlotinib, Bortezomib, Bortezomib, or a generic equivalent thereof.

2. The method of claim 1, wherein the corresponding score of the respective nucleic acid methylation fragment:

is determined by a correctness of the reconstruction of the corresponding methylation pattern of the respective nucleic acid methylation fragment by the trained autoencoder, and is independent of a correctness of the reconstruction of the corresponding nucleic acid sequence of the respective nucleic acid methylation fragment by the trained autoencoder.

3. The method of claim 1, wherein the corresponding score of the respective nucleic acid methylation fragment:

is determined by a correctness of the reconstruction of the corresponding methylation pattern of the respective nucleic acid methylation fragment by the trained autoencoder, and is further determined by the correctness of the reconstruction of the corresponding nucleic acid sequence of the respective nucleic acid methylation fragment by the trained autoencoder.

4. The method of claim 2, wherein the correctness of the reconstruction of the corresponding methylation pattern of the respective nucleic acid methylation fragment by the trained autoencoder is determined, at least in part, by a Hamming distance between the reconstruction of the corresponding methylation pattern of the respective nucleic acid methylation fragment and the actual methylation pattern of the respective nucleic acid methylation fragment.

5. The method of claim 1, wherein the plurality of nucleic acid methylation fragments comprises one thousand or more, ten thousand or more, 100 thousand or more, one million or more, ten million or more, 100 million or more, 500 million or more, one billion or more, two billion or more, three billion or more, four billion or more, five billion or more, six billion or more, seven billion or more, eight billion or more, nine billion or more, or 10 billion or more nucleic acid methylation fragments.

6. The method of claim 1, wherein after the A) obtaining and prior to the C) applying:

filtering the plurality of nucleic acid methylation fragments by removing, from the plurality of nucleic acid methylation fragments, each respective nucleic acid methylation fragment that fails to satisfy one or more selection criteria.

7. The method of claim 6, wherein:

the respective nucleic acid methylation fragment fails to satisfy a selection criterion in the one or more selection criteria when the methylation pattern of the respective nucleic acid methylation fragment has an output p-value that fails to satisfy a p-value threshold, and the output p-value of the respective nucleic acid methylation fragment is determined, at least in part, based upon a comparison of the methylation pattern of the respective nucleic acid methylation fragment over a plurality of CpG sites of the respective nucleic acid methylation fragment to a corresponding distribution of methylation patterns of those nucleic acid methylation fragments in a training dataset that have the corresponding plurality of CpG sites.

8. The method of claim 6, wherein:

the respective nucleic acid methylation fragment fails to satisfy a selection criterion in the one or more selection criteria when an output p-value provided by a trained Markov model, responsive to input of the methylation pattern of the respective nucleic acid methylation fragment, fails the selection criterion, and the trained Markov model is trained, at least in part, based upon evaluation of a methylation state of each CpG site in a plurality of CpG sites of the respective nucleic acid methylation fragment across those nucleic acid methylation fragments in a training dataset that have the corresponding plurality of CpG sites.

9. The method of claim 6, wherein the respective nucleic acid methylation fragment fails to satisfy a selection criterion in the one or more selection criteria when the respective nucleic acid methylation fragment has less than a threshold number of CpG sites.

10. The method of claim 9, wherein the threshold number of CpG sites is 4, 5, 6, 7, 8, 9, or 10.

11. The method of claim 6, wherein the respective nucleic acid methylation fragment fails to satisfy a selection criterion in the one or more selection criteria when the respective nucleic acid methylation fragment has less than a threshold number of residues.

12. The method of claim 11, wherein the threshold number of residues is a fixed value between 20 and 90.

13. The method of claim 6, wherein the filtering removes a nucleic acid methylation fragment in the plurality of nucleic acid methylation fragments that has the same corresponding methylation pattern and the same corresponding nucleic acid sequence as another nucleic acid methylation fragment in the plurality of nucleic acid methylation fragments.

14. The method of claim 1, wherein the trained autoencoder is a variational autoencoder, a stacked denoising deep autoencoder, a deep recurrent autoencoder, a convolutional autoencoder, or a transformer network.

15. The method of claim 1, wherein the trained autoencoder is a deep recurrent autoencoder and the B) applying, for a respective nucleic acid methylation fragment in the plurality of nucleic acid methylation fragments:

feeds a first track of the deep recurrent autoencoder the corresponding nucleic acid sequence of the respective nucleic acid methylation fragment broken up into a plurality of k-mers, and feeds a second track of the deep recurrent autoencoder the corresponding methylation pattern of the respective nucleic acid methylation fragment.

16. The method of claim 1, wherein the trained autoencoder is a deep recurrent autoencoder and the C) applying the trained autoencoder:

feeds a first track of the deep recurrent autoencoder the corresponding nucleic acid sequence of the respective nucleic acid methylation fragment on a residue basis, and feeds a second track of the deep recurrent autoencoder the corresponding methylation pattern of the respective nucleic acid methylation fragment.

17. The method of claim 1, wherein the trained autoencoder comprises:

an encoder that encodes the corresponding methylation pattern and the corresponding nucleic acid sequence of the corresponding nucleic acid methylation fragment in the plurality of nucleic acid methylation fragments thereby forming a plurality of latent features; and a decoder that decodes the plurality of latent features into a reconstruction of the corresponding methylation pattern and the corresponding nucleic acid sequence of the corresponding nucleic acid methylation fragment.

18. The method of claim 1, wherein the methylation state of a respective CpG site in the plurality of CpG sites in the respective nucleic acid methylation fragment is:

methylated when the respective CpG site is determined by the methylation sequencing to be methylated, unmethylated when the respective CpG site is determined by the methylation sequencing to not be methylated, and flagged as "other" when the methylation sequencing is unable to call the methylation state of the respective CpG site as methylation or unmethylated.

19. The method of claim 1, wherein the methylation sequencing is i) whole genome methylation sequencing or ii) targeted DNA methylation sequencing using a plurality of nucleic acid probes.

20. The method of claim 1, wherein the second cancer state is a stage of a specified cancer.

21. The method of claim 1, wherein the methylation sequencing of nucleic acids in a biological sample obtained from the respective subject is methylation sequencing of cell-free nucleic acids in the biological sample.

22. The method of claim 1, wherein the biological sample comprises blood, whole blood, plasma, serum, urine, cerebrospinal fluid, fecal, saliva, sweat, tears, pleural fluid, pericardial fluid, or peritoneal fluid of the test subject.

23. The method of claim 1, wherein the test dataset comprises:

a first corresponding nucleic acid sequence of a first nucleic acid methylation fragment in the plurality of nucleic acid methylation fragments determined by the methylation sequencing of nucleic acids in the biological sample obtained from the test subject wherein the first corresponding nucleic acid sequence is from a forward strand or a reverse strand of the first nucleic acid methylation fragment or wherein the first corresponding nucleic acid sequence is a reverse strand of the first nucleic acid methylation fragment and is in reverse complement form or is flagged as being reverse strand of the first nucleic acid methylation fragment.

* * * * *